United States Patent
Cai et al.

(10) Patent No.: US 11,345,710 B2
(45) Date of Patent: May 31, 2022

(54) IMIDAZO[1,2-B]PYRIMIDO[4,5-D] PYRIDAZIN-5(6H)-ONES AND THE USE THEREOF

(71) Applicant: IMPACT THERAPEUTICS (SHANGHAI), INC, Shanghai (CN)

(72) Inventors: Suixiong Cai, Shanghai (CN); Ye Edward Tian, Shanghai (CN); Zhiqiang Dong, Shanghai (CN); Xiaozhu Wang, Nanjing (CN)

(73) Assignee: IMPACT THERAPEUTICS (SHANGHAI), INC, Shanghai (CN)

( * ) Notice: Subject to any disclaimer, the term of this patent is extended or adjusted under 35 U.S.C. 154(b) by 23 days.

(21) Appl. No.: 16/629,185

(22) PCT Filed: Jul. 10, 2018

(86) PCT No.: PCT/CN2018/095080
§ 371 (c)(1),
(2) Date: Jan. 7, 2020

(87) PCT Pub. No.: WO2019/011228
PCT Pub. Date: Jan. 17, 2019

(65) Prior Publication Data
US 2020/0131192 A1    Apr. 30, 2020

(30) Foreign Application Priority Data

Jul. 10, 2017  (CN) .......................... 201710556148.7

(51) Int. Cl.
*C07D 487/14* (2006.01)
*A61P 35/00* (2006.01)
*A61K 45/06* (2006.01)

(52) U.S. Cl.
CPC ............ *C07D 487/14* (2013.01); *A61P 35/00* (2018.01); *A61K 45/06* (2013.01)

(58) Field of Classification Search
CPC .................................................. C07D 487/14
USPC ...................................................... 514/248
See application file for complete search history.

(56) References Cited

U.S. PATENT DOCUMENTS

2012/0220572 A1   8/2012   Tong et al.
2016/0318936 A1   11/2016  Harrison et al.

FOREIGN PATENT DOCUMENTS

CN       103703005 A      4/2014
CN       105829315 A      8/2016
WO       WO 2013013031 A1 1/2013

OTHER PUBLICATIONS

King, Med. Chem., Principle and Practice (1994), pp. 206-208.*
International Search Report for International Application No. PCT/CN2018/095082, dated Sep. 12, 2018, 4 pages.

* cited by examiner

*Primary Examiner* — Taofiq A Solola
(74) *Attorney, Agent, or Firm* — Sterne, Kessler, Goldstein & Fox P.L.L.C.

(57) ABSTRACT

Disclosed are imidazo[1,2-b]pyrimido[4,5-d]pyridazin-5 (6H)-one compounds, specifically represented by the Formula I:

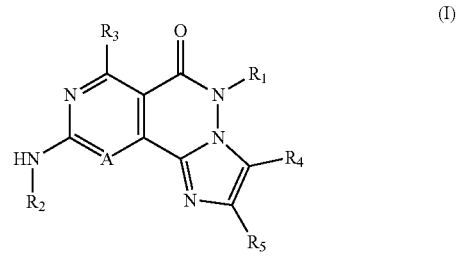

or a pharmaceutically acceptable salt or prodrug thereof, wherein A and $R_1$-$R_5$ are defined herein. Compounds having Formula I are Wee1 kinase inhibitors. Therefore, compounds of the disclosure may be used to treat diseases caused by abnormal Wee1 activity.

20 Claims, No Drawings

IMIDAZO[1,2-B]PYRIMIDO[4,5-D]PYRID-AZIN-5(6H)-ONES AND THE USE THEREOF

FIELD OF THE DISCLOSURE

This disclosure is in the field of medicinal chemistry. In particular, the disclosure relates to imidazo[1,2-b]pyrimido[4,5-d]pyridazin-5(6H)-ones, and the use of these compounds.

BACKGROUND OF THE INVENTION

The process of growth and proliferation of eukaryotic cell includes that the parent cell produces two identical daughter cells through the mitosis of the cell chromosome by accurately replicating its genome containing genetic information. This process of cell proliferation and division is called the cell cycle, and it involves the process of a cell going from one division to the next. The cell cycle consists of four growth stages: the G1 phase of massive synthesis of proteins and RNA after mitosis, the S phase of DNA synthesis and replication, the G2 phase of preparation before mitosis, and the M phase of mitosis. Cells divide and proliferate through the cell cycle, or stop, depending on the state and needs of the cell. It is necessary to keep genetic information complete and correct during cell proliferation and division. Whether or not to enter the next phase of cell cycle until the completion of the whole cell cycle is ensured and completed through the checkpoints in the cell cycle process.

During the whole process of cell cycle, there are many cell cycle checkpoints. Each cell cycle checkpoint consists of a very complex system and is composed of multiple factors. In the G1 phase, the checkpoint determines whether to enter the cell cycle by examining the state inside and outside the cell, so as to determine whether the cell enters the S phase of DNA synthesis. The G1 checkpoint is a complex system that includes the famous CDK4/CDK6. Another important checkpoint is the so-called G2-M checkpoint, where the cell completes DNA replication (S phase) and enters the cell growth phase (G2 phase). This checkpoint examines whether there is any DNA damage or defect after the cells have synthesized DNA, which determines whether the cells undergo mitosis (M-phase) with the separation of the following chromosomes. Cell cycle checkpoints at this stage include complex kinase Cdk1 complexes including Cyclin-B-cdc2 (Nurse, P., 1990, Nature 344, 503-508). Activation of Cdk1 leads to initiation of mitosis, and subsequent inactivation is accompanied by the completion of mitosis. The activity of Cdk1 is regulated by cdc2 binding to Cyclin-A or Cyclin-B and its phosphorylation. For example, the activation of the cyclin B-Cdk1 complex causes mitosis (Lindqvist, A., et al, 2009, The Journal of cell biology 185, 193-202). Cdc2 is kept inactive by phosphorylation before the cell entering mitosis. Its phosphorylation state is achieved by tyrosine kinase Wee1, etc. In addition, there are M-phase cell cycle checkpoints.

Tyrosine 15 (Y15) on Cdk1 is phosphorylated by Wee1, thus inhibiting the activity of Cdk1(McGowan, C. H., et al, 1993, The EMBO journal 12, 75-85; Parker, L. L., et al, 1992, Science 257, 1955-1957). Therefore, Wee1 is a key inhibitory regulator of Cdk1 activity and plays an important role in G2-M phase checkpoints to ensure the entry into mitosis without DNA damage after DNA replication (O'Connell, et al, 1997, The EMBO journal 16, 545-554). Loss or inactivation of Wee1 may result in premature entry into mitosis, leading to mitotic failure and cell death (Stumpff, J., et al, 2004, Curr Biol 14, 2143-2148). Some tumor cells have functional deficiency in G1 cell cycle checkpoint and rely on G2-M phase checkpoints to ensure the progress of cell cycle (Sancar, A., et al, 2004, Annual review of biochemistry 73, 39-85). Due to the loss of p53 protein function, in these cancer cells, the loss of Wee1 expression or the inhibition of Wee1 activity will result in the loss of G2-M phase checkpoints, making tumor cells very sensitive to DNA damage, and this sensitivity is especially prominent in tumor cells that lose the ability of G1 phase checkpoint (Wang, Y., et al, 2004, Cancer biology & therapy 3, 305-313).

In summary, inhibition of Wee1 activity can selectively promote the death of cancer cells with defective cell cycle checkpoints; at the same time, has little effect on normal cells with normal cell cycle checkpoints. Therefore, Wee1 inhibitors may be used as targeted drugs for the treatment of cancer and other cell proliferation disorders.

In addition, because the inhibition of Wee1 activity increases the sensitivity of cells to DNA damage, Wee1 inhibitors can be used in combination with anticancer drugs that cause DNA damage or inhibit DNA repair mechanism, including PARP inhibitors, e.g. Olaparib, Niraparib, Rucaparib and Talazoparib; HDAC inhibitors, e.g. vorinotat, lomidacin, pabista, and belistatin; and the like, for treating cancer or other cell proliferation disorders. Wee1 inhibitors may also be used in combination with other anticancer drugs related to cell cycle checkpoints of cell division, including Chk1/2 inhibitors, CDK4/6 inhibitors such as Paboxini, ATM/ATR inhibitors etc. for the treatment of cancer and other diseases.

The study of Karnak et al. (Clin Cancer Res, 2014, 20(9): 5085-5096) shows that the combination of Wee1 inhibitor AZD1775 and PARP inhibitor olaparib can enhance the sensitivity of pancreatic cancer after radiotherapy. The results confirmed that the combination of Wee1 inhibitor and PARP inhibitor could enhance the radiosensitivity of pancreatic cancer, and supported the hypothesis that Wee1 inhibition could sensitize the cell to PARP inhibitor, i.e., sensitize the cell to radiotherapy by inhibiting the function of DNA repair and G2 checkpoint. It can eventually lead to the accumulation of unrepaired damaged DNA until the cell dies.

In addition, it was reported (BMC Cancer, 2015, 15: 462) that Wee1 inhibitor MK1775 and Chk1/2 inhibitor AZD7762 were used together in malignant melanoma cell and xenograft models. The results showed that the combined use of Wee1 and Chk1/2 inhibitors could synergize the inhibitory effect of single drug, thus reducing the proliferation capacity of tumor cells and activating the apoptosis mechanism. The combination of both inhibitors can inhibit tumor growth better in the xenograft model.

AZD1775 is the first Wee1 kinase inhibitor with single antitumor activity in a preclinical model. Phase I clinical studies showed the single drug efficacy of AZD1775 in patients with solid tumors with BRCA mutations, and the inhibition mechanism of Wee1 kinase was confirmed by paired tumor biopsy finding changes related to targeting and DNA damage response (J Clin Oncol, 2015, 33: 3409-3415). In a clinical phase I trial of AZD1775, which enrolled in more than 200 patients, the efficacy of AZD1775 alone or in combination with gemcitabine, cisplatin or carboplatin in the treatment of patients with advanced solid tumors was studied, showing that AZD1775 alone or in combination with chemotherapy was safe and tolerable at a certain dose. Of 176 evaluable patients, 94 (53%) had stable disease as the best response, and 17 (10%) had partial response. Importantly, the response rate of AZD1775 in patients with TP53 mutation (n=19) was 21%, while that in TP53 wild-type patients (n=33) was 12%, showing great potential for patients with TP53 mutation (J Clin Oncol, 2016 Sep. 6, pii: JCO675991).

WO2012161812 disclosed the following tricyclic compounds as Wee1 kinase inhibitors, wherein, X is N or $CR^1$; Y is N or $CR^2$; Z is O, S or NH; $R^1$ and $R^2$ are H or $C_{1-6}$ alkyl; $R^3$ is $C_{1-8}$ alkyl, $C_{2-8}$ alkenyl, $C_{3-8}$ cycloalkyl, aryl, or heteroaryl etc; $R^4$ is phenyl, naphthyl, tetrahydronaphthyl, indenyl or indanyl, or 5-16 member monocyclic, bicyclic or tricyclic heterocyclic groups, etc.

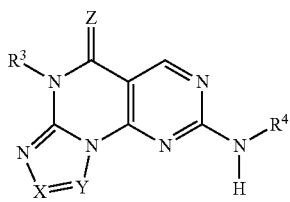

WO2005021551 disclosed the following tetracyclic pyrimidine or pyridine compounds as protein kinase inhibitors, wherein, X is N or CH; Y is NH, N(CN), O or S; L is a 4-atom chain made up of C and N atoms; $R^a$ is H, $C_{1-8}$ alkyl, CN, phenyl or benzyl; $R^1$ and $R^2$ are independently substituted saturated or unsaturated 5-, 6-, or 7-member monocyclic group, or 6-, 7-, 8-, 9-, 10- or 11-member bicyclic group (including 0, 1, 2, 3 or 4 atoms selected from N, O and S, of which O and S atoms do not exist at the same time, and the C atoms in the ring are substituted by 0, 1 or 2 oxygen groups) etc.

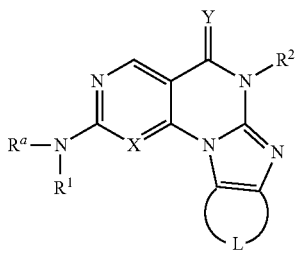

SUMMARY OF THE DISCLOSURE

The disclosure provides novel imidazo[1,2-b]pyrimido[4,5-d]pyridazin-5(6H)-ones, as represented by Formulae I, II and III as kinase inhibitors, especially Wee1 kinase inhibitors.

The present disclosure also provides pharmaceutical compositions comprising a compound of Formula I, II or III in an effective amount for the treatment of cancer.

In a concrete embodiment, the pharmaceutical composition useful for the treatment of cancer may also contain one or more pharmaceutically acceptable carriers or diluents.

In a concrete embodiment, the pharmaceutical composition useful for the treatment of cancer may also contain at least one known anticancer drugs or its pharmaceutically acceptable salts.

The disclosure is also directed to methods for the preparation of novel compounds of Formulae I, II and III.

DETAILED DESCRIPTION OF THE DISCLOSURE

The disclosure finds novel imidazo[1,2-b]pyrimido[4,5-d]pyridazin-5(6H)-ones as kinase inhibitors, especially Wee1 kinase inhibitors, as represented by Formulae I, II and III.

It should be understood that the characteristics of the embodiments described herein can be arbitrarily combined to form the technical solution of this disclosure. The definitions of each group herein shall apply to any of the embodiments described herein. For example, the definitions of substituents for alkyl groups herein shall apply to any of the embodiments described herein unless the substituents for alkyl groups are clearly defined in the embodiment.

Specifically, compounds of the present disclosure are represented by Formula I:

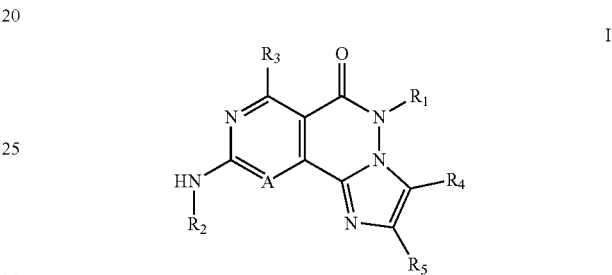

or pharmaceutically acceptable salts or prodrugs thereof, wherein:

A is N or $CR_6$;

$R_1$ is H, optionally substituted $C_1$-$C_8$alkyl, optionally substituted $C_2$-$C_8$ alkenyl, optionally substituted $C_3$-$C_8$cycloalkyl, optionally substituted aryl, an optionally substituted heterocyclic group or optionally substituted heteroaryl;

$R_2$ is an optionally substituted carbocyclic group, an optionally substituted heterocyclic group, optionally substituted aryl, or optionally substituted heteroaryl;

$R_3$-$R_6$ are independently H, halo, optionally substituted amino, optionally substituted alkoxy, optionally substituted $C_{1-10}$ alkyl (such as haloalkyl, hydroxyalkyl, aminoalkyl, and carboxyalkyl), alkenyl, alkynyl, nitro, cyano, acylamido, hydroxy, thiol, acyloxy, azido, carboxy, ethylenedioxo, hydroxyacylamido or optionally substituted alkylthiol.

In one or more embodiment, A is N.

In each of the foregoing embodiments in Formula I, $R_1$ and $R_2$ are optionally substituted aryl.

In each of the foregoing embodiments in Formula I, $R_3$ is H.

In each of the foregoing embodiments in Formula I, $R_4$ and $R_5$ are H, and optionally substituted $C_1$-$C_6$ alkyl.

In each of the foregoing embodiments in Formula I, $R_4$ is H or unsubstituted $C_1$-$C_6$ alkyl.

In each of the foregoing embodiments in Formula I, $R_5$ is H or $C_1$-$C_6$ alkyl optionally substituted by hydroxy, such as hydroxy $C_1$-$C_6$ alkyl.

In each of the foregoing embodiments in Formula I, $R_6$ is H.

In each of the foregoing embodiments in Formula I, the substitutents on $R_1$ are selected from any one, two, three or four of the following groups: halo, $C_1$-$C_6$ alkyl, $C_1$-$C_6$ alkoxy, and halo $C_1$-$C_6$ alkyl.

In each of the foregoing embodiments in Formula I, $R_1$ is selected from: $C_2$-$C_8$ alkenyl, and phenyl which is optionally substituted by 1-4 substituents selected from halo and $C_1$-$C_6$ alkyl.

In each of the foregoing embodiments in Formula I, $R_1$ is selected from phenyl which is optionally substituted by 1-4 substituents selected from halo and $C_1$-$C_6$ alkyl; in some embodiments, the number of substituents is 2; in some embodiments, at least one substituent is in the ortho position; in some embodiments, at least one substituent is halo; in some embodiments, the number of substituents on the phenyl is 2, both are located adjacent to each other, and wherein at least one is halo.

In each of the foregoing embodiments in Formula I, $R_1$ is selected from optionally substituted $C_2$-$C_8$alkenyl.

In each of the foregoing embodiments in Formula I, the substituents on $R_2$ are selected from any one, two, three or four of the following groups: optionally substituted $C_1$-$C_6$ alkyl, optionally substituted oxy group, halo, and optionally substituted heterocyclic group; preferably, the substituents on these optionally substituted group may be 1-4 groups selected from the following groups: $C_1$-$C_6$ alkyl and —$NR_aR_b$, wherein $R_a$ and $R_b$ are each independently H and $C_1$-$C_6$ alkyl; preferably, the heterocyclic group is selected from piperazinyl and piperidinyl.

In each of the foregoing embodiments in Formula I, the substituents on $R_2$ are selected from any one, two, three or four of the following groups: optionally substituted piperazinyl, optionally substituted piperidinyl, $C_1$-$C_6$ alkyl, halo, and optionally substituted $C_1$-$C_6$ alkoxy; preferably, the substituents on the optionally substituted group may be 1-4 groups selected from the following groups: $C_1$-$C_6$ alkyl and —$NR_aR_b$, wherein $R_a$ and $R_b$ are independently H and $C_1$-$C_6$ alkyl.

In each of the foregoing embodiments in Formula I, the optionally substituted piperazinyl is the piperazinlyl which can be substituted by 1, 2 or 3 groups selected from: $C_1$-$C_6$ alkyl.

In each of the foregoing embodiments in Formula I, the piperazine group has at least one substituent at the para-position, and optionally, one or two substituents at the meta-position.

In each of the foregoing embodiments in Formula I, the optionally substituted piperidinyl is the piperidinyl which can be substituted by 1 group selected from $C_1$-$C_6$ alkyl and —$NR_aR_b$, wherein $R_a$ and $R_b$ are independently H and $C_1$-$C_6$ alkyl.

In each of the foregoing embodiments in Formula I, $R_2$ is selected from optionally substituted phenyl and optionally substituted tetrahydroisoquinolinyl.

In each of the foregoing embodiments in Formula I, $R_2$ is selected from phenyl substituted by piperazinyl which can be optionally substituted, phenyl substituted by pyridinyl which can be optionally substituted, and tetrahydroisoquinolinyl optionally substituted by 1-3 $C_1$-$C_6$ alkyl.

In each of the foregoing embodiments in Formula I, the piperazinyl is optionally substituted by 1-3 groups selected from $C_1$-$C_6$ alkyl.

In each of the foregoing embodiments in Formula I, the piperidinyl is optionally substituted by 1 group selected from $C_1$-$C_6$ alkyl and —$NR_aR_b$, wherein $R_a$ and $R_b$ are independently H and $C_1$-$C_6$ alkyl.

In each of the foregoing embodiments in Formula I, $R_4$ and $R_5$ are independently H and optionally substituted $C_1$-$C_6$ alkyl, preferably, $R_4$ and $R_5$ are both H and $C_1$-$C_6$ alkyl.

One group of preferred compounds of Formula I in the present disclosure are represented by Formula II:

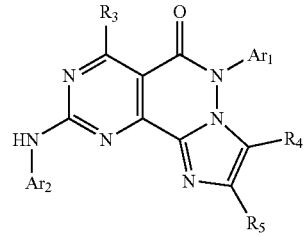

or pharmaceutically acceptable salts or prodrugs thereof, wherein:

$R_3$-$R_5$ are defined as in Formula I;

$Ar_1$ and $Ar_2$ are each independently optionally substituted aryl, optionally substituted heterocyclic group or optionally substituted heteroaryl;

In one or more of the embodiments in Formula II, $R_3$ is H.

In each of the foregoing embodiments in Formula II, $R_4$ and $R_5$ are H and optionally substituted $C_1$-$C_6$ alkyl.

In each of the foregoing embodiments in Formula II, $Ar_1$ and $Ar_2$ are each independently optionally substituted aryl, optionally substituted heterocyclic group or optionally substituted heteroaryl; preferably, $Ar_1$ and $Ar_2$ are each independently optionally substituted aryl, more preferably optionally substituted phenyl.

In each of the foregoing embodiments in Formula II, the substituents on $Ar_1$ is selected from any one, two, three or four groups of the following groups: halo and $C_1$-$C_6$ alkyl; in some embodiments, the number of substituents is 2; in some embodiments, at least one substituent is in the ortho-position; in some embodiments, at least one substituent is halo; in some embodiments, the number of substituents on the phenyl is 2, both are located adjacent to each other, and wherein at least one is halo.

In each of the foregoing embodiments in Formula II, $Ar_1$ is selected from phenyl optionally substituted by 1-4 substituents selected from halo and $C_1$-$C_6$ alkyl.

In each of the foregoing embodiments in Formula II, the substituents on $Ar_2$ is selected from any one, two, three or four groups of the following groups: optionally substituted $C_1$-$C_6$ alkyl, optionally substituted oxy group, halo and optionally substituted heterocyclic group; preferably, the substituents on the groups which can be optionally substituted may be 1-4 groups selected from the following groups: $C_1$-$C_6$ alkyl and —$NR_aR_b$, wherein $R_a$ and $R_b$ are each independently H and $C_1$-$C_6$ alkyl; preferably, the heterocyclic group is selected from piperazinyl and piperidinyl.

In each of the foregoing embodiments in Formula II, the substituents on $Ar_2$ is selected from any one, two, three or four groups of the following groups: optionally substituted piperazinyl, optionally substituted piperidinyl, $C_1$-$C_6$ alkyl, halo, and $C_1$-$C_6$ alkoxy; preferably, the substituents on the optionally substituted group may be 1-4 groups selected from the following groups: $C_1$-$C_6$ alkyl and —$NR_aR_b$, wherein $R_a$ and $R_b$ are each independently H and $C_1$-$C_6$ alkyl.

In each of the foregoing embodiments in Formula II, the optionally substituted piperazinyl is the piperazinlyl which can be substituted by 1, 2 or 3 groups selected from: $C_1$-$C_6$ alkyl.

In each of the foregoing embodiments in Formula II, the piperazinyl has at least one substituent at the para-position, and optionally, one or two substituents at the meta-position.

In each of the foregoing embodiments in Formula II, the optionally substituted piperidinyl is the piperidinyl which can be substituted by 1 group selected from $C_1$-$C_6$ alkyl and —$NR_aR_b$, wherein $R_a$ and $R_b$ are each independently H and $C_1$-$C_6$ alkyl.

In each of the foregoing embodiments in Formula II, $Ar_2$ is selected from optionally substituted phenyl and optionally substituted tetrahydroisoquinolinyl.

In each of the foregoing embodiments in Formula II, $Ar_2$ is selected from phenyl substituted by piperazinyl which can be optionally substituted, phenyl substituted by pyridinyl which can be optionally substituted, and tetrahydroisoquinolinyl optionally substituted by 1-3 $C_1$-$C_6$ alkyl.

In each of the foregoing embodiments in Formula II, the piperazinyl is optionally substituted by 1-3 groups selected from $C_1$-$C_6$ alkyl.

In each of the foregoing embodiments in Formula II, the piperidinyl is optionally substituted by 1 group selected from $C_1$-$C_6$ alkyl and —$NR_aR_b$, wherein $R_a$ and $R_b$ are each independently H and $C_1$-$C_6$ alkyl.

In one or more of the foregoing embodiments, $R_4$ and $R_5$ are each independently H and optionally substituted $C_1$-$C_6$ alkyl, preferably, $R_4$ and $R_5$ are each independently H and optionally substituted $C_1$-$C_6$ alkyl.

In each of the foregoing embodiments, $R_1$ or $Ar_1$ is selected from

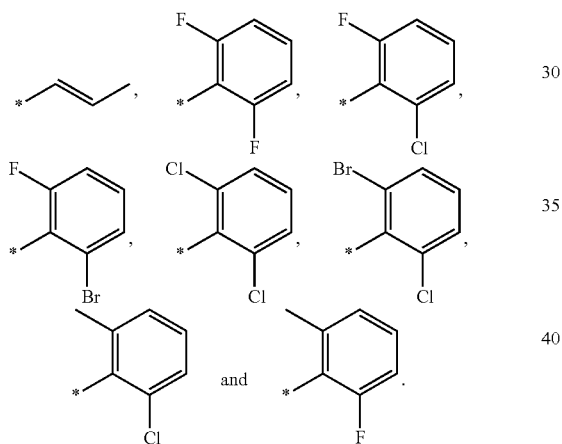

In each of the foregoing embodiments, $R_2$ or $Ar_2$ is selected from

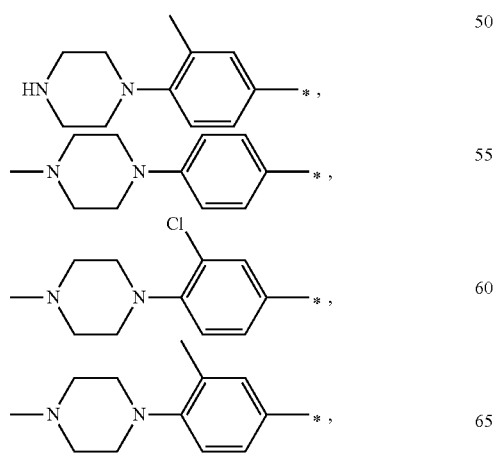

-continued

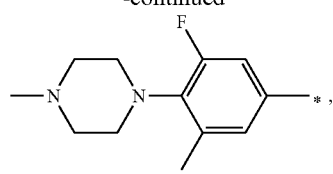

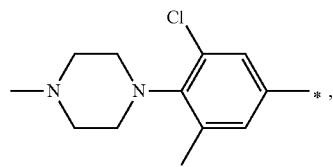

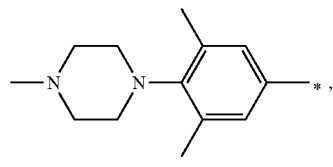

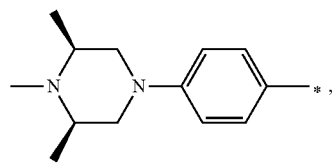

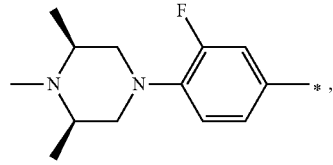

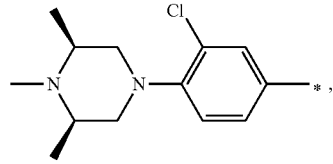

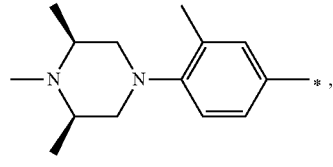

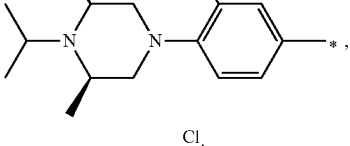

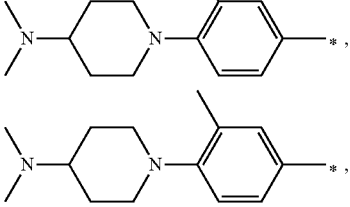

-continued
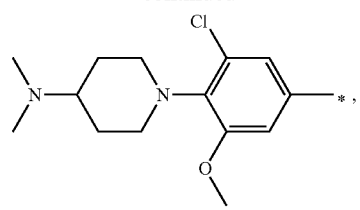
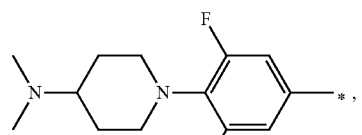
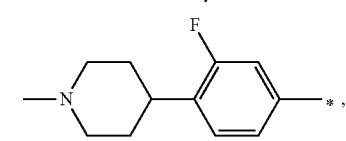
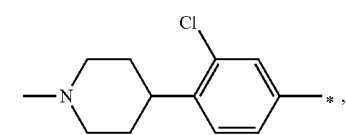
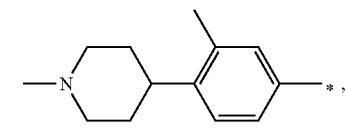
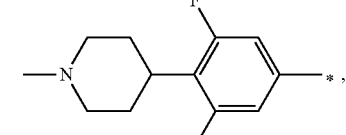
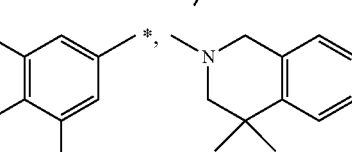
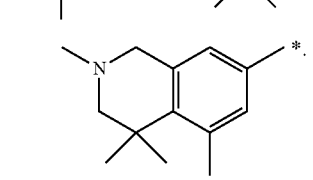
In each of the foregoing embodiments, $R_1$ or $Ar_1$ is selected from any group as the following:
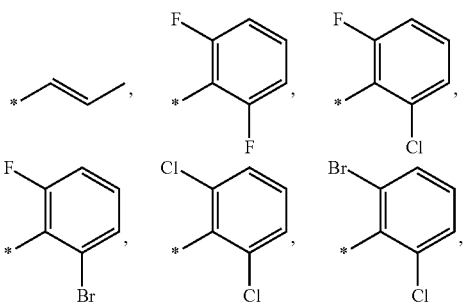
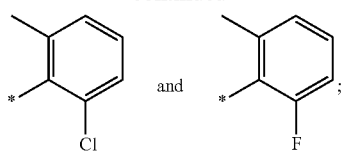
$R_2$ or $Ar_2$ is selected from any group as the following:
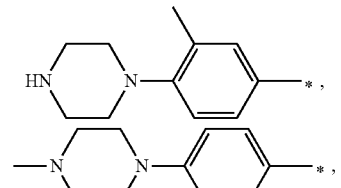
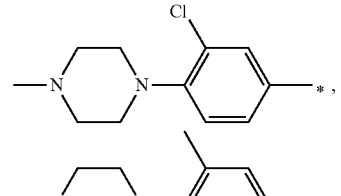
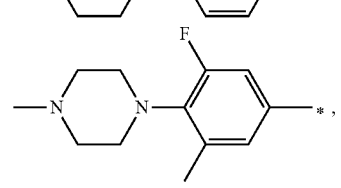
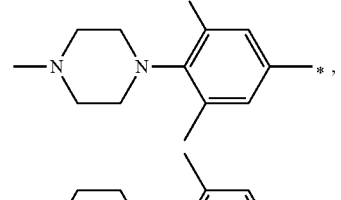
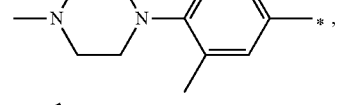
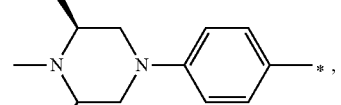
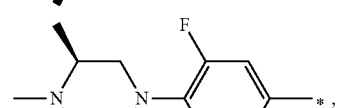
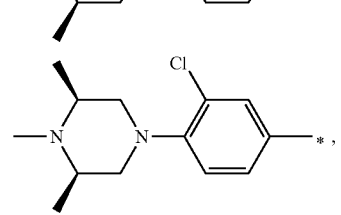

In each of the foregoing embodiments, compounds of Formula II have the structures represented by Formula III:

$$\text{III}$$

wherein,

Ar$_1$ is selected from phenyl substituted by 1 or 2 substituents selected from halo and C$_1$-C$_6$ alkyl; and Ar$_2$ is selected from substituted phenyl, of which the substituents are selected from: halo, C$_1$-C$_6$ alkyl and C$_1$-C$_6$ alkoxy; piperazinyl optionally substituted by 1-3 substituents selected from C$_1$-C$_6$ alkyl; piperidinyl optionally substituted by one substituent selected from C$_1$-C$_6$ alkyl and —NR$_a$R$_b$; and tetrahydroisoquinolinyl optionally substituted by 1-3 substituents selected from C$_1$-C$_6$ alkyl; wherein R$_a$ and R$_b$ are each independently H or C$_1$-C$_6$ alkyl.

In one or more embodiments, in Formula III,

Ar$_1$ is selected from phenyl substituted by 2 substituents selected from halo, and C$_1$-C$_6$ alkyl; and Ar$_2$ is selected from substituted phenyl, of which the substituents are selected from: halo, C$_1$-C$_6$ alkyl and C$_1$-C$_6$ alkoxy; piperazinyl optionally substituted by 1-3 substituents selected from C$_1$-C$_6$ alkyl; piperidinyl optionally substituted by one substituent selected from C$_1$-C$_6$ alkyl and —NR$_a$R$_b$; and tetrahydroisoquinolinyl optionally substituted by 1-3 substituents selected from C$_1$-C$_6$ alkyl; wherein R$_a$ and R$_b$ are each independently H or C$_1$-C$_6$ alkyl.

In one or more embodiments, in Formula III, Ar$_1$ is di-substituted phenyl substituted by substituents selected from halo and C$_1$-C$_3$ alkyl at two meta-positions, preferably, at least one of the two substituents is halo; Ar$_2$ is phenyl substituted by 1, 2 or 3 substituents selected from halo, C$_1$-C$_6$ alkyl and C$_1$-C$_6$ alkoxy; piperazinyl optionally substituted by 1-3 substituents selected from C$_1$-C$_6$ alkyl; piperidinyl substituted by 1 substituent selected from C$_1$-C$_6$ alkyl and —NR$_a$R$_b$; and tetrahydroisoquinolinyl substituted by 1-3 substituents selected from C$_1$-C$_6$ alkyl; wherein R$_a$ and R$_b$ are independently H and C$_1$-C$_4$ alkyl.

In each of the foregoing embodiments in Formula III, preferably, Ar$_1$ is selected from any group as the following:

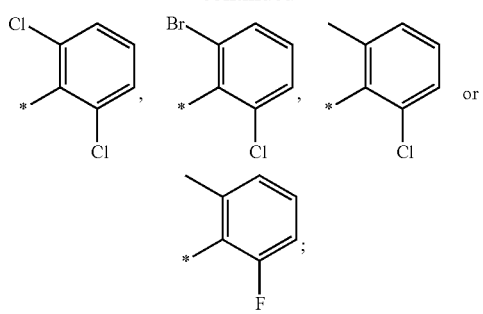
preferably, Ar$_2$ is selected from any group as the following:
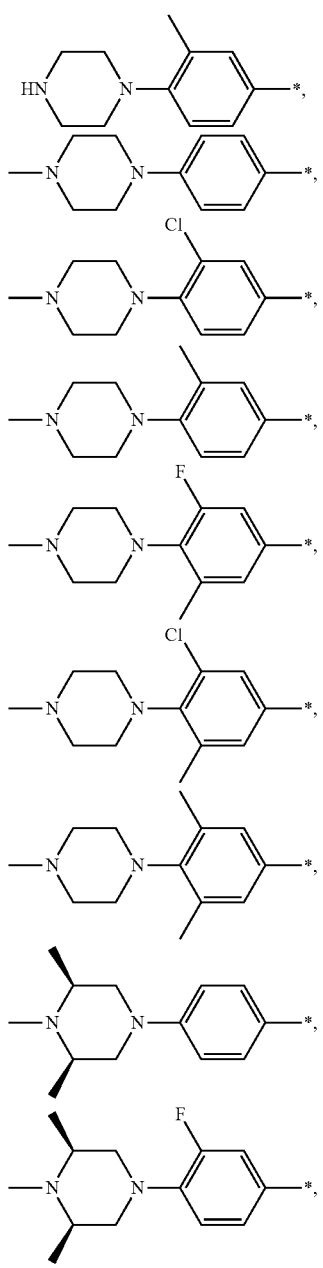
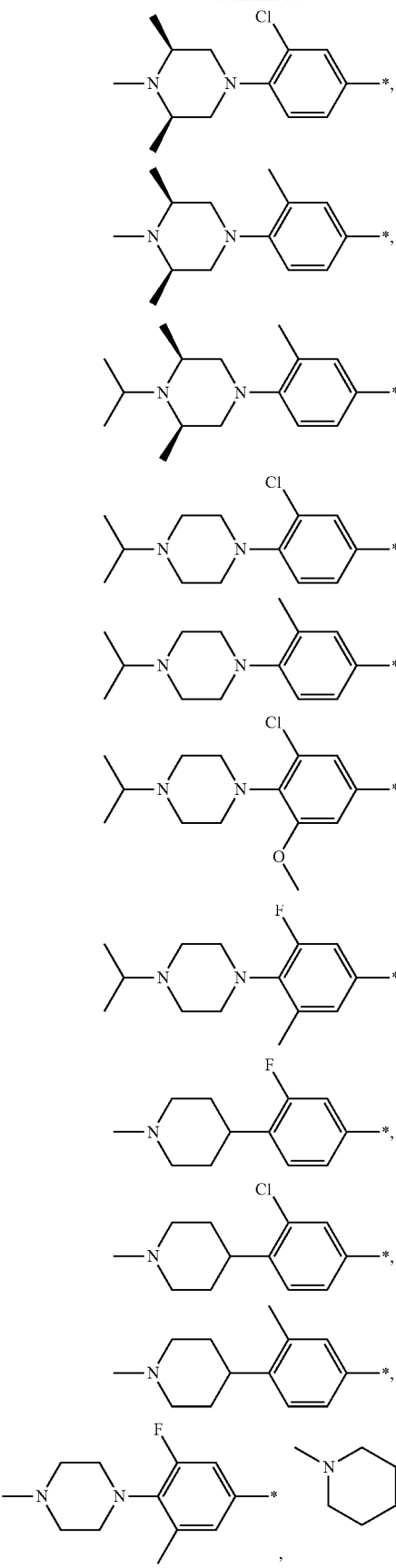

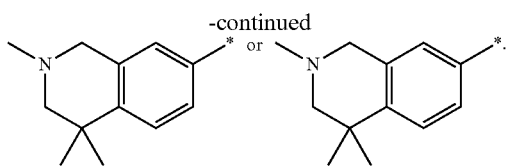

In each of the foregoing embodiments, preferred compounds of Formulae I, II and III include, without limitation:

6-(2,6-dichlorophenyl)-2-((4-(4-methylpiperazin-1-yl)phenyl)amino)imidazo[1,2-b]pyrimido[4,5-d]pyridazin-5(6H)-one (Example 1);

6-(2,6-difluorophenyl)-2-((3-methyl-4-(4-methylpiperazin-1-yl)phenyl)amino)imidazo[1,2-b]pyrimido[4,5-d]pyridazin-5(6H)-one (Example 2);

6-(2,6-dichlorophenyl)-2-((3-methyl-4-(4-methylpiperazin-1-yl)phenyl)amino)imidazo[1,2-b]pyrimido[4,5-d]pyridazin-5(6H)-one (Example 3);

6-(2,6-dichlorophenyl)-2-((3,5-dimethyl-4-(4-methylpiperazin-1-yl)phenyl)amino)imidazo[1,2-b]pyrimido[4,5-d]pyridazin-5(6H)-one (Example 4);

6-(2,6-dichlorophenyl)-2-((3-chloro-4-(4-methylpiperazin-1-yl)phenyl)amino)imidazo[1,2-b]pyrimido[4,5-d]pyridazin-5(6H)-one (Example 5);

6-(2,6-dichlorophenyl)-2-((3-chloro-5-methyl-4-(4-methylpiperazin-1-yl)phenyl)amino)imidazo[1,2-b]pyrimido[4,5-d]pyridazin-5(6H)-one (Example 6);

6-(2-chloro-6-fluorophenyl)-2-((4-(4-methylpiperazin-1-yl)phenyl)amino)imidazo[1,2-b]pyrimido[4,5-d]pyridazin-5(6H)-one (Example 7);

6-(2-chloro-6-fluorophenyl)-2-((3-chloro-4-(4-methylpiperazin-1-yl)phenyl)amino) imidazo[1,2-b]pyrimido[4,5-d]pyridazin-5(6H)-one (Example 8);

6-(2-chloro-6-fluorophenyl)-2-((3-methyl-4-(4-methylpiperazin-1-yl)phenyl)amino)imidazo[1,2-b]pyrimido[4,5-d]pyridazin-5(6H)-one (Example 9);

6-(2-chloro-6-fluorophenyl)-2-((3-chloro-5-methyl-4-(4-methylpiperazin-1-yl)phenyl)amino)imidazo[1,2-b]pyrimido[4,5-d]pyridazin-5(6H)-one (Example 10);

6-(2-chloro-6-fluorophenyl)-2-((3,5-dimethyl-4-(4-methylpiperazin-1-yl)phenyl)amino)imidazo[1,2-b]pyrimido[4,5-d]pyridazin-5(6H)-one (Example 11);

6-(2-chloro-6-fluorophenyl)-2-((2,4,4-trimethyl-1,2,3,4-tetrahydroisoquinolin-7-yl)amino)imidazo[1,2-b]pyrimido[4,5-d]pyridazin-5(6H)-one (Example 12);

6-(2,6-difluorophenyl)-2-((3,5-dimethyl-4-(4-methylpiperazin-1-yl)phenyl)amino)imidazo[1,2-b]pyrimido[4,5-d]pyridazin-5(6H)-one (Example 13);

6-(2-fluoro-6-methylphenyl)-2-((3-methyl-4-(4-methylpiperazin-1-yl)phenyl)amino)imidazo[1,2-b]pyrimido[4,5-d]pyridazin-5(6H)-one (Example 14);

6-(2-fluoro-6-methylphenyl)-2-((3,5-dimethyl-4-(4-methylpiperazin-1-yl)phenyl)amino) imidazo[1,2-b]pyrimido[4,5-d]pyridazin-5(6H)-one (Example 15);

6-(2-chloro-6-methylphenyl)-2-((3-methyl-4-(4-methylpiperazin-1-yl)phenyl)amino)imidazo[1,2-b]pyrimido[4,5-d]pyridazin-5(6H)-one (Example 16);

6-(2-chloro-6-methylphenyl)-2-((3,5-dimethyl-4-(4-methylpiperazin-1-yl)phenyl)amino)imidazo[1,2-b]pyrimido[4,5-d]pyridazin-5(6H)-one (Example 17);

6-(2,6-difluorophenyl)-2-((3-chloro-4-(4-methylpiperazin-1-yl)phenyl)amino)imidazo[1,2-b]pyrimido[4,5-d]pyridazin-5(6H)-one (Example 18);

6-(2,6-difluorophenyl)-2-((3-fluoro-5-methyl-4-(4-methylpiperazin-1-yl)phenyl)amino)imidazo[1,2-b]pyrimido[4,5-d]pyridazin-5(6H)-one (Example 19);

6-(2,6-difluorophenyl)-2-((3-chloro-5-methyl-4-(4-methylpiperazin-1-yl)phenyl)amino) imidazo[1,2-b]pyrimido[4,5-d]pyridazin-5(6H)-one (Example 20);

6-(2-chloro-6-fluorophenyl)-2-((3-chloro-4-(4-methylpiperazin-1-yl)phenyl)amino)imidazo[1,2-b]pyrimido[4,5-d]pyridazin-5(6H)-one (Example 21);

6-(2-chloro-6-fluorophenyl)-2-((3-fluoro-5-methyl-4-(4-methylpiperazin-1-yl)phenyl)amino)imidazo[1,2-b]pyrimido[4,5-d]pyridazin-5(6H)-one (Example 22);

6-(2-chloro-6-fluorophenyl)-2-((3-chloro-5-methyl-4-(4-methylpiperazin-1-yl)phenyl)amino)imidazo[1,2-b]pyrimido[4,5-d]pyridazin-5(6H)-one (Example 23);

6-(2-chloro-6-fluorophenyl)-2-((3-methyl-4-((3S,5R)-3,4,5-trimethylpiperazin-1-yl)phenyl)amino)imidazo[1,2-b]pyrimido[4,5-d]pyridazin-5(6H)-one (Example 24);

6-(2-chloro-6-fluorophenyl)-2-((3-fluoro-5-methyl-4-(4-(dimethylamino)piperidin-1-yl)phenyl)amino)imidazo[1,2-b]pyrimido[4,5-d]pyridazin-5(6H)-one (Example 25);

6-(2,6-dichlorophenyl)-2-((3-methyl-4-(piperazin-1-yl)phenyl)amino)imidazo[1,2-b]pyrimido[4,5-d]pyridazin-5(6H)-one (Example 26);

6-(2,6-dichlorophenyl)-2-((3-chloro-4-(4-methylpiperazin-1-yl)phenyl)amino)imidazo[1,2-b]pyrimido[4,5-d]pyridazin-5(6H)-one (Example 27);

6-(2,6-dichlorophenyl)-2-((3-fluoro-5-methyl-4-(4-methylpiperazin-1-yl)phenyl)amino)imidazo[1,2-b]pyrimido[4,5-d]pyridazin-5(6H)-one (Example 28);

6-(2,6-dichlorophenyl)-2-((3-chloro-5-methyl-4-(4-methylpiperazin-1-yl)phenyl)amino)imidazo[1,2-b]pyrimido[4,5-d]pyridazin-5(6H)-one (Example 29);

6-(2,6-dichlorophenyl)-2-((4-((3S,5R)-3,4,5-trimethylpiperazin-1-yl)phenyl)amino)imidazo[1,2-b]pyrimido[4,5-d]pyridazin-5(6H)-one (Example 30);

6-(2,6-dichlorophenyl)-2-((3-fluoro-4-((3S,5R)-3,4,5-trimethylpiperazin-1-yl)phenyl)amino)imidazo[1,2-b]pyrimido[4,5-d]pyridazin-5(6H)-one (Example 31);

6-(2,6-dichlorophenyl)-2-((3-chloro-4-((3S,5R)-3,4,5-trimethylpiperazin-1-yl)phenyl)amino)imidazo[1,2-b]pyrimido[4,5-d]pyridazin-5(6H)-one (Example 32);

6-(2,6-dichlorophenyl)-2-((3-methyl-4-((3S,5R)-3,4,5-trimethylpiperazin-1-yl)phenyl)amino)imidazo[1,2-b]pyrimido[4,5-d]pyridazin-5(6H)-one (Example 33);

6-(2,6-dichlorophenyl)-2-((3-methyl-4-((3S,5R)-4-isopropyl-3,5-dimethylpiperazin-1-yl)phenyl)amino)imidazo[1,2-b]pyrimido[4,5-d]pyridazin-5(6H)-one (Example 34);

6-(2,6-dichlorophenyl)-2-((3-chloro-4-(4-(dimethylamino)piperidin-1-yl)phenyl)amino)imidazo[1,2-b]pyrimido[4,5-d]pyridazin-5(6H)-one (Example 35);

6-(2,6-dichlorophenyl)-2-((3-methyl-4-(4-(dimethylamino)piperidin-1-yl)phenyl)amino)imidazo[1,2-b]pyrimido[4,5-d]pyridazin-5(6H)-one (Example 36);

6-(2,6-dichlorophenyl)-2-((3-fluoro-5-methyl-4-(4-(dimethylamino)piperidin-1-yl)phenyl)amino)imidazo[1,2-b]pyrimido[4,5-d]pyridazin-5(6H)-one (Example 37);

6-(2,6-dichlorophenyl)-2-((3-chloro-5-methoxy-4-(4-(dimethylamino)piperidin-1-yl)phenyl)amino)imidazo[1,2-b]pyrimido[4,5-d]pyridazin-5(6H)-one (Example 38);

6-(2,6-dichlorophenyl)-2-((3-fluoro-4-(1-methylpiperidin-4-yl)phenyl)amino)imidazo[1,2-b]pyrimido[4,5-d]pyridazin-5(6H)-one (Example 39);

6-(2,6-dichlorophenyl)-2-((3-chloro-4-(1-methylpiperidin-4-yl)phenyl)amino)imidazo[1,2-b]pyrimido[4,5-d]pyridazin-5(6H)-one (Example 40);

6-(2,6-dichlorophenyl)-2-((3-methyl-4-(1-methylpiperidin-4-yl)phenyl)amino)imidazo[1,2-b]pyrimido[4,5-d]pyridazin-5(6H)-one (Example 41);

6-(2,6-dichlorophenyl)-2-((3-fluoro-5-methyl-4-(1-methylpiperidin-4-yl)phenyl)amino)imidazo[1,2-b]pyrimido[4,5-d]pyridazin-5(6H)-one (Example 42);

6-(2,6-dichlorophenyl)-2-((2,4,4,4,5-tetramethyl-1,2,3,4-tetrahydroisoquinolin-7-yl)amino)imidazo[1,2-b]pyrimido[4,5-d]pyridazin-5(6H)-one (Example 43);

6-(2,6-dichlorophenyl)-2-((2,5-dimethyl-1,2,3,4-tetrahydroisoquinolin-7-yl)amino)imidazo[1,2-b]pyrimido[4,5-d]pyridazin-5(6H)-one (Example 44);

6-(2-bromo-6-fluorophenyl)-2-((3-methyl-4-(4-(dimethylamino)piperidin-1-yl)phenyl)amino)imidazo[1,2-b]pyrimido[4,5-d]pyridazin-5(6H)-one (Example 45);

6-(2-bromo-6-chlorophenyl)-2-((3-methyl-4-(4-methylpiperazin-1-yl)phenyl)amino)imidazo[1,2-b]pyrimido[4,5-d]pyridazin-5(6H)-one (Example 46);

6-(2-bromo-6-chlorophenyl)-2-((3-chloro-4-(4-methylpiperazin-1-yl)phenyl)amino)imidazo[1,2-b]pyrimido[4,5-d]pyridazin-5(6H)-one (Example 47);

6-(2-bromo-6-chlorophenyl)-2-((3-chloro-4-(dimethylamino)piperidin-1-yl)phenyl)amino)imidazo[1,2-b]pyrimido[4,5-d]pyridazin-5(6H)-one (Example 48);

6-(2-bromo-6-chlorophenyl)-2-((3-methyl-4-(4-(dimethylamino)piperidin-1-yl)phenyl)amino)imidazo[1,2-b]pyrimido[4,5-d]pyridazin-5(6H)-one (Example 49);

6-(2-bromo-6-chlorophenyl)-2-((3-fluoro-5-methyl-4-(4-(dimethylamino)piperidin-1-yl)phenyl)amino)imidazo[1,2-b]pyrimido[4,5-d]pyridazin-5(6H)-one (Example 50);

6-(2-fluoro-6-methylphenyl)-2-((3-chloro-4-(4-methylpiperazin-1-yl)phenyl)amino)imidazo[1,2-b]pyrimido[4,5-d]pyridazin-5(6H)-one (Example 51);

6-(2-fluoro-6-methylphenyl)-2-((3-chloro-5-methyl-4-(4-methylpiperazin-1-yl)phenyl)amino)imidazo[1,2-b]pyrimido[4,5-d]pyridazin-5(6H)-one (Example 52);

6-(2-chloro-6-methylphenyl)-2-((3-chloro-4-(4-methylpiperazin-1-yl)phenyl)amino)imidazo[1,2-b]pyrimido[4,5-d]pyridazin-5(6H)-one (Example 53);

6-(2-chloro-6-methylphenyl)-2-((3-fluoro-5-methyl-4-(4-methylpiperazin-1-yl)phenyl)amino)imidazo[1,2-b]pyrimido[4,5-d]pyridazin-5(6H)-one (Example 54);

6-(2-chloro-6-methylphenyl)-2-((3-chloro-5-methyl-4-(4-methylpiperazin-1-yl)phenyl)amino)imidazo[1,2-b]pyrimido[4,5-d]pyridazin-5(6H)-one (Example 55);

6-(2,6-dichlorophenyl)-2-((3-chloro-4-(4-methylpiperazin-1-yl)phenyl)amino)-8-methylimidazo[1,2-b]pyrimido[4,5-d]pyridazin-5(6H)-one (Example 56);

6-(2,6-dichlorophenyl)-2-((3-chloro-4-(4-methylpiperazin-1-yl)phenyl)amino)-9-methylimidazo[1,2-b]pyrimido[4,5-d]pyridazin-5(6H)-one (Example 57);

6-(2,6-dichlorophenyl)-2-((3-methyl-4-(4-(dimethylamino)piperidin-1-yl)phenyl)amino)-9-methylimidazo[1,2-b]pyrimido[4,5-d]pyridazin-5(6H)-one (Example 58);

6-(2,6-dichlorophenyl)-2-((3-fluoro-5-methyl-4-(4-(dimethylamino)piperidin-1-yl)phenyl)amino)-9-methylimidazo[1,2-b]pyrimido[4,5-d]pyridazin-5(6H)-one (Example 59);

6-(2,6-dichlorophenyl)-2-((3-methyl-4-(4-methylpiperazin-1-yl)phenyl)amino)-9-ethylimidazo[1,2-b]pyrimido[4,5-d]pyridazin-5(6H)-one (Example 60);

6-(2,6-dichlorophenyl)-2-((3-methyl-4-(4-(dimethylamino)piperidin-1-yl)phenyl)amino)-9-ethylimidazo[1,2-b]pyrimido[4,5-d]pyridazin-5(6H)-one (Example 61);

6-(2,6-dichlorophenyl)-2-((3-methyl-4-(4-(dimethylamino)piperidin-1-yl)phenyl)amino)-9-isopropylimidazo[1,2-b]pyrimido[4,5-d]pyridazin-5(6H)-one (Example 62);

6-(2,6-dichlorophenyl)-2-((3-methyl-4-(4-methylpiperazin-1-yl)phenyl)amino)-9-(hydroxymethyl)imidazo[1,2-b]pyrimido[4,5-d]pyridazin-5(6H)-one (Example 63);

6-allyl-2-((3-methyl-4-(4-(dimethylamino)piperidin-1-yl)phenyl)amino)imidazo[1,2-b]pyrimido[4,5-d]pyridazin-5(6H)-one (Example 64);

and pharmaceutically acceptable salts or prodrugs thereof.

The term "alkyl" as employed herein by itself or as part of another group refers to straight or branched chain radicals of up to ten carbons. Useful alkyl groups include straight-chained or branched $C_{1-10}$ alkyl groups, more preferably $C_{1-6}$ alkyl groups. In some embodiments, alkyl is $C_{1-4}$ alkyl. Typical $C_{1-10}$ alkyl groups include methyl, ethyl, propyl, isopropyl, butyl, sec-butyl, tert-butyl, 3-pentyl, hexyl and octyl groups, which may be optionally substituted.

The term "alkenyl" as employed herein means a straight or branched chain radical of 2-10 carbon atoms, unless the chain length is limited thereto, including at least one double bond between two of the carbon atoms in the chain; preferred $C_2$-$C_6$ alkenyl. Typical alkenyl groups include ethenyl, 1-propenyl, 2-propenyl, 2-methyl-1-propenyl, 1-butenyl and 2-butenyl.

The term "alkynyl" is used herein to mean a straight or branched chain radical of 2-10 carbon atoms, unless the chain length is limited thereto, wherein there is at least one triple bond between two of the carbon atoms in the chain; preferred $C_2$-$C_6$ alkynyl. Typical alkynyl groups include ethynyl, 1-propynyl, 1-methyl-2-propynyl, 2-propynyl, 1-butynyl and 2-butynyl.

Useful alkoxy groups include oxygen substituted by $C_{1-10}$ alkyl groups, preferred $C_1$-$C_6$ alkyl, mentioned above, for example, methoxy, ethoxy, etc. The alkyl in the alkoxy group may be optionally substituted. The substituents on alkoxy include, without limitation, halo, morpholino, amino including alkylamino and dialkylamino, and carboxy including esters thereof.

Useful alkylthio groups include sulfur substituted by $C_{1-10}$ alkyl groups, preferred $C_1$-$C_6$ alkyl, mentioned above. The alkyl in the alkylthio group may be optionally substituted. Also included are the sulfoxides and sulfones of such alkylthio groups.

Useful amino and optionally substituted amino groups include —$NH_2$, —NHR' and —NR'R", wherein R' and R" are optionally substituted $C_{1-10}$ alkyl, cycloalkyl, aryl, heteroaryl, or amino; or R' and R" are combined with the N to form a 5-8 membered heterocyclic ring structure, such as a piperidine; or R' and R" are combined with the N and an additional N or O atom to form a 5-8 membered heterocyclic ring, such as a piperazine. The alkyl and heterocyclic ring are optionally substituted.

Except as otherwise noted, the groups as described herein, such as alkyl, alkoxy, alkylthio, alkenyl, alkynyl, cycloalkyl, carbonyl, carbocyclic and heterocyclic groups, aryl, arylalkyl, arylalkenyl, arylalkynyl and heteroaryl and heteroarylalkyl groups, may be optionally substituted by one or more (such as 1, 2, 3, or 4) substituents selected from the group consisting of halo, hydroxy, carboxyl, amino, nitro, cyano, $C_1$-$C_6$ acylamino, $C_1$-$C_6$ acyloxy, $C_1$-$C_6$ alkoxy, aryloxy, alkylthio, $C_1$-$C_6$ alkyl, $C_1$-$C_6$ acyl, $C_6$-$C_{10}$ aryl, $C_3$-$C_8$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl($C_2$-$C_6$)alkynyl, saturated and unsaturated heterocyclic and heteroaryl, methylenedioxy, $C_1$-$C_6$ haloalkyl, $C_6$-$C_{10}$ aryl($C_1$-$C_6$)alkyl, $C_1$-$C_6$ hydroxyalkyl, ureido, thiol, azido, carbonyl, di($C_{1-10}$ alkyl)amino, alkylsulfonyl, aminosulfonyl, dialkylaminosulfonyl, and alkylsulfinyl, and the like. The substituent itself may also be optionally substituted.

Except as otherwise noted, when substituted, preferably, substituents on the alkyl, alkoxy, alkylthio, alkenyl, alkynyl, cycloalkyl, carbonyl, carbocyclic and heterocyclic groups may be one or more (such as 1, 2, 3, or 4) groups selected from the group consisting of halo, hydroxy, carboxyl, amino, nitro, cyano, $C_1$-$C_6$ acylamino, $C_1$-$C_6$ acyl, $C_1$-$C_6$ acyloxy, $C_1$-$C_6$ alkoxy, aryloxy, alkylthio, $C_6$-$C_{10}$ aryl, $C_3$-$C_8$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl($C_2$-$C_6$)alkynyl, saturated and unsaturated heterocyclic and heteroaryl.

Except as otherwise noted, when substituted, substituents on the aryl, arylalkyl, arylalkenyl, arylalkynyl, heteroaryl and heteroarylalkyl groups may be one or more (such as 1, 2, 3, or 4) groups selected from the group consisting of halo, methylenedioxy, $C_1$-$C_6$ haloalkyl, $C_6$-$C_{10}$ aryl, $C_3$-$C_8$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl, nitro, amino, ureido, cyano, $C_1$-$C_6$ acylamino, hydroxy, thiol, $C_1$-$C_6$ acyloxy, azido, $C_1$-$C_6$ alkoxy, carbonyl, carboxy, di($C_1$-$C_{10}$ alkyl)amino, alkylsulfonyl, aminosulfonyl, dialkylaminosulfonyl, and alkylsulfinyl.

It should be understood that in each embodiment, when the substituent is heterocyclic, aryl or heteroaryl, the number of heterocyclic, aryl or hetararyl substituents is usually 1.

The term "aryl" as employed herein by itself or as part of another group refers to monocyclic, bicyclic or tricyclic aromatic groups containing from 6 to 14 carbons in the ring portion.

Useful aryl groups include $C_6$-$C_{14}$ aryl, preferably $C_6$-$C_{10}$ aryl. Typical $C_6$-$C_{14}$ aryl groups include phenyl, naphthyl, phenanthrenyl, anthracenyl, indenyl, azulenyl, biphenyl, biphenylenyl and fluorenyl groups.

The term "carbocycle" as employed herein include cycloalkyl and partially saturated carbocyclic groups. Useful cycloalkyl groups are $C_3$-$C_8$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluoro, chloro, bromo and iodo.

The term "arylalkyl" is used herein to mean any of the above-mentioned $C_1$-$C_{10}$ alkyl groups substituted by any of the above-mentioned $C_6$-$C_{14}$ aryl groups. Preferably the arylalkyl group is benzyl, phenethyl or naphthylmethyl.

The term "arylalkenyl" is used herein to mean any of the above-mentioned $C_2$-$C_{10}$ alkenyl groups substituted by any of the above-mentioned $C_6$-$C_{14}$ aryl groups.

The term "arylalkynyl" is used herein to mean any of the above-mentioned $C_2$-$C_{10}$ alkynyl groups substituted by any of the above-mentioned $C_6$-$C_{14}$ aryl groups.

The term "aryloxy" is used herein to mean oxygen substituted by one of the above-mentioned $C_6$-$C_{14}$ aryl groups, which may be optionally substituted. Useful aryloxy groups include phenoxy and 4-methylphenoxy.

The term "arylalkoxy" is used herein to mean any of the above mentioned $C_1$-$C_{10}$ alkoxy groups substituted by any of the above-mentioned aryl groups, which may be optionally substituted. Useful arylalkoxy groups include benzyloxy and phenethyloxy.

Useful haloalkyl groups include $C_1$-$C_{10}$ alkyl, or preferably $C_1$-$C_6$ alkyl substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_1$-$C_6$ acyl (alkanoyl) attached to an amino nitrogen, e.g., acetamido, chloroacetamido, propionamido, butanoylamido, pentanoylamido and hexanoylamido, as well as aryl-substituted $C_1$-$C_6$ acylamino groups, e.g., benzoylamido, and pentafluorobenzoylamido. Usefule acyl includes $C_1$-$C_6$ acyl, such as acetyl.

Useful acyloxy groups are any $C_1$-$C_6$ acyl (alkanoyl) attached to an oxy (—O—) group, e.g., formyloxy, acetoxy, propionoyloxy, butanoyloxy, pentanoyloxy and hexanoyloxy.

The term heterocycle (heterocyclic group) is used herein to mean a saturated or partially saturated 3-7 membered monocyclic, or 7-10 membered bicyclic ring system, which consists of carbon atoms and one to four heteroatoms independently selected from the group consisting of O, N, and S, wherein the nitrogen and sulfur heteroatoms can be optionally oxidized, and the nitrogen can be optionally quaternized. The term also includes any bicyclic group in which any of the above-defined heterocyclic rings is fused to a benzene ring. The heterocyclic ring of heterocycle can be substituted on carbon or on a nitrogen atom if the resulting compound is stable.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetrahydroisoquinolinyl, tetronoyl and tetramoyl groups, which are optionally substituted.

The term "heteroaryl" as employed herein refers to groups having 5 to 14 ring atoms; 6, 10 or 14 π electrons shared in a cyclic array; and containing, as ring atom, carbon atoms and 1-3 heteroatoms selected from oxygen, nitrogen and sulfur.

Useful heteroaryl groups include thienyl (thiophenyl), benzo[d]isothiazol-3-yl, benzo[b]thienyl, naphtho[2,3-b]thienyl, thianthrenyl, furyl (furanyl), pyranyl, isobenzofuranyl, chromenyl, xanthenyl, phenoxathiinyl, pyrrolyl, imidazolyl, pyrazolyl, pyridyl (pyridinyl, including without limitation 2-pyridyl, 3-pyridyl, and 4-pyridyl), pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, (3-carbolinyl, phenanthridinyl, acridinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-amino-isocoumarin, pyrido[1,2-a]pyrimidin-4-one, tetrahydrocyclopenta[c]pyrazol-3-yl, pyrazolo[1,5-a]pyrimidinyl, benzoisoxazolyl such as 1,2-benzoisoxazol-3-yl, benzimidazolyl, 2-oxindolyl, thiadiazolyl, and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "heteroaryloxy" is used herein to mean oxygen substituted by one of the above-mentioned heteroaryl groups, which may be optionally substituted. Useful heteroaryloxy groups include pyridyloxy, pyrazinyloxy, pyrrolyloxy, pyrazolyloxy, imidazolyloxy and thiophenyloxy.

The term "heteroarylalkoxy" is used herein to mean any of the above-mentioned $C_1$-$C_{10}$ alkoxy groups substituted by any of the above-mentioned heteroaryl groups, which may be optionally substituted.

Some of the compounds of the present disclosure may exist as stereoisomers including optical isomers. The disclosure includes all stereoisomers and both the racemic mixtures of such stereoisomers as well as the individual enantiomers that may be separated according to methods that are well known to those of ordinary skill in the art.

Examples of pharmaceutically acceptable salts include inorganic and organic acid salts, such as hydrochloride, hydrobromide, phosphate, sulphate, citrate, lactate, tartrate, maleate, fumarate, mandelate and oxalate; and inorganic and organic base salts with bases, such as sodium hydroxy, tris(hydroxymethyl)aminomethane (TRIS, tromethane) and N-methyl-glucamine.

Examples of prodrugs of the compounds of the disclosure include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (*J. Med. Chem.* 42:3623-3628 (1999)) and Greenwald, et al., (*J. Med. Chem.* 42:3657-3667 (1999)); and acetals and ketals of alcohol containing compounds (e.g., those obtained by condensation with chloromethyl methyl ether or chloromethyl ethyl ether according to methods known in the art).

The compounds of this disclosure may be prepared using methods known to those skilled in the art, or the novel methods of this disclosure. Specifically, the compounds of this disclosure with Formula I can be prepared as illustrated by the exemplary reaction in Scheme 1. Reaction of N-tert-butoxycarbonyl-2-aminoacetaldehyde, (2,6-dichlorophenyl)hydrazine and sodium triacetoxyborohydride in dichloromethane (DCM) at room temperature and subsequent reaction with addition of sodium cyanoborohydrate produced tert-butyl (2-(2-(2,6-dichlorophenyl)hydrazinyl)ethyl)carbamate. Reaction of tert-butyl (2-(2-(2,6-dichlorophenyl)hydrazinyl)ethyl)carbamate, N,N-diisopropylethylamine (DIPEA) and benzyl chloroformate in DCM at room temperature produced benzyl 1-(2-((tert-butoxycarbonyl)amino)ethyl)-2-(2,6-dichlorophenyl)hydrazine-1-carboxylate. The solution of benzyl 1-(2-((tert-butoxycarbonyl)amino)ethyl)-2-(2,6-dichlorophenyl)hydrazine-1-carboxylate in dioxane solution of hydrochloric acid reacted at room temperature produced benzyl 1-(2-aminoethyl)-2-(2,6-dichlorophenyl)hydrazine-1-carboxylate hydrochloride. Reaction of benzyl 1-(2-aminoethyl)-2-(2,6-dichlorophenyl)hydrazine-1-carboxylate hydrochloride, DIPEA and 5-bromo-2-(methylthio)pyrimidine-4-carbonyl chloride in N,N-dimethylformamide (DMF) at 0° C. produced benzyl 1-(2-(2-methylthio-5-bromopyrimidine-4-carboxamido)ethyl)-2-(2,6-dichlorophenyl)hydrazine-1-carboxylate. Heating reaction of benzyl 1-(2-(2-methylthio-5-bromopyrimidine-4-carboxamido)ethyl)-2-(2,6-dichlorophenyl)hydrazine-1-carboxylate dissolved in trifluoroacetic acid (TFA) produced 2-methylthio-5-bromo-N-(2-(2-(2,6-dichlorophenyl)hydrazinyl)ethyl)-pyrimidine-4-carboxamide. Reaction of 2-methylthio-5-bromo-N-(2-(2-(2,6-dichlorophenyl)hydrazinyl)ethyl)pyrimidine-4-carboxamide and phosphorus pentachloride ($PCl_5$) in DCM at room temperature produced 2-(2-methylthio-5-bromopyrimidin-4-yl)-N-(2,6-dichlorophenyl)-4,5-dihydro-1H-imidazol-1-amine. Heating reaction of 2-(2-methylthio-5-bromopyrimidin-4-yl)-N-(2,6-dichlorophenyl)-4,5-dihydro-1H-imidazol-1-amine and copper cyanide in DMF produced 2-(2-methylthio-5-cyanopyrimidin-4-yl)-N-(2,6-dichlorophenyl)-1H-imidazol-1-amine. Heating reaction of 2-(2-methylthio-5-cyanopyrimidin-4-yl)-N-(2,6-dichlorophenyl)-1H-imidazol-1-amine in dioxane solution of hydrochloric acid produced 2-methylthio-6-(2,6-dichlorophenyl)imidazo[1,2-b]pyrimido[4,5-d]pyridazin-5(6H)-one. Reaction of 2-methylthio-6-(2,6-dichlorophenyl)imidazo[1,2-b]pyrimido[4,5-d]pyridazin-5(6H)-one and meta-chloroperbenzoic acid (m-CPBA) in DCM at room temperature produced the crude intermediates 2-methylsulfinyl-6-(2,6-dichlorophenyl)imidazo[1,2-b]pyrimido[4,5-d]pyridazin-5(6H)-one and 2-methylsulfonyl-6-(2,6-dichlorophenyl)imidazo[1,2-b]pyrimido[4,5-d]pyridazin-5(6H)-one. Reaction of the crude intermediates, 4-(4-methylpiperazin-1-yl)aniline and TFA in acetonitrile at room temperature produced the targeted compound 6-(2,6-dichlorophenyl)-2-((4-(4-methylpiperazin-1-yl)phenyl)amino)imidazo[1,2-b]pyrimido[4,5-d]pyridazin-5(6H)-one.

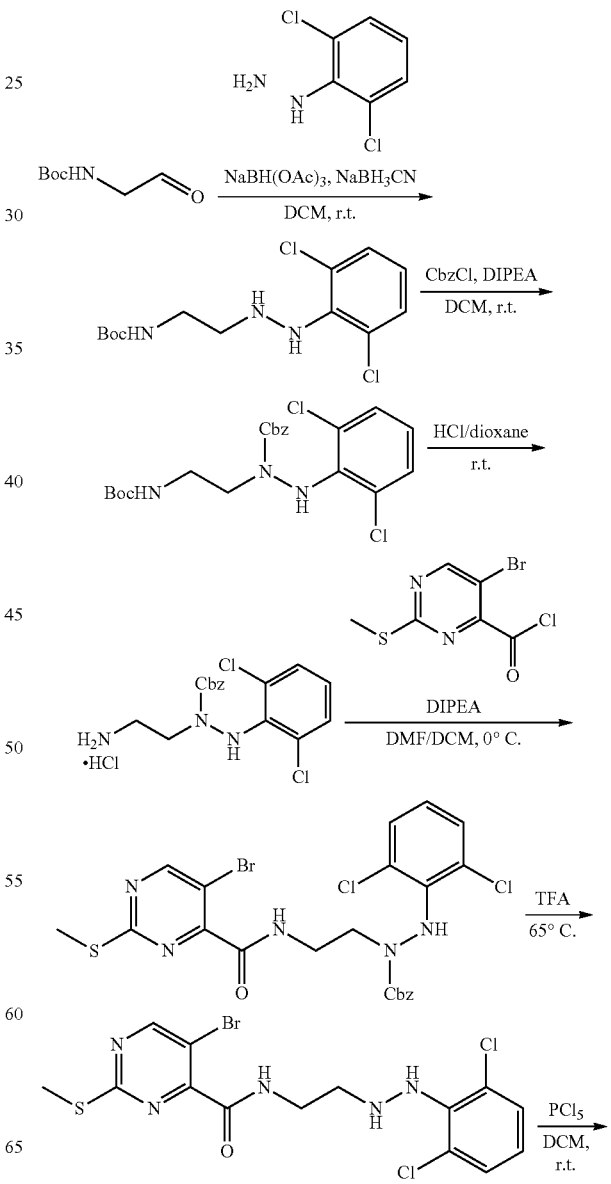

Scheme 1

-continued

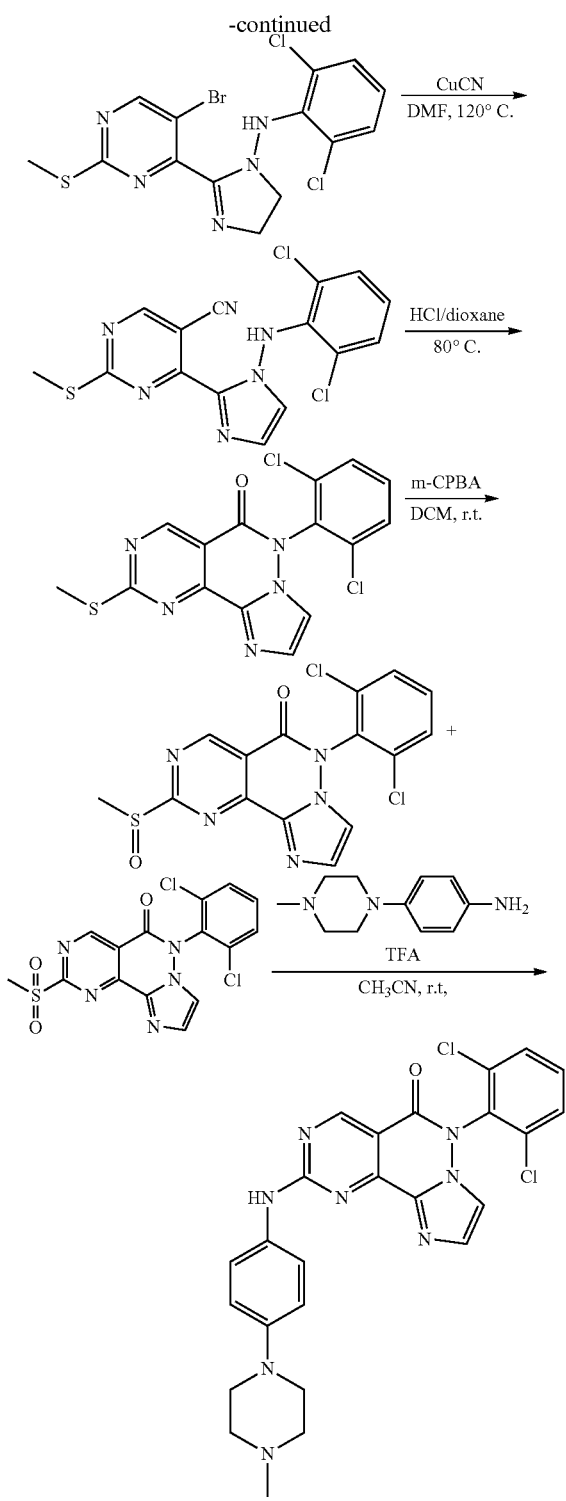

Other related compounds can be prepared similarly. For example, replacement of N-tert-butoxycarbonyl-2-aminoacetaldehyde with tert-butyl (1-oxobutyl-2-yl)carbamate produced the targeted compound 6-(2,6-dichlorophenyl)-2-((3-methyl-4-(4-methylpiperazin-1-yl)phenyl)amino)-9-ethyl-imidazo[1,2-b]pyrimido[4,5-d]pyridazin-5(6H)-one. Replacement of N-tert-butoxycarbonyl-2-aminoacetaldehyde with tert-butyl (3-methyl-1-oxobutan-2-yl)carbamate produced the targeted compound 6-(2,6-dichlorophenyl)-2-((3-methyl-4-(4-(dimethylamino)piperidin-1-yl)phenyl)amino)-9-isopropylimidazo[1,2-b]pyrimido[4,5-d]pyridazin-5(6H)-one.

Compounds of this disclosure can be prepared as illustrated by the exemplary reaction in Scheme 2. Heating reaction of 2-(methylthio)-5-bromopyrimidine-4-carboxylic acid and N,N'-carbonyldiimidazole in tetrahydrofuran, with the addition of 2,2-dimethoxyethan-1-amine reacted at room temperature produced N-(2,2-dimethoxyethyl)-2-(methylthio)-5-bromopyrimidine-4-carboxamide. Heating reaction of N-(2,2-dimethoxyethyl)-2-(methylthio)-5-bromopyrimidine-4-carboxamide and diluted hydrochloric acid in acetone produced N-(2-oxoethyl)-2-(methylthio)-5-bromopyrimidine-4-carboxamide. N-(2-oxoethyl)-2-(methylthio)-5-bromopyrimidine-4-carboxamide, (2,6-difluorophenyl)hydrazine and acetic acid in methanol reacted at room temperature, followed by addition of sodium cyanoborohydride, and the mixture reacted at room temperature produced N-(2-(2-(2,6-difluorophenyl)hydrazinyl)ethyl)-2-(methylthio)-5-bromopyrimidine-4-carboxamide. Reaction of N-(2-(2-(2,6-difluorophenyl)hydrazinyl)ethyl)-2-(methylthio)-5-bromopyrimidine-4-carboxamide and $PCl_5$ in anhydrous DCM at room temperature produced N-(2,6-dichlorophenyl)-2-(2-(methylthio)-5-bromopyrimidin-4-yl)-4,5-dihydro-1H-imidazol-1-amine. Reaction of N-(2,6-dichlorophenyl)-2-(2-(methylthio)-5-bromopyrimidin-4-yl)-4,5-dihydro-1H-imidazol-1-amine and manganese dioxide in DCM at room temperature produced N-(2,6-difluorophenyl)-2-(2-(methylthio)-5-bromopyrimidin-4-yl)-1H-imidazol-1-amine. Heating reaction of N-(2,6-difluorophenyl)-2-(2-(methylthio)-5-bromopyrimidin-4-yl)-1H-imidazol-1-amine and cuprous cyanide in 1,4-dioxane produced 2-(methylthio)-4-(1-((2,6-difluorophenyl)amino)-1H-imidazol-2-yl)pyrimidine-5-carbonitrile. Heating reaction of 2-(methylthio)-4-(1-((2,6-difluorophenyl)amino)-1H-imidazol-2-yl)pyrimidine-5-carbonitrile and dioxane solution of hydrochloric acid, followed by addition of water, and reacted under heating produced 2-(methylthio)-6-(2,6-difluorophenyl)imidazo[1,2-b]pyrimido[4,5-d]pyridazin-5(6H)-one. Reaction of 2-(methylthio)-6-(2,6-difluorophenyl)imidazo[1,2-b]pyrimido[4,5-d]pyridazin-5(6H)-one and meta-chloroperbenzoic acid (m-CPBA) in anhydrous DCM at room temperature produced the crude intermediates, and reaction of the crude intermediates, 3-methyl-4-(4-methylpiperazin-1-yl)aniline and TFA in acetonitrile at room temperature produced the targeted compound 6-(2,6-difluorophenyl)-2-((3-methyl-4-(4-methylpiperazin-1-yl)phenyl) amino)imidazo[1,2-b]pyrimido[4,5-d]pyridazin-5(6H)-one.

Scheme 2

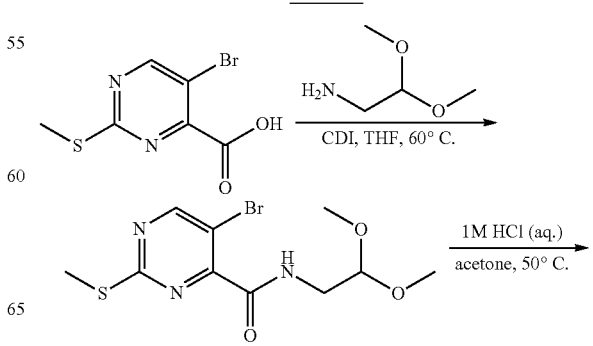

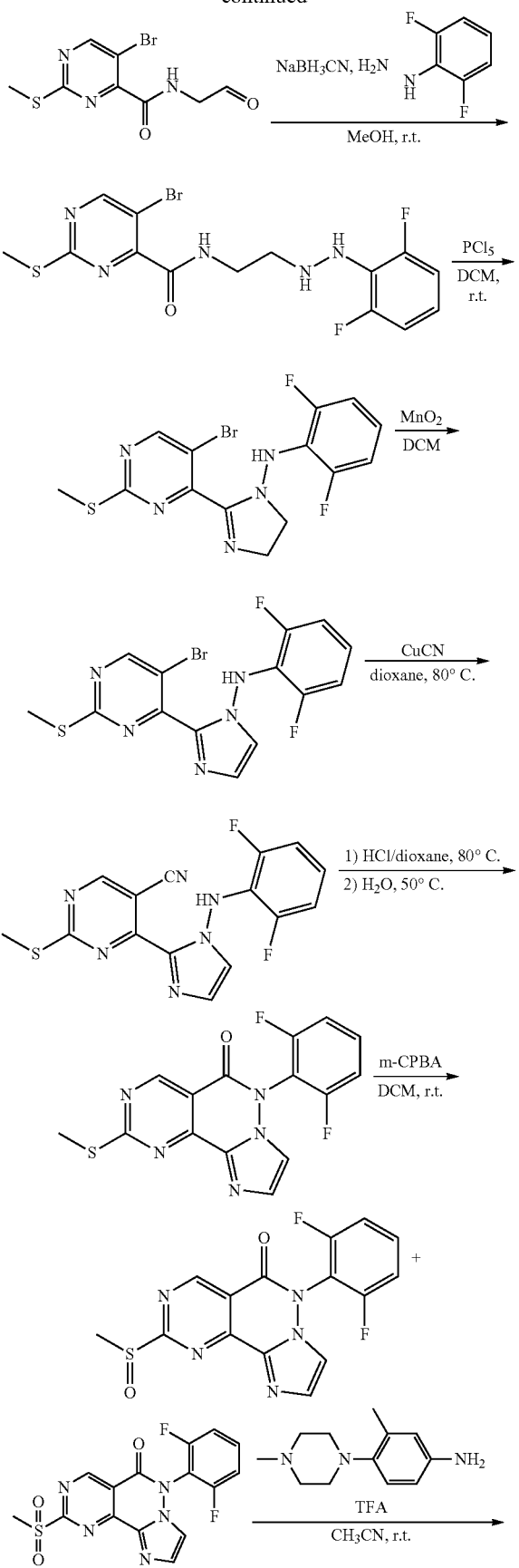

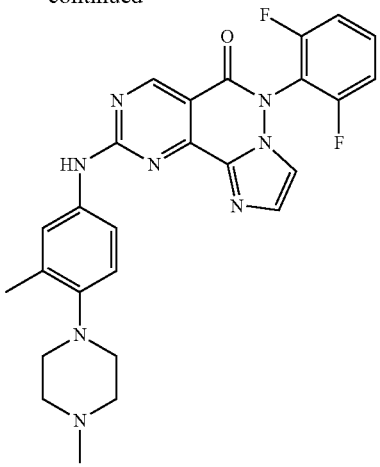

Other related compounds can be prepared similarly. For example, replacement of (2,6-difluorophenyl)hydrazine with (2,6-dichlorophenyl)hydrazine produced the targeted compound 6-(2,6-dichlorophenyl)-2-((3-methyl-4-(4-methylpiperazin-1-yl)phenyl)amino)imidazo[1,2-b]pyrimido[4,5-d]pyridazin-5(6H)-one. Replacement of (2,6-difluorophenyl)hydrazine with 2-chloro-6-fluorophenylhydrazine produced the targeted compound 6-(2-chloro-6-fluorophenyl)-2-((3-methyl-4-(4-methylpiperazin-1-yl)phenyl)amino)imidazo[1,2-b]pyrimido[4,5-d]pyridazin-5(6H)-one. Replacement of (2,6-difluorophenyl)hydrazine with 2-fluoro-6-methylphenylhydrazine produced the targeted compound 6-(2-fluoro-6-methylphenyl)-2-((3-methyl-4-(4-methylpiperazin-1-yl)phenyl)amino)imidazo[1,2-b]pyrimido[4,5-d]pyridazin-5(6H)-one. Replacement of 3-methyl-4-(4-methylpiperazin-1-yl)aniline with 2,4,4-trimethyl-1,2,3,4-tetrahydroisoquinolin-7-amine produced the targeted compound 6-(2-chloro-6-fluorophenyl)-2-((2,4,4-trimethyl-1,2,3,4-tetrahydroisoquinolin-7-yl)amino)imidazo[1,2-b]pyrimido[4,5-d]pyridazin-5(6H)-one. Replacement of 3-methyl-4-(4-methylpiperazin-1-yl)aniline with 4-((3S,5R)-3,4,5-trimethylpiperazin-1-yl)aniline produced the targeted compound 6-(2,6-dichlorophenyl)-2-((4-((3S,5R)-3,4,5-trimethylpiperazin-1-yl)phenyl)amino)imidazo[1,2-b]pyrimido[4,5-d]pyridazin-5(6H)-one. Replacement of 3-methyl-4-(4-methylpiperazin-1-yl)aniline with 3-chloro-4-(4-(dimethylamino)piperidin-1-yl)aniline produced the targeted compound 6-(2,6-dichlorophenyl)-2-((3-chloro-4-(4-(dimethylamino)piperidin-1-yl)phenyl)amino)imidazo[1,2-b]pyrimido[4,5-d]pyridazin-5(6H)-one. Replacement of 3-methyl-4-(4-methylpiperazin-1-yl)aniline with 3-fluoro-4-(1-methylpiperidin-4-yl) aniline produced the targeted compound 6-(2,6-dichlorophenyl)-2-((3-fluoro-4-(1-methylpiperidin-4-yl)phenyl)amino)imidazo[1,2-b]pyrimido[4,5-d]pyridazin-5 (6H)-one.

Compounds of this disclosure can be prepared as illustrated by the exemplary reaction in Scheme 3. 2-(Methylthio)-5-(ethoxycarbonyl)pyrimidine-4-carboxylic acid and 2-(7-azabenzotriazol-1-yl)-N,N,N',N'-tetramethyluronium hexafluorophosphate (HATU) reacted in DMF at room temperature, then 2,2-dimethoxyethan-1-amine was added, and the mixture was reacted at room temperature produced ethyl 2-(methylthio)-4-((2,2-dimethoxyethyl)carbamoyl)pyrimidine-5-carboxylate. Heating reaction of ethyl 2-(methylthio)-4-((2,2-dimethoxyethyl)carbamoyl)pyrimidine-5-carboxylate and concentrated hydrochloric acid produced ethyl 2-(methylthio)-4-((2-oxoethyl)carbamoyl)pyrimidine-5-carboxylate. Ethyl 2-(methylthio)-4-((2-oxoethyl)carbamoyl)pyrimidine-5-carboxylate and (2-bromo-6-chlorophenyl)hydrazine reacted in methanol, and then sodium cyanoborohydride was added for further reaction to produce ethyl 2-(methylthio)-4-((2-(2-(2-bromo-6-chlorophenyl)hydrazinyl)ethyl)carbamoyl)pyrimidine-5-carboxylate. Reaction of ethyl 2-(methylthio)-4-((2-(2-(2-bromo-6-chlorophenyl)hydrazinyl)ethyl)carbamoyl)pyrimidine-5-carboxylate and PCl$_5$ in DCM at room temperature produced ethyl 2-(methylthio)-4-(1-((2-bromo-6-chlorophenyl)amino)-4,5-dihydro-1H-imidazol-2-yl)pyrimidine-5-carboxylate. Heating reaction of ethyl 2-(methylthio)-4-(1-((2-bromo-6-chlorophenyl)amino)-4,5-dihydro-1H-imidazol-2-yl)pyrimidine-5-carboxylate and manganese dioxide in 1,4-dioxane produced ethyl 2-(methylthio)-4-(1-((2-bromo-6-chlorophenyl)amino)-1H-imidazol-2-yl)pyrimidine-5-carboxylate. Reaction of ethyl 2-(methylthio)-4-(1-((2-bromo-6-chlorophenyl)amino)-1H-imidazol-2-yl)pyrimidine-5-carboxylate and 1,8-Diazabicyclo[5.4.0]undec-7-ene (DBU) in DCM at 0° C. produced 2-(methylthio)-6-(2-bromo-6-chlorophenyl)imidazo[1,2-b]pyrimido[4,5-d]pyridazin-5(6H)-one. Reaction of 2-(methylthio)-6-(2-bromo-6-chlorophenyl)imidazo[1,2-b]pyrimido[4,5-d]pyridazin-5(6H)-one and m-CPBA in DCM at room temperature produced the crude intermediates, and reaction of the crude intermediates, 3-methyl-4-(4-methylpiperazin-1-yl)aniline and TFA in acetonitrile at room temperature produced 6-(2-bromo-6-chlorophenyl)-2-((3-methyl-4-(4-methylpiperazin-1-yl)phenyl)amino)imidazo[1,2-b]pyrimido[4,5-d]pyridazin-5(6H)-one.

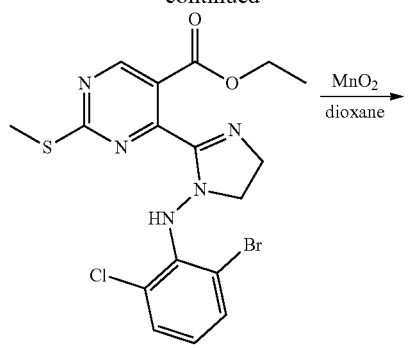

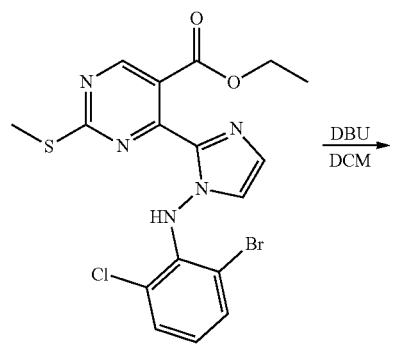

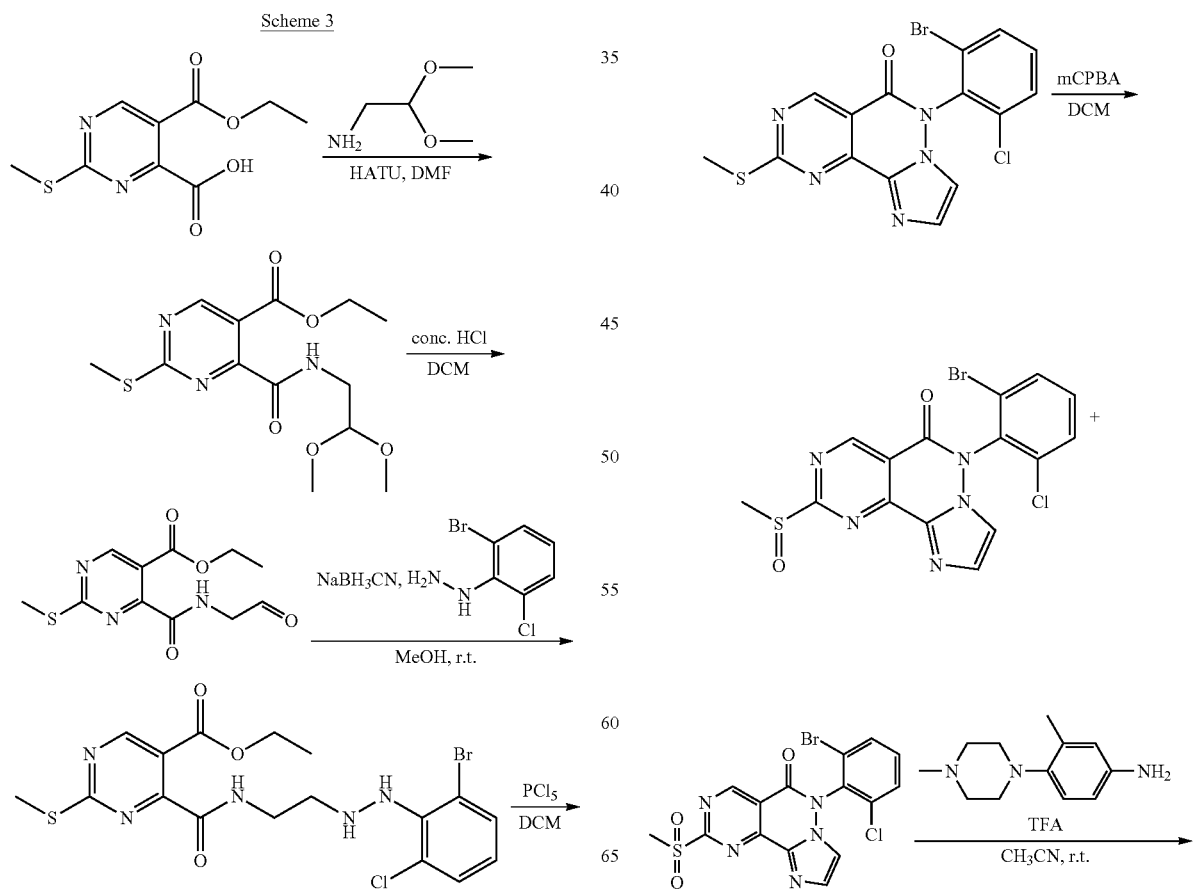

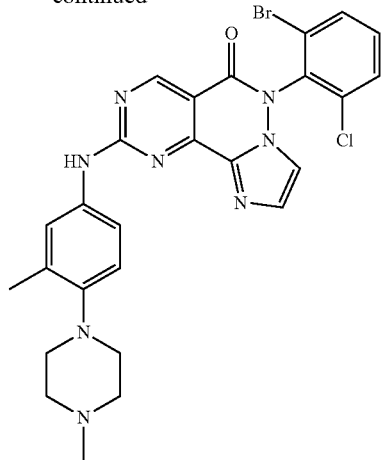

Other related compounds can be prepared similarly. For example, replacement of 3-methyl-4-(4-methylpiperazin-1-yl)aniline with 3-chloro-4-(4-methylpiperazin-1-yl)aniline produced the targeted compound 6-(2-bromo-6-chlorophenyl)-2-((3-chloro-4-(4-methylpiperazin-1-yl)phenyl)amino)imidazo[1,2-b]pyrimido[4,5-d]pyridazin-5(6H)-one. Replacement of 3-methyl-4-(4-methylpiperazin-1-yl)aniline with 3-chloro-4-(4-(dimethylamino)piperidin-1-yl)aniline produced the targeted compound 6-(2-bromo-6-chlorophenyl)-2-((3-chloro-4-(4-(dimethylamino)piperidin-1-yl)phenyl)amino)imidazo[1,2-b]pyrimido[4,5-d]pyridazin-5(6H)-one. Replacement of 3-methyl-4-(4-methylpiperazin-1-yl)aniline with 3-fluoro-5-methyl-4-(4-(dimethylamino)piperidin-1-yl)aniline produced the targeted compound 6-(2-bromo-6-chlorophenyl)-2-((3-fluoro-5-methyl-4-(4-(dimethylamino)piperidin-1-yl)phenyl)amino)imidazo[1,2-b]pyrimido[4,5-d]pyridazin-5(6H)-one.

Compounds of this disclosure can be prepared as illustrated by the exemplary reaction in Scheme 4. Reaction of 5-bromo-2-(methylthio)pyrimidine-4-carboxylic acid, DIPEA, HATU and 1-aminopropan-2-one hydrochloride in DMF at room temperature produced 5-bromo-2-(methylthio)-N-(2-oxopropyl)pyrimidine-4-carboxamide. Reaction of 5-bromo-2-(methylthio)-N-(2-oxopropyl)pyrimidine-4-carboxamide, (2,6-dichlorophenyl)hydrazine, acetic acid and sodium borohydride acetate in 1,2-dichloroethane at room temperature produced 5-bromo-N-(2-(2-(2,6-dichlorophenyl)hydrazono)propyl)-2-(methylthio)pyrimidine-4-carboxamide. Reaction of 5-bromo-N-(2-(2-(2,6-dichlorophenyl)hydrazono)propyl)-2-(methylthio)pyrimidine-4-carboxamide and sodium borohydride in the mixed solvent of DCM and methanol produced 5-bromo-N-(2-(2-(2,6-dichlorophenyl)hydrazinyl)propyl)-2-(methylthio)pyrimidine-4-carboxamide. Trifluoromethanesulfonic anhydride and triphenylphosphine reacted in DCM at room temperature, and then produced 5-bromo-N-(2-(2-(2,6-dichlorophenyl)hydrazinyl)propyl)-2-(methylthio)pyrimidine-4-carboxamide for further reaction at 0° C. produced the crude product 2-(5-bromo-2-(methylthio)pyrimidin-4-yl)-N-(2,6-dichlorophenyl)-5-methyl-4,5-dihydro-1H-imidazol-1-amine. Reaction of the crude product and manganese dioxide in dichloromethane at room temperature produced 2-(5-bromo-2-(methylthio)pyrimidin-4-yl)-N-(2,6-dichlorophenyl)-5-methyl-1H-imidazol-1-amine. Heating reaction of 2-(5-bromo-2-(methylthio)pyrimidin-4-yl)-N-(2,6-dichlorophenyl)-5-methyl-1H-imidazol-1-amine and cuprous cyanide in 1,4-dioxane produced 4-(1-((2,6-dichlorophenyl)amino)-5-methyl-1H-imidazol-2-yl)-2-(methylthio)pyrimidine-5-carbonitrile. Heating reaction of 4-(1-((2,6-dichlorophenyl)amino)-5-methyl-1H-imidazol-2-yl)-2-(methylthio)pyrimidine-5-carbonitrile and dioxane solution of hydrochloric acid produced 6-(2,6-dichlorophenyl)-8-methyl-2-(methylthio)imidazo[1,2-b]pyrimido[4,5-d]pyridazin-5 (6H)-one. Reaction of 6-(2,6-dichlorophenyl)-8-methyl-2-(methylthio)imidazo[1,2-b]pyrimido[4,5-d]pyridazin-5(6H)-one and m-CPBA in DCM at room temperature produced the crude intermediates. Heating reaction of the crude intermediates, 3-methyl-4-(4-methylpiperazin-1-yl)aniline and TFA in acetonitrile produced the targeted compound 6-(2,6-dichlorophenyl)-2-((3-chloro-4-(4-methylpiperazin-1-yl)phenyl)amino)-8-methylimidazo[1,2-b]pyrimido[4,5-d]pyridazin-5(6H)-one.

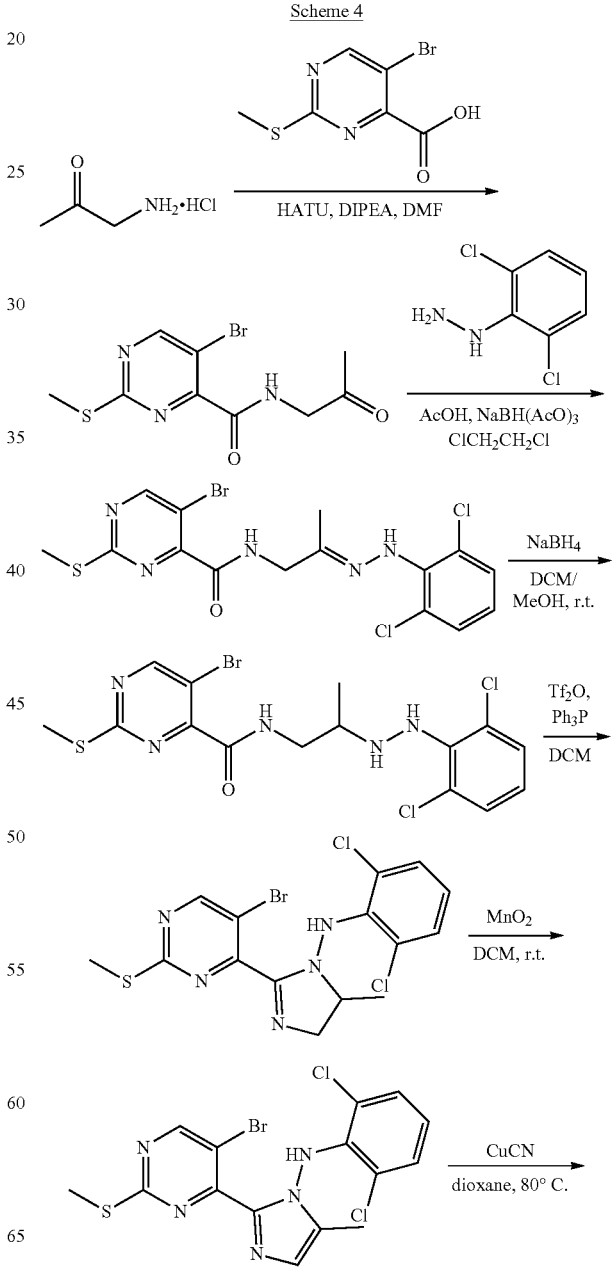

Scheme 4

-continued

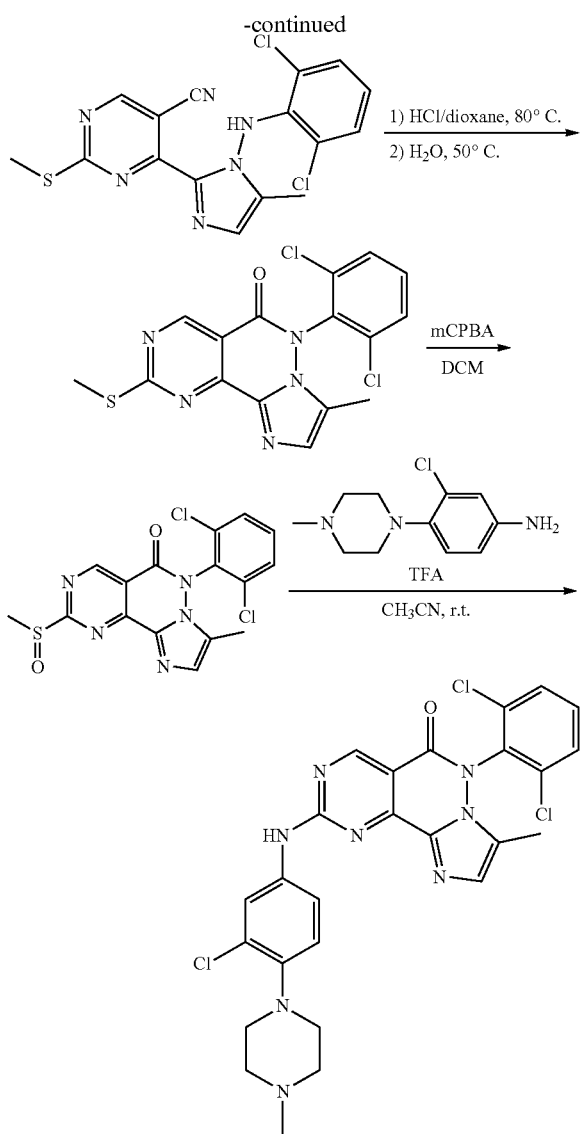

An important aspect of the present disclosure is the discovery that compounds having Formula I (including the compounds of Formula II or III) are kinase inhibitors, especially Wee1 kinase inhibitors. Therefore, these compounds are useful for the treatment of Wee1-related diseases. The term "Wee1-related diseases" described herein refers to Wee1-mediated diseases, especially those that benefit from suppressed Wee1 kinase activity, such as cancer.

The present disclosure includes a therapeutic method comprising administering to a mammal an effective amount of a compound of Formula I, II or III, or a pharmaceutically acceptable salt or prodrug thereof, wherein said therapeutic method is useful for the treatment of Wee1-related diseases, such as cancer. Such diseases that can be treated or prevented by the method or pharmaceutical composition of the present disclosure include, but are not limited to, liver cancer, melanoma, Hodgkin's disease, non-Hodgkin's lymphoma, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head and neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

Compounds of the present disclosure also are useful for the treatment or prevention of other diseases due to abnormal Wee1 activity, such as neurology or neuropsychiatric diseases or conditions, such as depression.

In practicing the therapeutic methods, effective amounts of pharmaceutical preparations are administered to an individual exhibiting the symptoms of one or more of these disorders. Said pharmaceutical formulations containing therapeutically effective concentrations of the compounds of Formula I, II or III are formulated for oral, intravenous, local or topical application and for the treatment of cancer and other diseases. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to an effective regimen. The amount may cure the disease but, typically, is administered in order to ameliorate the symptoms of the disease. Typically, repeated administration is required to achieve the desired amelioration of symptom.

In another embodiment, a pharmaceutical composition comprising a compound of Formula I, II or III or a pharmaceutically acceptable salt thereof, which functions as a kinase inhibitor, in combination with a pharmaceutically acceptable vehicle, is provided.

Another embodiment of the present disclosure is directed to a pharmaceutical composition effective to treat cancer comprising a compound of Formula I, II or III, or a pharmaceutically acceptable salt or prodrug thereof, which functions as a kinase inhibitor, in combination with at least one known anticancer agent or a pharmaceutically acceptable salt thereof. In particular, the compound herein can be combined with other anticancer drugs related to the mechanism of DNA damage and repair, including PARP inhibitors Olaparib, Niraprib, Rucaparib, Talazoparib and any compound prepared in the working examples of the application PCT/CN2012/073362 (the disclosure of incorporated herein in their entirety); HDAC inhibitors Volinota, Romididesin, Papiseta and Bailesta; and so on. And the compound herein can be combined with other anticancer drugs related to cell division detection sites, including Chk1/2 inhibitors, CDK4/6 inhibitors such as Paposinib, ATM/ATR inhibitors, and so on. Other examples of known anticancer agents which may be used for combination therapy include, but not are limited to alkylating agents, such as busulfan, melphalan, chlorambucil, cyclophosphamide, ifosfamide, temozolomide, bendamustine, cis-platin, mitomycin C, bleomycin, and carboplatin; topoisomerase I inhibitors, such as camptothecin, irinotecan, and topotecan; topoisomerase II inhibitors, such as doxorubicin, epirubicin, aclarubicin, mitoxantrone, elliptinium and etoposide; RNA/DNA antimetabolites, such as 5-azacytidine, gemcitabine, 5-fluorouracil and methotrexate; DNA antimetabolites, such as 5-fluoro-2'-deoxy-uridine, fludarabine, nelarabine, ara-C, pralatrexate, pemetrexed, hydroxyurea and thioguanine; antimitotic agents, such as colchicine, vinblastine, vincristine, vinorelbine, paclitaxel, ixabepilone, cabazitaxel and docetaxel; antibodies such as campath, panitumumab, metazotuzumab, navuzumab, pymzumab, remoluzumab, bevacizumab, partuzumab, trastuzumab, cetuximab, obinutuzumab, olfactuzumab, rituximab, alemtuzumab, tiemuzumab, toximab, bentuximab, daremuzumab, errotuzumab, T-DM1, ofatumumab, dinutuximab, blinatumomab, ipilimma, avastin, trastuzumab and rituximab; kinase inhibitors such as imatinib, gefitinib, erlotinib, osimertinib, afatinib, ceritinib, aletinib, crizotinib, erlotinib, lapatinib, sorafenib, regorafenib, vemurafenib, dabrafenib, aflibercept, sunitinib, nilotinib, dasatinib, bosutinib, pratinib, ibrutinib, cabozatinib, lenvatinib, vandetanib, trametinib, cobimetinib, axitinib, temsirolimus, idelalisib, pazopanib, temsirolimus and everolimus. Other known anticancer agents which may be used for combination therapy include tamoxifen, letrozole, fulvestrant, mitoguazone, octreotide, retinoic acid, arsenic trioxide, zoledronic acid, bortezomib, carfazomide, ixazomib, erivedge, sonidegib, denosumab, thalidomide, lenalidomide, venetoclax, aldesleukin (recombinant human interleukin-2) and sipueucel-T (prostate cancer therapeutic vaccine).

In practicing the methods of the present disclosure, the compound of the disclosure may be administered together with at least one known anticancer agent as part of a unitary pharmaceutical composition. Alternatively, the compound of the disclosure may be administered apart from at least one known anticancer agent. In one embodiment, the compound of the disclosure and at least one known anticancer agent are administered substantially simultaneously, i.e. the compounds are administered at the same time or one after the other, so long as the compounds reach therapeutic levels in the blood at the same time. In another embodiment, the compound of the disclosure and at least one known anticancer agent are administered according to their individual dose schedule, so long as the compounds reach therapeutic levels in the blood.

Another embodiment of the present disclosure is directed to a bioconjugate of a compound described herein, which is effective to inhibit neoplasia and functions as a kinase inhibitor. The bioconjugate effective to inhibit neoplasia is consisted of a compound described herein in bioconjugation with at least one known therapeutically useful antibody, such as trastuzumab or rituximab, growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates could also enhance the anticancer effect of the therapeutically useful antibodies, such as trastuzumab or rituximab.

Another embodiment of the present disclosure is directed to a pharmaceutical composition effective to inhibit neoplasia comprising a Wee1 inhibitor of Formula I, II or III, or its pharmaceutically acceptable salt or prodrug in combination with radiation therapy. In this embodiment, the compound of the disclosure may be administered at the same time as the radiation therapy is administered or at a different time.

Yet another embodiment of the present disclosure is directed to a pharmaceutical composition effective for post-surgical treatment of cancer, comprising a Wee1 inhibitor of Formula I, II or III, or its pharmaceutically acceptable salt or prodrug. The disclosure also relates to a method of treating cancer by surgically removing the tumor and then treating the mammal with one of the pharmaceutical compositions described herein.

Pharmaceutical compositions within the scope of this disclosure include all preparations wherein the compounds of the present disclosure are contained in an amount that is effective to achieve its intended purpose. While individual needs vary, determination of optimal ranges of effective amounts of each component is within the skill of the art. Typically, the compounds may be administered to mammals, orally at a dose of from about 0.0025 to 50 mg/kg of body weight, per day, or an equivalent amount of the pharmaceutically acceptable salt thereof, to a mammal being treated. Preferably, from approximately 0.01 to approximately 10 mg/kg of body weight is orally administered. If a known anticancer agent is also administered, it is administered in an amount that is effective to achieve its intended purpose. The optimal amounts of such known anticancer agents effective for cancer are well known to those skilled in the art.

The unit oral dose may comprise from approximately 0.01 to approximately 50 mg, preferably approximately 0.1 to approximately 10 mg of the compound of the disclosure. The unit dose may be administered one or more times daily, as one or more tablets, each containing from approximately 0.1 to approximately 50 mg, conveniently approximately 0.25 to 10 mg of the compound or its solvates.

In a topical formulation, the compound of the disclosure may be present at a concentration of approximately 0.01 to 100 mg per gram of carrier.

In addition to administering the compound as a raw chemical, the compounds of the disclosure may be administered as part of a pharmaceutical preparation containing suitable pharmaceutically acceptable carriers comprising excipients and auxiliaries, which facilitate processing of the compounds into preparations that may be used pharmaceutically. Preferably, the pharmaceutical preparations, particularly those preparations which may be administered orally and that may be used for the preferred type of administration, such as tablets, dragees, and capsules, as well as suitable solutions for administration by injection or orally, contain from approximately 0.01 to 99 percent, preferably from approximately 0.25 to 75 percent of active compound(s), together with the excipient.

Also included within the scope of the present disclosure are the non-toxic pharmaceutically acceptable salts of the compounds of the present disclosure. Acid addition salts are formed by mixing a solution of the compounds of the present disclosure with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Base addition salts are formed by mixing a solution of the compounds of the present disclosure with a solution of a pharmaceutically acceptable non-toxic base, such as sodium hydroxide, potassium hydroxide, choline hydroxide, sodium carbonate, tris(hydroxymethyl)aminomethane (TRIS), N-methyl-glucamine and the like.

The pharmaceutical preparations of the disclosure may be administered to any mammal, so long as they may experience the therapeutic effects of the compounds of the disclosure. Foremost among such mammals are humans and veterinary animals, although the disclosure is not intended to be so limited.

The pharmaceutical preparations of the present disclosure may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, frequency of treatment, and the nature of the effect desired.

The pharmaceutical preparations of the present disclosure are manufactured in a manner, which is itself known, e.g., by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular: fillers, such as saccharides, e.g. lactose or sucrose, mannitol or sorbitol; cellulose preparations and/or calcium phosphates, e.g. tri-calcium phosphate or calcium hydrogen phosphate; as well as binders, such as starch paste, including, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable celluloses, such as acetylcellulose phthalate or hydroxypropylmethyl-cellulose phthalate, are used. Dye stuffs or pigments may be added to the tablets or dragee core coatings, e.g., for identification or in order to characterize combinations of active compound doses.

Other pharmaceutical preparations, which may be used orally, include push-fit capsules made of gelatin, as well as soft, sealed capsules made of gelatin and a plasticizer, such as glycerol or sorbitol. The push-fit capsules may contain the active compounds in the form of granules, which may be mixed with fillers, such as lactose; binders, such as starches; and/or lubricants, such as talc or magnesium stearate and, optionally, stabilizers. In soft capsules, the active compounds are preferably dissolved or suspended in suitable liquids, such as fatty oils, or liquid paraffin. In addition, stabilizers may be added.

Suitable formulations for parenteral administration include aqueous solutions of the active compounds, e.g., aqueous solutions and alkaline solutions of water-soluble salts. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400, or cremophor, or cyclodextrins. Aqueous injection suspensions may contain substances which increase the viscosity of the suspension, e.g., sodium carboxymethyl cellulose, sorbitol, and/or dextran. Optionally, the suspension may also contain stabilizers.

In accordance with one aspect of the present disclosure, compounds of the disclosure are employed in topical and parenteral formulations and are used for the treatment of skin cancer.

The topical formulations of this disclosure are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included, as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture of the active ingredient, dissolved in a small amount of an oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil, with warm soft paraffin and allowing the mixture to cool. A typical example of such an ointment is one which includes approximately 30% almond oil and approximately 70% white soft paraffin by weight.

The present disclosure also includes the use of the compounds of the subject disclosure in the manufacture of a medicament for treating a clinical condition responsive to the inhibition of Wee1 activity. The medicament may include the pharmaceutical compositions as described above.

The following examples are illustrative, but not limiting, of the method and compositions of the present disclosure. Other suitable modifications and adaptations of the variety of conditions and parameters normally encountered in clinical therapy and which are obvious to those skilled in the art are within the spirit and scope of the disclosure.

EXAMPLES

General Remarks

All reagents were of commercial quality. Solvents were dried and purified by standard methods. Mass spectrum analyses were recorded on a Platform II (Agilent 6110) quadrupole mass spectrometer fitted with electrospray. $^1$H NMR spectra was recorded at 400 MHz, on a Brücker Ascend 400 apparatus. Chemical shifts were recorded as parts per million (ppm) downfield from TMS (0.00 ppm), and J coupling constants were reported in hertz (Hz).

Example 1

6-(2,6-dichlorophenyl)-2-((4-(4-methylpiperazin-1-yl)phenyl)amino)imidazo[1,2-b]pyrimido[4,5-d]pyridazin-5(6H)-one a) Preparation of tert-butyl (2-(2-(2,6-dichlorophenyl)hydrazinyl)ethyl)carbamate: to the solution of N-tert-butoxycarbonyl-2-aminoacetaldehyde (15.5 g, 97.4 mmol) in DCM (300 mL) were added (2,6-dichlorophenyl)hydrazine (15.7 g, 88.7 mmol) and sodium triacetoxyborohydride (37 g, 174.5 mmol) in sequence. The reaction liquor was stirred at room temperature overnight, and then sodium cyanoborohydride (11 g, 175 mmol) was further added. After addition, the reaction liquor was stirred for 3 hours at room temperature. An aqueous solution of sodium bicarbonate (300 mL) was added to the reaction system, the organic layer was separated, and the aqueous layer was extracted with DCM (150 mL×2). The organic layers were collected, washed with saturated saline, dried with anhydrous sodium sulfate, filtered, and concentrated under reduced pressure to give the crude product, which was purified by column chromatography (silica gel, petroleum ether (PE): ethyl acetate (EA)=6:1 as the eluent) to give the targeted compound (12.5 g, 44% yield, yellow solid). LC-MS (ESI): m/z (M+H)$^+$ 320.72.

b) Preparation of benzyl 1-(2-((tert-butoxycarbonyl) amino)ethyl)-2-(2,6-dichlorophenyl)hydrazine-1-carboxylate: to the solution of tert-butyl (2-(2-(2,6-dichlorophenyl) hydrazinyl)ethyl)carbamate (10 g, 31.2 mmol) in DCM (100 mL), were added DIPEA (16.5 mL, 93.6 mmol) and benzyl chloroformate (5.8 mL, 40.5 mmol) in sequence. After the reaction liquor was stirred at room temperature for 2 hours, an aqueous solution of sodium bicarbonate (100 mL) was added, the organic layer was separated, and the aqueous layer was extracted with DCM (50 mL×2). The organic layers were collected, washed with saturated saline, dried with anhydrous sodium sulfate, filtered, and concentrated under reduced pressure to give the crude product, which was purified by column chromatography (silica gel, PE:EA=8:1 as the eluent) to give the targeted compound (13.8 g, 97% yield, yellow solid). LC-MS (ESI): (M+H)$^+$ 454.30.

c) Preparation of benzyl 1-(2-aminoethyl)-2-(2,6-dichlorophenyl)hydrazine-1-carboxylate hydrochloride: benzyl 1-(2-((tert-butoxycarbonyl)amino)ethyl)-2-(2,6-dichlorophenyl)hydrazine-1-carboxylate (13.8 g, 30.4 mmol) was dissolved in dioxane solution of hydrochloric acid (4 N, 130 mL). The reaction mixture was stirred at room temperature for 3 hours, removed the solvent under reduced pressure to give the targeted compound (11.8 g, 100% yield, yellow solid). LC-MS (ESI): m/z (M+H)$^+$ 353.98.

d) Preparation of benzyl 1-(2-(2-(methylthio)-5-bromopyrimidine-4-carboxamido)ethyl)-2-(2,6-dichlorophenyl) hydrazine-1-carboxylate: benzyl 1-(2-aminoethyl)-2-(2,6-dichlorophenyl)hydrazine-1-carboxylate hydrochloride (10.5 g, 26.9 mmol) was dissolved in DMF (100 mL), and to the solution was added DIPEA (13 mL, 134.5 mmol). After the reaction mixture was cooled down to 0° C., to which a DCM (80 mL) solution of 5-bromo-2-(methylthio) pyrimidine-4-carbonyl chloride (6 g, 22.4 mmol) was added dropwise slowly. After addition and the reaction liquor was stirred at 0° C. for 45 min, a saturated aqueous solution of sodium bicarbonate (100 mL) was added to the reaction system, the organic layer was separated, and the aqueous layer was extracted with DCM (50 mL×2). The organic layers were collected, washed with saturated saline, dried with anhydrous sodium sulfate, filtered, and concentrated under reduced pressure to give the crude product, which was purified by column chromatography (silica gel, PE:EA=4:1 as the eluent) to give the targeted compound (10.2 g, 77.7% yield, yellow solid). LC-MS (ESI): (M+H)$^+$ 584.34.

e) Preparation of 2-(methylthio)-5-bromo-N-(2-(2-(2,6-dichlorophenyl)hydrazinyl)ethyl)-pyrimidine-4-carboxamide: benzyl 1-(2-(2-(methylthio)-5-bromopyrimidine-4-carboxamido)ethyl)-2-(2,6-dichlorophenyl)hydrazine-1-carboxylate (10.2 g, 17.4 mmol) was dissolved in TFA (110 mL). After the reaction mixture was stirred at 65° C. for 2 hours, the mixture was concentrated under reduced pressure, and DCM (200 mL) was added for dissolution. Then a saturated aqueous solution of sodium bicarbonate (100 mL) was added to the reaction system, the organic layer was separated, and the aqueous lay was extracted with DCM (50 mL×2). The organic layers were collected, washed with saturated saline, dried with anhydrous sodium sulfate, filtered, and concentrated under reduced pressure to give the crude product, which was purified by column chromatography (silica gel, PE:EA=4:1 as the eluent) to give the targeted compound (6.1 g, 77.6% yield, yellow solid). LC-MS (ESI): m/z (M+H)$^+$ 450.47. $^1$H NMR (400 MHz, CDCl$_3$) δ 8.76 (s, 1H), 8.05 (br s, 1H), 7.28-7.26 (m, 1H), 7.25-7.24 (m, 1H), 6.92-6.86 (m, 1H), 5.84 (br s, 1H), 3.60-3.55 (m, 2H), 2.99 (t, J=5.4 Hz, 2H), 2.57 (s, 3H).

f) Preparation of 2-(2-(methylthio)-5-bromopyrimidin-4-yl)-N-(2,6-dichlorophenyl)-4,5-dihydro-1H-imidazol-1-amine: 2-(methylthio)-5-bromo-N-(2-(2-(2,6-dichlorophenyl)hydrazinyl)ethyl)-pyrimidine-4-carboxamide (1 g, 2.21 mmol) was dissolved in DCM (50 mL). After the reaction liquor was cooled down to 0° C., PCl$_5$ (922 mg, 4.43 mmol) was added slowly. After the reaction liquor was stirred at room temperature for 1 hour, cooled down to 0° C., and added to methanol (50 mL) slowly. After stirred at 0° C. for 15 min, a saturated aqueous solution of sodium bicarbonate (100 mL) was added to the reaction system, the organic layer was separated, and the aqueous layer was extracted with DCM (50 mL×2). The organic layers were collected, washed with saturated saline, dried with anhydrous sodium sulfate, filtered, and concentrated under reduced pressure to give the crude product, which was purified by column chromatography (silica gel, PE:EA=2:1 as the eluent) to give the targeted compound (550 mg, 57.3% yield, yellow solid). LC-MS (ESI): m/z (M+H)$^+$ 432.05.

g) Preparation of 2-(2-methylthio-5-cyanopyrimidin-4-yl)-N-(2,6-dichlorophenyl)-1H-imidazol-1-amine: 2-(2-(methylthio)-5-bromopyrimidin-4-yl)-N-(2,6-dichlorophenyl)-4,5-dihydro-1H-imidazol-1-amine (300 mg, 0.69 mmol) and cuprous cyanide (123 mg, 1.38 mmol) were dissolved in DMF (10 mL). After the reaction liquor was stirred at 120° C. for 3 hours, the liquor was cooled to room temperature. Then ammonium hydroxide (30 mL) and EA (20 mL) were added, the organic layer was separated, and the aqueous layer was extracted with EA (50 mL×2). The organic layers were collected, washed with saturated saline, dried with anhydrous sodium sulfate, filtered, and concentrated under reduced pressure to give the crude product, which was purified by column chromatography (silica gel, DCM:methanol=10:1 as the eluent) to give the targeted compound (150 mg, 57.5% yield, yellow solid). LC-MS (ESI): m/z (M+H)$^+$377.10.

h) Preparation of 2-(methylthio)-6-(2,6-dichlorophenyl) imidazo[1,2-b]pyrimido[4,5-d]pyridazin-5(6H)-one: 2-(2-methylthio-5-cyanopyrimidin-4-yl)-N-(2,6-dichlorophenyl)-1H-imidazol-1-amine (50 mg, 0.13 mmol) was added to the dioxane solution of hydrochloric acid (4 N, 10 mL). After the reaction liquor was stirred at 80° C. for 2 days, the liquor was cooled to room temperature, the organic solvent was removed under reduced pressure, to the liquor was added aqueous solution of sodium bicarbonate (10 mL) and EA (10 mL), the organic layer was separated, and the aqueous layer was extracted with EA (5 mL×2). The organic layers were collected, washed with saturated saline, dried with anhydrous sodium sulfate, filtered, and concentrated under reduced pressure to give the crude product, which was purified by column chromatography (silica gel, DCM: methanol=10:1 as the eluent) to give the targeted compound (30 mg, 59.9% yield, yellow solid). LC-MS(ESI):m/z (M+H)$^+$ 378.30.

i) Preparation of 2-(methylsulfonyl)-6-(2,6-dichlorophenyl)imidazo[1,2-b]pyrimido[4,5-d]pyridazin-5(6H)-one: 2-(methylthio)-6-(2,6-dichlorophenyl)imidazo[1,2-b]pyrimido[4,5-d]pyridazin-5(6H)-one (30 mg, 0.079 mmol)

was dissolved in DCM (3 mL), and to the solution was added m-CPBA (85%, 18 mg, 0.089 mmol). The reaction liquor was stirred at room temperature for 2 hours, and then concentrated under reduced pressure to give the crude product used for the next step directly. LC-MS (ESI): m/z (M+H)⁺ 410.08.

j) Preparation of 6-(2,6-dichlorophenyl)-2-((4-(4-methylpiperazin-1-yl)phenyl)amino)imidazo[1,2-b]pyrimido[4,5-d]pyridazin-5(6H)-one: 2-(methylsulfonyl)-6-(2,6-dichlorophenyl)imidazo[1,2-b]pyrimido[4,5-d]pyridazin-5(6H)-one (32.4 mg, 0.079 mmol) and 4-(4-methylpiperazin-1-yl)aniline (23 mg, 0.12 mmol) were dissolved in acetonitrile (3 mL), and to the solution was added TFA (0.05 mL). After the reaction liquor was stirred at room temperature overnight, the organic solvent was removed under reduced pressure to give the crude product, which was purified by preparative liquid chromatography (column C18, 0-100% acetonitrile/water as mobile phase) to give the targeted compound (7 mg, 17.1% yield, yellow solid).

Example 2

6-(2,6-difluorophenyl)-2-((3-methyl-4-(4-methylpiperazin-1-yl)phenyl)amino)imidazo[1,2-b]pyrimido[4,5-d]pyridazin-5(6H)-one a) Preparation of N-(2,2-dimethoxyethyl)-2-(methylthio)-5-bromopyrimidine-4-carboxamide: at room temperature, to the solution of 2-(methylthio)-5-bromopyrimidine-4-carboxylic acid (40.0 g, 160.6 mmol) in THF (200 mL) was added carbonyldiimidazole (33.8 g, 208.8 mmol). After replacement with nitrogen, the reaction liquor was stirred at 60° C. for 2 hours, and then cooled to below 60° C. To the reaction mixture was added 2,2-dimethoxyethan-1-amine (22.0 g, 208.8 mmol) slowly, after replacement with nitrogen, the reaction was stirred at room temperature overnight. Water (100 mL) was added, and the reaction mixture was stirred at room temperature for 30 min, the filter cake was washed with diethyl ether twice, and dried under reduced pressure to give the targeted compound (43.0 g, 80% yield, yellow solid). LC-MS (ESI): m/z (M+H)⁺ 336.21.

b) Preparation of N-(2-oxoethyl)-2-(methylthio)-5-bromopyrimidine-4-carboxamide: at room temperature, N-(2,2-dimethoxyethyl)-2-(methylthio)-5-bromopyrimidine-4-carboxamide (15.0 g, 44.7 mmol) and diluted hydrochloric acid (1M, 100 mL) were added to acetone (100 mL), and replaced with nitrogen once. After the reaction mixture was stirred at 50° C. for 4 hours, the reaction was cooled to room temperature, and the organic solvent was concentrated under reduced pressure to give the targeted compound (10.6 g, 81% yield, white solid). LC-MS (ESI): m/z (M+H)⁺ 289.92.

c) Preparation of N-(2-(2-(2,6-difluorophenyl)hydrazinyl)ethyl)-2-(methylthio)-5-bromopyrimidine-4-carboxamide: at room temperature, to methanol (200 mL) was added N-(2-oxoethyl)-2-(methylthio)-5-bromopyrimidine-4-carboxamide (8 g, 27.7 mmol), (2,6-difluorophenyl)hydrazine (4.8 g, 33.2 mmol) and acetic acid (7 mL) in sequence. After the reaction mixture was stirred at room temperature for 1 hour, sodium cyanoborohydride (1.8 g, 27.7 mmol) was added slowly. The reaction mixture was stirred at room temperature for 1 hour, and the organic solvent was removed under reduced pressure to give the crude product. The crude product was dissolved in DCM (50 mL), to which was added saturated aqueous solution of sodium bicarbonate (100 mL) for extraction, and the aqueous phase was extracted with DMC (50 mL×2). The organic layers were collected, washed with saturated saline, dried with anhydrous sodium sulfate, filtered, and concentrated under reduced pressure to give the crude product, which was purified by column chromatography (silica gel, PE:EA=1:1) to give the targeted product (13.1 g, 90% yield, yellow solid). LC-MS (ESI): m/z (M+H)+418.06.

d) Preparation of N-(2,6-difluorophenyl)-2-(2-(methylthio)-5-bromopyrimidin-4-yl)-4,5-dihydro-1H-imidazol-1-amine: at room temperature, N-(2-(2-(2,6-difluorophenyl)hydrazinyl)ethyl)-2-(methylthio)-5-bromopyrimidine-4-carboxamide (6.0 g, 14.4 mmol) was dissolved in anhydrous DCM (200 mL), and PCl₅ (9.0 g, 43.2 mmol) was added in batches. After the reaction mixture was stirred at room temperature for 4 hours, the reaction liquor was added to the mixed solution of iced methanol (100 mL) and sodium bicarbonate solid (10 g), and stirred for 10 min, and then filtered, and the filtrate was dried to give the crude product which was used for the next step directly. LC-MS (ESI): m/z (M+H)⁺400.06.

e) Preparation of N-(2,6-difluorophenyl)-2-(2-(methylthio)-5-bromopyrimidin-4-yl)-1H-imidazol-1-amine: at room temperature, N-(2,6-difluorophenyl)-2-(2-(methylthio)-5-bromopyrimidin-4-yl)-4,5-dihydro-1H-imidazol-1-amine (the crude product from the above step) and manganese dioxide (6.5 g, 72.0 mmol) were added to DCM (200 mL). After the reaction mixture was stirred at room temperature for 20 hours, manganese dioxide was removed by filtration, and the organic solvent was removed under reduced pressure to give the crude product, which was purified by column chromatography (silica gel, PE:EA=1:1) to give the targeted compound (2.5 g, 44% yield for two steps, red oil). LC-MS (ESI): m/z (M+H)⁺ 398.06.

f) Preparation of 2-(methylthio)-4-(1-((2,6-difluorophenyl)amino)-1H-imidazol-2-yl)pyrimidine-5-carbonitrile: at room temperature, N-(2,6-difluorophenyl)-2-(2-(methylthio)-5-bromopyrimidin-4-yl)-1H-imidazol-1-amine (4.5 g, 11.4 mmol) and cuprous cyanide (2.1 g, 27.8 mmol) were added to 1,4-dioxane (30 mL). After the reaction mixture was stirred at 80° C. for 20 hours, it was cooled to room temperature. The reaction liquor was poured into water (100 mL) and extracted with EA (50 mL×3). The organic layers were collected, washed with saturated saline, dried with anhydrous sodium sulfate, filtered, and the organic solvent was removed under reduced pressure to give the crude product, which was purified by column chromatography (silica gel, PE:EA=1:1) to give the targeted product (2.0 g, 50% yield, yellow solid). LC-MS (ESI): m/z (M+H)⁺ 345.00.

g) Preparation of 2-(methylthio)-6-(2,6-difluorophenyl)imidazo[1,2-b]pyrimido[4,5-d]pyridazin-5(6H)-one: at room temperature, 2-(methylthio)-4-(1-((2,6-difluorophenyl)amino)-1H-imidazol-2-yl)pyrimidine-5-carbonitrile (2.0 g, 5.8 mmol) was added to dioxane solution of hydrochloric acid (4M, 20 mL). After the reaction mixture was stirred at 80° C. for 15 h, the reaction mixture was cooled to 50° C., and water (10 mL) was added. After the reaction mixture was stirred at 50° C. for 2 hours, the reaction mixture was cooled to room temperature. The organic solvent was removed under reduced pressure, to which EA (50 mL) and saturated aqueous solution of sodium bicarbonate (20 mL) were added for extraction. The aqueous phase was extracted with EA (15 mL×2). The organic layers were collected, washed with saturated saline, dried with anhydrous sodium sulfate, and the organic solvent was removed under reduced pressure to give the targeted product (1.5 g, 74% yield, yellow solid). LC-MS (ESI): m/z (M+H)⁺ 346.00. ¹H NMR (400 MHz, CDCl₃): δ 9.36 (s, 1H), 7.72-7.63 (m, 1H), 7.51 (d, J=1.0 Hz, 1H), 7.26-7.22 (m, 2H), 7.01-6.98 (m, 1H), 2.77 (s, 3H).

h) Preparation of 6-(2,6-difluorophenyl)-2-((3-methyl-4-(4-methylpiperazin-1-yl)phenyl)amino)imidazo[1,2-b]pyrimido[4,5-d]pyridazin-5(6H)-one: 2-(methylthio)-6-(2,6-difluorophenyl)imidazo[1,2-b]pyrimido[4,5-d]pyridazin-5(6H)-one (80 mg, 0.22 mmol) was dissolved in anhydrous DCM (3 mL). At 0° C., m-CPBA (58 mg, 0.33 mmol) was added to the reaction system, and after addition, the temperature of the reaction liquor was increased to room temperature, and stirred at room temperature for 1 hour, and then the organic solvent was removed under reduced pressure to give the crude product. The crude product was dissolved in acetonitrile (5 mL), and 3-methyl-4-(4-methylpiperazin-1-yl)aniline (67 mg, 0.33 mmol) and TFA (2 drops) were added to the reaction system. The reaction liquor was increased to room temperature and stirred at room temperature for 1 hour, and the value of pH of the reaction liquor was adjusted to 7-8 with saturated aqueous solution of sodium bicarbonate. DCM (50 Ml) and water (30 mL) were added for liquid separation, the aqueous phase was extracted with DCM (30 mL×2). The organic layers were collected, washed with saturated saline, dried with anhydrous sodium sulfate, filtered, and the organic solvent was removed under reduced pressure to give the crude product, which was purified by preparative liquid chromatography (column C18, 0-100% acetonitrile/water as mobile phase) to give the targeted compound (57 mg, 51.8% yield, yellow solid).

The compounds of Examples 3-25 were prepared from 5-bromo-2-(methylthio)pyrimidine-4-carboxylic acid, 2,2-dimethoxyethan-1-amine, (2,6-disubstitutedphenyl)hydrazine, cuprous cyanide and the corresponding substituted aniline or substituted tetrahydroisoquinoline amine using procedure similar to those described for the synthesis of compound of Example 2.

Firstly, the intermediate of Example 26 was prepared from 2-(methylthio)-6-(2,6-dichlorophenyl)imidazo[1,2-b]pyrimido[4,5-d]pyridazin-5(6H)-one and tert butyl 4-(4-amino-2-methylphenyl)piperazine-1-carboxylate using procedure similar to those described for the synthesis of compound of Example 2 h. The intermediate and dioxane solution of hydrochloric acid were reacted at room temperature for deprotection to give the targeted compound of Example 26.

The compounds of Examples 27-45 were prepared from 5-bromo-2-(methylthio)pyrimidine-4-carboxylic acid, 2,2-dimethoxyethan-1-amine, (2,6-disubstitutedphenyl)hydrazine, cuprous cyanide and the corresponding substituted aniline or substituted tetrahydroisoquinoline amine using procedure similar to those described for the synthesis of compound of Example 2.

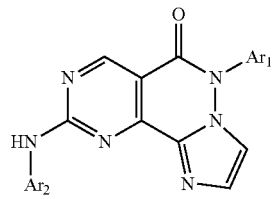

| Example | Ar₁ | Ar₂ | LC-MS (ESI) | ¹H NMR |
|---|---|---|---|---|
| 1 | 2,6-dichlorophenyl | 4-(4-methylpiperazin-1-yl)phenyl | (M + H)⁺ 521.48 | DMSO-d₆: δ 10.54 (brs, 1H), 9.15 (s, 1H), 7.91-7.80 (m, 3H), 7.79-7.75 (m, 1H), 7.63-7.55 (m, 1H), 7.43 (d, J = 21.4 Hz, 2H), 7.02-6.93 (m, 2H), 3.16-3.09 (m, 4H), 2.46 (t, J = 4.8 Hz, 4H), 2.23 (s, 3H). |
| 2 | 2,6-difluorophenyl | 3-methyl-4-(4-methylpiperazin-1-yl)phenyl | (M + H)⁺ 503.24 | DMSO-d₆: δ 10.56 (brs, 1H), 9.15 (s, 1H), 8.00-7.79 (m 2H), 7.76-7.63 (m, 1H), 7.59 (s, 1H), 7.56-7.51 (m, 2H), 7.47 (s, 1H), 7.06 (d, J = 8.4 Hz, 1H), 2.89-2.82 (m, 4H), 2.59-2.51 (m, 4H), 2.30-2.24 (m, 6H). |
| 3 | 2,6-dichlorophenyl | 3-methyl-4-(4-methylpiperazin-1-yl)phenyl | (M + H)⁺ 535.41 | CDCl₃: δ 9.34 (s, 1H), 7.84-7.74 (m, 1H), 7.64-7.59 (m, 2H), 7.55 (dd, J = 9.3, 6.7 Hz, 1H), 7.43 (d, J = 12.1 Hz, 2H), 7.12 (d, J = 8.2 Hz, 1H), 6.77 (d, J = 1.2 Hz, 1H), 3.09 (t, J = 4.6 Hz, 4H), 2.98-2.80 (m, 4H), 2.56 (s, 3H), 2.35 (s, 3H). |
| 4 | 2,6-dichlorophenyl | 3,5-dimethyl-4-(4-methylpiperazin-1-yl)phenyl | (M + H)⁺ 549.30 | CDCl₃: δ 9.35 (s, 1H), 7.75-7.68 (m, 1H), 7.63-7.60 (m, 2H), 7.57-7.52 (m, 1H), 7.45-7.43 (m, 1H), 7.32-7.27 (m, 1H), 6.77 (d, J = 1.1 Hz, 1H), 3.30-3.19 (m, 4H), 2.78-2.67 (m, 4H), 2.51 (s, 3H), 2.38 (s, 6H). |

-continued
| Example | Ar₁ | Ar₂ | LC-MS (ESI) | ¹H NMR |
|---|---|---|---|---|
| 5 | 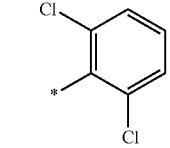 [SMILES: *c1c(Cl)cccc1Cl] | 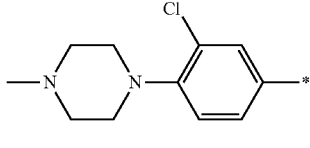 | M.W. 555.85 | — |
| 6 | 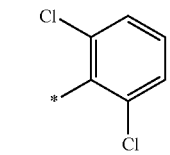 | 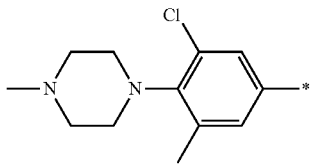 | M.W. 569.88 | — |
| 7 | 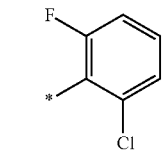 | 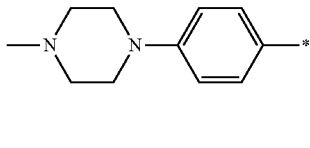 [SMILES: *c1ccc(N2CCN(C)CC2)cc1] | (M + H)⁺ 505.49 | MeOD: δ 9.21 (s, 1H), 7.98-7.88 (m, 1H), 7.80-7.74 (m, 1H), 7.72-7.59 (m, 2H), 7.54-7.45 (m, 2H), 7.30-7.25 (m, 1H), 7.08 (d, J = 8.7 Hz, 2H), 3.46-3.32 (m, 4H), 3.27-3.15 (m, 4H), 2.80 (s, 3H). |
| 8 | 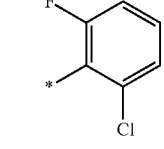 | 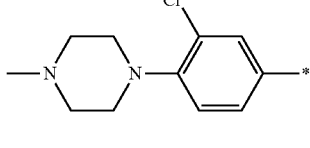 | M.W. 539.40 | — |
| 9 | 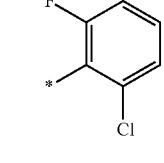 | 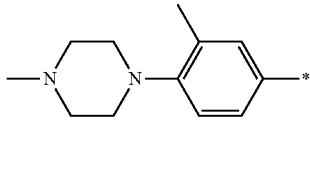 [SMILES: *c1ccc(N2CCN(C)CC2)c(C)c1] | (M + H)⁺ 519.23 | CDCl₃: δ 9.32 (s, 1H), 7.83 (br s, 1H), 7.63-7.58 (m, 1H), 7.56-7.37 (m, 4H), 7.35-7.30 (m, 1H), 7.11 (d, J = 8.3 Hz, 1H), 6.85 (s, 1H), 3.63-3.45 (m, 2H), 3.11-3.05 (m, 4H), 2.94-2.88 (m, 2H), 2.58 (s, 3H), 2.35 (s, 3H). |
| 10 | 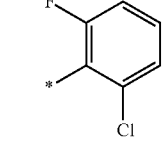 | 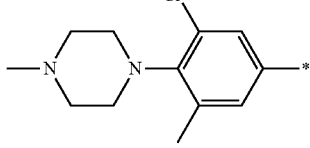 | M.W. 553.42 | — |
| 11 | 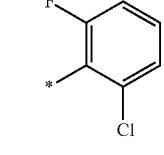 | 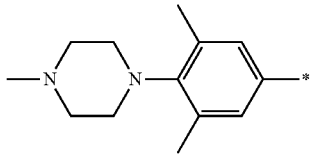 | (M + H)⁺ 533.22 | DMSO-d₆: δ 10.58 (brs, 1H), 9.17 (s, 1H), 7.86-7.80 (m, 1H), 7.74 (d, J = 8.2 Hz, 1H), 7.69-7.65 (m, 1H), 7.60-7.32 (m, 4H), 3.12-3.07 (m, 4H), 2.72-2.63 (m, 4H), 2.43 (s, 3H), 2.30 (s, 6H). |
| 12 | 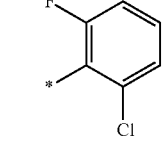 | 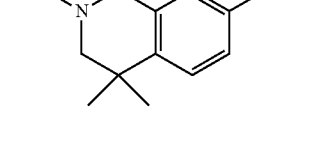 | (M + H)⁺ 504.21 | CDCl₃: δ 9.32 (s, 1H), 8.01 (s, 1H), 7.65-7.59 (m, 1H), 7.56-7.47 (m, 2H), 7.46-7.30 (m, 4H), 6.85 (s, 1H), 4.02 (brs, 2H), 2.92-2.70 (m, 5H), 1.44 (s, 6H). |
| 13 | 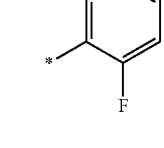 | 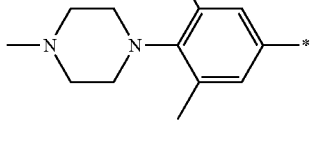 | (M + H)⁺ 517.21 | DMSO-d₆: δ 10.56 (brs, 1H), 9.16 (s, 1H), 7.89-7.83 (m, 1H), 7.65-7.43 (m, 6H), 3.06-3.01 (m, 4H), 2.49-2.46 (m, 4H), 2.32-2.26 (m, 9H). |

-continued

| Example | Ar₁ | Ar₂ | LC-MS (ESI) | ¹H NMR |
|---|---|---|---|---|
| 14 | 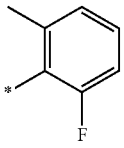 | 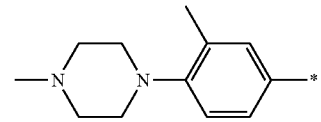 | (M + H)⁺ 499.14 | CDCl₃: δ 9.34 (s, 1H), 7.77-7.70 (m, 1H), 7.54-7.51 (m, 1H), 7.47-7.41 (m, 2H), 7.30-7.27 (m, 1H), 7.22-7.18 (m, 1H), 7.13 (d, J = 8.4 Hz, 1H), 6.83-6.80 (m, 1H), 3.25-2.89 (m, 8H), 2.68 (s, 3H), 2.35 (s, 3H), 2.24 (s, 3H). |
| 15 | 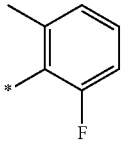 | 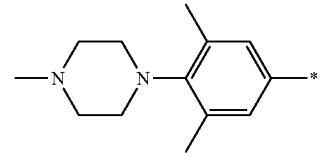 [SMILES: *c1cc(C)c(N2CCN(C)CC2)c(C)c1] | (M + H)⁺ 513.30 | CDCl₃: δ 9.35 (s, 1H), 7.76-7.68 (m, 1H), 7.55-7.50 (m, 1H), 7.44-7.41 (m, 1H), 7.34-7.27 (m, 2H), 7.22-7.18 (m, 1H), 6.82-6.81 (m, 1H), 3.39-3.23 (m, 4H), 2.93-2.82 (m, 4H), 2.60 (s, 3H), 2.37 (s, 6H), 2.24 (s, 3H). |
| 16 | 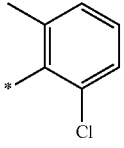 | 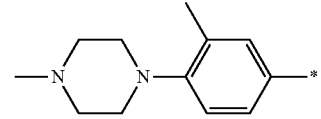 [SMILES: *c1ccc(N2CCN(C)CC2)c(C)c1] | (M + H)⁺ 515.32 | CDCl₃: δ 9.34 (s, 1H), 7.80-7.69 (m, 1H), 7.52-7.38 (m, 5H), 7.11 (d, J = 8.1 Hz, 1H), 6.73 (d, J = 1.1 Hz, 1H), 3.03 (t, J = 4.7 Hz, 4H), 2.86-2.65 (m, 4H), 2.47 (s, 3H), 2.35 (s, 3H), 2.26 (s, 3H). |
| 17 | 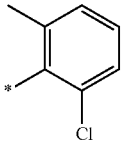 | 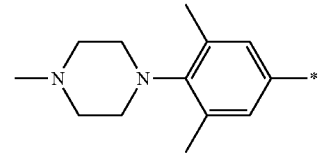 [SMILES: *c1cc(C)c(N2CCN(C)CC2)c(C)c1] | (M + H)⁺ 529.35 | CDCl₃: δ 9.35 (s, 1H), 7.76-7.67 (m, 1H), 7.52-7.46 (m, 2H), 7.43-7.38 (m, 2H), 7.34-7.28 (m, 1H), 6.73 (d, J = 1.1 Hz, 1H), 3.31-3.21 (m, 4H), 2.83-2.74 (m, 4H), 2.54 (s, 3H), 2.38 (s, 6H), 2.26 (s, 3H). |
| 18 | 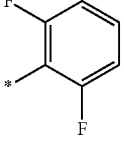 [SMILES: *c1c(C)cccc1F] | 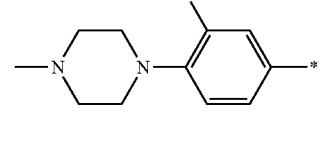 | (M + H)⁺ 523.15 | DMSO-d₆: δ 10.80 (brs, 1H), 9.21 (s, 1H), 8.09-7.70 (m, 3H), 7.63 (s, 1H), 7.57-7.49 (m, 3H), 7.24 (d, J = 8.6 Hz, 1H), 3.11-3.02 (m, 4H), 2.91-2.76 (m, 4H), 2.51 (s, 3H). |
| 19 | 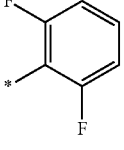 [SMILES: *c1c(C)cccc1F] | 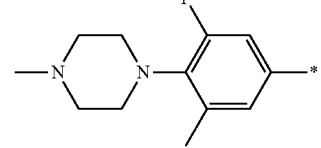 | (M + H)⁺ 521.25 | DMSO-d₆: δ 10.79 (brs, 1H), 9.21 (s, 1H), 8.05-7.81 (m, 2H), 7.62 (s, 1H), 7.57-7.49 (m, 3H), 7.46-7.38 (m, 1H), 3.07-2.95 (m, 4H), 2.63-2.51 (m, 4H), 2.33-2.28 (m, 6H). |
| 20 | 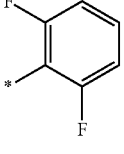 | 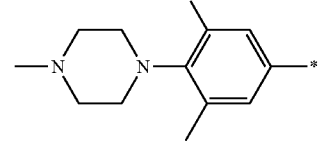 | (M + H)⁺ 537.17 | DMSO-d₆: δ 10.77 (brs, 1H), 9.21 (s, 1H), 8.17-7.90 (m, 1H), 7.90-7.84 (m, 1H), 7.70-7.58 (m, 2H), 7.57-7.49 (m, 3H), 3.39-3.34 (m, 2H), 2.87-2.79 (m, 2H), 2.67-2.59 (m, 2H), 2.33 (s, 3H), 2.32-2.27 (m, 2H), 2.26 (s, 3H). |
| 21 | 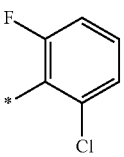 | 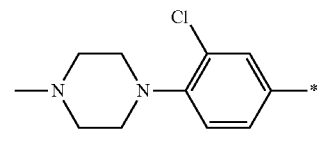 | (M + H)⁺ 539.17 | DMSO-d₆: δ 10.82 (brs, 1H), 9.22 (s, 1H), 8.19-7.81 (m, 3H), 7.75 (d, J = 8.2 Hz, 1H), 7.70-7.65 (m, 1H), 7.55-7.45 (m, 2H), 7.25 (d, J = 8.6 Hz, 1H), 3.15-3.05 (m, 4H), 3.01-2.85 (m, 4H), 2.57 (s, 3H). |
| 22 | 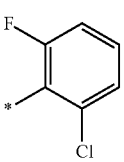 [SMILES: *c1c(F)cccc1Cl] | 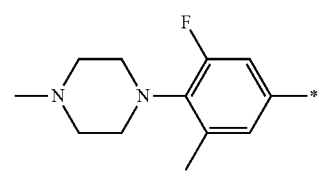 [SMILES: *c1cc(C)c(N2CCN(C)CC2)c(F)c1] | (M + H)⁺ 537.25 | DMSO-d₆: δ 10.80 (brs, 1H), 9.22 (s, 1H), 8.09-7.79 (m, 2H), 7.74 (d, J = 8.2 Hz, 1H), 7.70-7.65 (m, 1H), 7.56-7.47 (m, 2H), 7.42 (s, 1H), 3.53-3.39 (m, 2H), 3.09-2.92 (m, 4H), 2.48-2.41 (m, 2H), 2.30 (s, 3H), 2.26 (s, 3H). |

US 11,345,710 B2

-continued

| Example | Ar₁ | Ar₂ | LC-MS (ESI) | ¹H NMR |
|---|---|---|---|---|
| 23 | 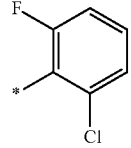 | 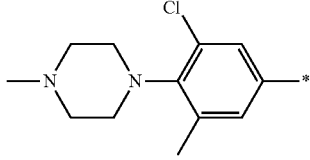 | (M + H)⁺ 553.18 | DMSO-d₆: δ 10.78 (brs, 1H), 9.23 (s, 1H), 8.18-7.88 (m, 1H), 7.86-7.81 (m, 1H), 7.74 (d, J = 8.2 Hz, 1H), 7.70-7.57 (m, 2H), 7.54-7.47 (m, 2H), 3.36 (t, J = 9.2 Hz, 2H), 2.87-2.79 (m, 2H), 2.65-2.56 (m, 2H), 2.33 (s, 3H), 2.30-2.22 (m, 5H). |
| 24 | 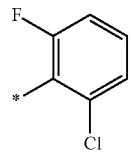 | 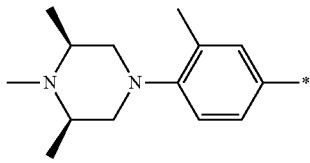 [SMILES: *c1ccc(N2C[C@@H](C)N(C)[C@@H](C)C2)c(C)c1] | (M + H)⁺ 547.25 | CDCl₃: δ 9.32 (s, 1H), 7.85-7.72 (m, 1H), 7.64-7.58 (m, 1H), 7.53-7.36 (m, 4H), 7.36-7.30 (m, 1H), 7.13-7.04 (m, 1H), 6.84 (s, 1H), 3.04-2.94 (m, 2H), 2.92-2.59 (m, 4H), 2.52 (s, 3H), 2.34 (s, 3H), 1.40-1.10 (m, 6H). |
| 25 |  | 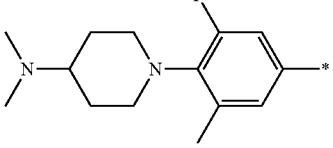 | (M + H)⁺ 565.27 | DMSO-d6: δ 10.80 (brs, 1H), 9.22 (s, 1H), 8.08-7.79 (m, 2H), 7.74 (d, J = 8.2 Hz, 1H), 7.70-7.65 (m, 1H), 7.54-7.47 (m, 2H), 7.42 (s, 1H), 3.07-2.98 (m, 4H), 2.69-2.60 (m, 1H), 2.45 (s, 6H), 2.30 (s, 3H), 1.92-1.86 (m, 2H), 1.64-1.54 (m, 2H). |
| 26 | 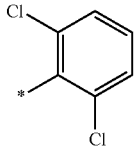 | 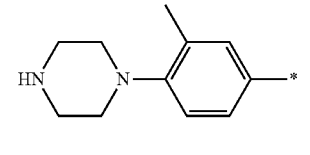 [SMILES: *c1ccc(N2CCNCC2)c(C)c1] | (M + H)⁺ 521.16 | CDCl₃: δ 9.34 (s, 1H), 7.65-7.60 (m, 2H), 7.60-7.50 (m, 2H), 7.49-7.42 (m, 2H), 7.11 (d, J = 8.5 Hz, 1H), 6.79 (d, J = 1.0 Hz, 1H), 3.36-3.30 (m, 4H), 3.18-3.11 (m, 4H), 2.35 (s, 3H). |
| 27 | 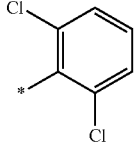 [SMILES: *c1c(Cl)cccc1Cl] | 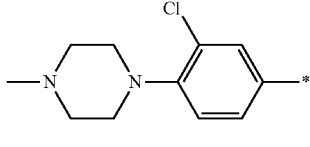 | (M + H)⁺ 555.36 | CDCl₃: δ 9.36 (s, 1H), 7.78-7.75 (m, 1H), 7.63-7.60 (m, 2H), 7.60-7.51 (m, 2H), 7.47-7.45 (m, 1H), 7.13 (d, J = 8.8 Hz, 1H), 6.78 (d, J = 1.2 Hz, 1H), 3.23-3.13 (m, 4H), 2.85-2.70 (m, 4H), 2.48 (s, 3H). |
| 28 | 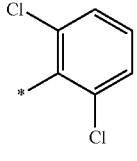 | 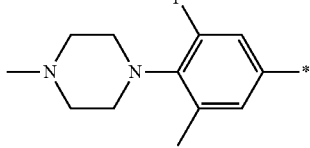 | (M + H)⁺ 553.06 | CDCl₃: δ 9.38 (s, 1H), 7.82-7.74 (m, 1H), 7.64-7.61 (m, 2H), 7.58-7.54 (m, 1H), 7.48-7.44 (m, 1H), 7.12-7.05 (m, 1H), 6.79 (d, J = 1.0 Hz, 1H), 3.44-3.18 (m, 4H), 3.10-2.86 (m, 4H), 2.68 (s, 3H), 2.36 (s, 3H). |
| 29 | 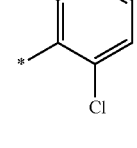 | 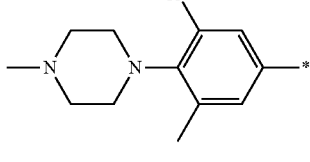 | (M + H)⁺ 569.28 | CDCl₃: δ 9.38 (s, 1H), 7.76 (br s, 1H), 7.72-7.67 (m, 1H), 7.64-7.58 (m, 2H), 7.58-7.52 (m, 1H), 7.46 (d, J = 0.9 Hz, 1H), 7.37-7.27 (m, 1H), 6.78 (d, J = 1.2 Hz, 1H), 3.64-3.56 (m, 2H), 3.19-3.09 (m, 2H), 3.00-2.93 (m, 2H), 2.80-2.70 (m, 2H), 2.58 (s, 3H), 2.39 (s, 3H). |
| 30 | 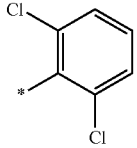 | 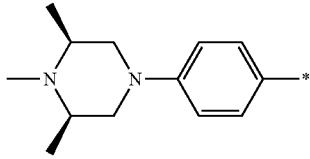 [SMILES: *c1ccc(N2C[C@@H](C)N(C)[C@@H](C)C2)cc1] | (M + H)⁺ 549.18 | CDCl₃: δ 9.32 (s, 1H), 7.84-7.71 (m, 2H), 7.64-7.60 (m, 2H), 7.58-7.51 (m, 2H), 7.45 (s, 1H), 7.01-6.94 (m, 2H), 6.77 (d, J = 1.1 Hz, 1H), 3.54-3.48 (m, 2H), 3.04-2.76 (m, 4H), 2.57 (s, 3H), 1.38 (s, 6H). |

-continued

| Example | Ar₁ | Ar₂ | LC-MS (ESI) | ¹H NMR |
|---|---|---|---|---|
| 31 | 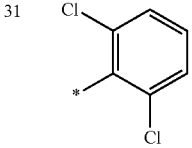 | 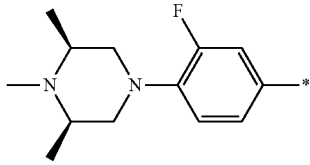 [SMILES: *c1ccc(N2C[C@@H](C)N(C)[C@@H](C)C2)c(F)c1] | (M + H)⁺ 567.30 | CDCl₃: δ 9.35 (s, 1H), 7.89-7.82 (m, 1H), 7.78-7.49 (m, 5H), 7.46 (s, 1H), 7.01-6.95 (m, 1H), 6.78 (d, J = 1.1 Hz, 1H), 3.33-3.28 (m, 2H), 2.94-2.79 (m, 4H), 2.53 (s, 3H), 1.35-1.28 (m, 6H). |
| 32 | 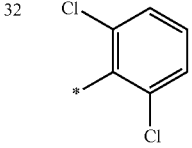 | 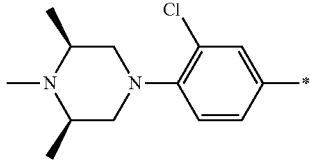 | (M + H)⁺ 583.21 | CDCl₃: δ 9.36 (s, 1H), 7.82-7.76 (m, 2H), 7.64-7.60 (m, 2H), 7.60-7.49 (m, 2H), 7.46 (s, 1H), 7.11 (d, J = 8.6 Hz, 1H), 6.78 (d, J = 1.0 Hz, 1H), 3.29-3.24 (m, 2H), 2.94-2.74 (m, 4H), 2.54 (s, 3H), 1.37-1.26 (m, 6H). |
| 33 | 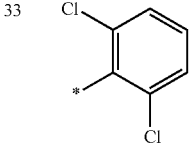 | 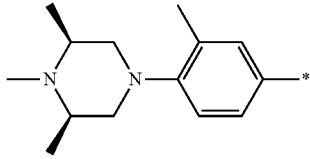 [SMILES: *c1ccc(N2C[C@@H](C)N(C)[C@@H](C)C2)c(C)c1] | (M + H)⁺ 563.28 | CDCl₃: δ 9.33 (s, 1H), 7.92-7.67 (m, 2H), 7.63-7.60 (m, 2H), 7.57-7.54 (m, 1H), 7.45 (s, 1H), 7.42-7.38 (m, 1H), 7.09 (d, J = 7.8 Hz, 1H), 6.77 (d, J = 1.0 Hz, 1H), 3.00-2.96 (m, 2H), 2.89-2.67 (m, 4H), 2.50 (s, 3H), 2.35 (s, 3H), 1.31-1.23 (m, 6H). |
| 34 | 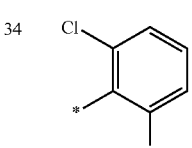 | 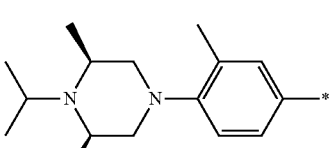 | (M + H)⁺ 591.18 | CDCl₃: δ 9.33 (s, 1H), 7.81-7.70 (m, 1H), 7.65-7.59 (m, 2H), 7.57-7.52 (m, 1H), 7.46-7.37 (m, 2H), 7.15-7.06 (m, 1H), 6.77 (d, J = 1.2 Hz, 1H), 3.35-3.09 (m, 3H), 3.05-2.90 (m, 2H), 2.85-2.67 (m, 2H), 2.38 (s, 3H), 1.34-1.01 (m, 12H). |
| 35 | 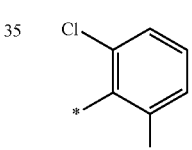 | 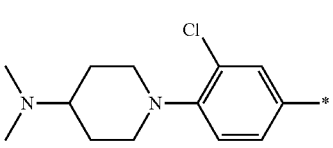 | (M + H)⁺ 583.27 | CDCl₃: δ 9.36 (s, 1H), 7.79-7.70 (m, 2H), 7.64-7.60 (m, 2H), 7.58-7.53 (m, 1H), 7.48-7.45 (m, 1H), 7.09 (d, J = 8.3 Hz, 1H), 6.78 (d, J = 1.1 Hz, 1H), 3.51-3.46 (m, 2H), 2.91-2.85 (m, 1H), 2.75-2.69 (m, 2H), 2.61 (s, 6H), 2.14-2.08 (m, 2H), 1.93-1.85 (m, 2H). |
| 36 | 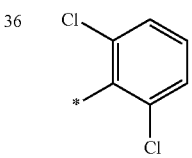 | 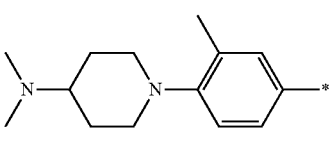 | (M + H)⁺ 563.32 | CDCl₃: δ 9.33 (s, 1H), 7.79-7.70 (m, 1H), 7.64-7.59 (m, 2H), 7.57-7.53 (m, 1H), 7.46-7.44 (m, 1H), 7.37 (d, J = 2.4 Hz, 1H), 7.09-7.04 (m, 1H), 6.77 (d, J = 1.1 Hz, 1H), 3.25-3.19 (m, 2H), 2.78-2.67 (m, 3H), 2.59 (s, 6H), 2.34 (s, 3H), 2.14-2.08 (m, 2H), 1.86-1.80 (m, 2H). |
| 37 | 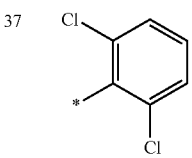 | 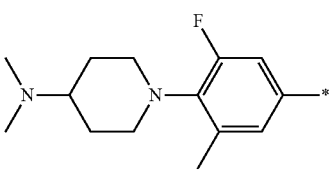 [SMILES: *c1cc(C)c(N2CCC(N(C)C)CC2)c(F)c1] | (M + H)⁺ 581.10 | CDCl₃: δ 9.37 (s, 1H), 7.89-7.78 (m, 1H), 7.64-7.60 (m, 2H), 7.58-7.54 (m, 1H), 7.47-7.43 (m, 1H), 7.10-7.02 (m, 1H), 6.78 (d, J = 1.1 Hz, 1H), 3.19 (t, J = 11.9 Hz, 2H), 3.09-3.03 (m, 2H), 2.79-2.71 (m, 1H), 2.58 (s, 6H), 2.34 (s, 3H), 2.06-1.99 (m, 2H), 1.80-1.70 (m, 2H). |

-continued

| Example | Ar₁ | Ar₂ | LC-MS (ESI) | ¹H NMR |
|---|---|---|---|---|
| 38 | 2,6-dichlorophenyl | 2-chloro-6-methoxy-4-(4-(dimethylamino)piperidin-1-yl)phenyl | (M + H)⁺ 613.21 | CDCl₃: δ 9.36 (s, 1H), 7.79-7.71 (m, 1H), 7.65-7.60 (m, 2H), 7.58-7.54 (m, 1H), 7.45 (d, J = 1.1 Hz, 1H), 7.21-7.15 (m, 1H), 6.78 (d, J = 1.2 Hz, 1H), 3.91 (s, 3H), 3.30-3.23 (m, 2H), 3.10-3.02 (m, 2H), 2.69-2.61 (m, 1H), 2.50 (s, 6H), 1.96-1.92 (m, 2H), 1.78-1.73 (m, 2H). |
| 39 | 2,6-dichlorophenyl | 2-fluoro-4-(1-methylpiperidin-4-yl)phenyl | (M + H)⁺ 538.35 | CDCl₃: δ 9.37 (s, 1H), 8.15-7.98 (m, 1H), 7.77-7.68 (m, 1H), 7.64-7.61 (m, 2H), 7.58-7.55 (m, 1H), 7.46 (s, 1H), 7.34-7.27 (m, 2H), 6.79 (d, J = 1.0 Hz, 1H), 3.24-3.18 (m, 2H), 2.97-2.90 (m, 1H), 2.50 (s, 3H), 2.40-2.33 (m, 2H), 2.08-2.03 (m, 2H), 1.93-1.90 (m, 2H). |
| 40 | 2,6-dichlorophenyl | 2-chloro-4-(1-methylpiperidin-4-yl)phenyl | (M + H)⁺ 554.26 | CDCl₃: δ 9.39 (s, 1H), 8.06-7.94 (m, 2H), 7.65-7.61 (m, 2H), 7.60-7.52 (m, 2H), 7.47 (s, 1H), 7.41 (d, J = 8.4 Hz, 1H), 6.79 (s, 1H), 3.66 (d, J = 11.2 Hz, 2H), 3.29-3.23 (m, 1H), 2.94-2.82 (m, 5H), 2.58-2.48 (m, 2H), 2.09-2.03 (m, 2H). |
| 41 | 2,6-dichlorophenyl | 2-methyl-4-(1-methylpiperidin-4-yl)phenyl | (M + H)⁺ 534.18 | CDCl₃: δ 13.15 (s, 1H), 9.35 (s, 1H), 7.89-7.83 (m, 1H), 7.64-7.59 (m, 2H), 7.58-7.51 (m, 2H), 7.48-7.45 (m, 1H), 7.31 (d, J = 8.6 Hz, 1H), 6.78 (s, 1H), 3.75-3.68 (m, 2H), 2.97-2.79 (m, 6H), 2.44-2.31 (m, 5H), 2.01-1.93 (m, 2H). |
| 42 | 2,6-dichlorophenyl | 2-fluoro-6-methyl-4-(1-methylpiperidin-4-yl)phenyl | (M + H)⁺ 552.30 | CDCl₃: δ 9.37 (s, 1H), 8.01-7.82 (m, 1H), 7.64-7.61 (m, 2H), 7.59-7.52 (m, 2H), 7.46 (s, 1H), 7.07 (s, 1H), 6.78 (s, 1H), 3.13-3.08 (m, 2H), 2.83-2.75 (m, 1H), 2.42 (s, 3H), 2.40 (s, 3H), 2.37-2.32 (m, 2H), 2.22-2.16 (m, 2H), 1.71-1.67 (m, 2H). |
| 43 | 2,6-dichlorophenyl | 2,4,4,5-tetrasubstituted tetrahydroisoquinoline | (M + H)⁺ 534.27 | DMSO-d₆: δ 9.19 (s, 1H), 7.92-7.83 (m, 3H), 7.80-7.76 (m, 1H), 7.50-7.47 (m, 2H), 7.43-7.42 (m, 1H), 3.48 (s, 2H), 2.45 (s, 3H), 2.35-2.28 (m, 5H), 1.34 (s, 6H). |
| 44 | 2,6-dichlorophenyl | 2,5-dimethyl-1,2,3,4-tetrahydroisoquinolin-7-yl | (M + H)⁺ 506.10 | CDCl₃: δ 9.35 (s, 1H), 7.81-7.75 (m, 1H), 7.66-7.57 (m, 3H), 7.57-7.52 (m, 1H), 7.47-7.44 (m, 1H), 6.78 (d, J = 1.1 Hz, 1H), 3.96 (s, 2H), 3.11-3.04 (m, 2H), 2.95-2.90 (m, 2H), 2.69 (s, 3H), 2.29 (s, 3H). |

| Example | Ar₁ | Ar₂ | LC-MS (ESI) | ¹H NMR |
|---|---|---|---|---|
| 45 | Br, F substituted phenyl | methyl-substituted phenyl with piperidine-N(CH₃)₂ linker | (M + H)⁺ 591.22 | CDCl₃: δ 9.33 (s, 1H), 7.83-7.71 (m, 1H), 7.70-7.65 (m, 1H), 7.57-7.52 (m, 1H), 7.47-7.43 (m, 1H), 7.40-7.34 (m, 2H), 7.10-7.01 (m, 1H), 6.85-6.81 (m, 1H), 3.26-3.19 (m, 2H), 2.93-2.87 (m, 1H), 2.75-2.69 (m, 2H), 2.63 (s, 6H), 2.34 (s, 3H), 2.15-2.09 (m, 2H), 1.90-1.81 (m, 2H). |

Example 46

6-(2-bromo-6-chlorophenyl)-2-((3-methyl-4-(4-methylpiperazin-1-yl)phenyl)amino)imidazo[1,2-b]pyrimido[4,5-d]pyridazin-5 (6H)-one a) Preparation of ethyl 2-(methylthio)-4-((2,2-dimethoxyethyl)carbamoyl)pyrimidine-5-carboxylate: to the solution of 2-(methylthio)-5-(ethoxycarbonyl)pyrimidine-4-carboxylic acid (700 mg, 2.9 mmol) in DMF (10 mL), was added HATU (1.7 g, 4.3 mmol). After the reaction mixture was stirred at room temperature for 30 min, 2,2-dimethoxyethan-1-amine (914 mg, 8.7 mmol) was added, and the reaction mixture continued to stir at room temperature for 1 hour. To the reaction mixture was added EA (100 mL) and water (50 mL), the organic phase was separated out, and the aqueous phase was extracted with EA (100 mL). The organic layers were collected, dried with anhydrous sodium sulfate, and the organic solvent was removed under reduced pressure to give the crude product, which was purified by column chromatography (silica gel, DCM:methanol=20:1) to give the targeted compound (900 mg, 93% yield, yellow solid). LC-MS (ESI): m/z (M+H)⁺ 330.10.

b) Preparation of ethyl 2-(methylthio)-4-((2-oxoethyl)carbamoyl)pyrimidine-5-carboxylate: to the solution of ethyl 4-((2,2-dimethoxyethyl)carbamoyl)-2-(methylthio)pyrimidine-5-carboxylate (900 mg, 2.7 mmol) in DCM (9 mL) was added concentrated under reduced pressure hydrochloric acid (9 mL). The reaction mixture was stirred at 50° C. for 3 hours, and then cooled to room temperature. To the reaction liquor was added water (10 mL), the organic phase was separated out, and the aqueous phase was extracted with DCM (10 mL×2). The organic layers were collected, washed with saturated saline, dried with anhydrous sodium sulfate, and the organic solvent was removed under reduced pressure to give the crude product, which was used for the next step directly. LC-MS (ESI): m/z (M+H)⁺ 284.06.

c) Preparation of ethyl 2-(methylthio)-4-((2-(2-(2-bromo-6-chlorophenyl)hydrazinyl)ethyl)carbamoyl)pyrimidine-5-carboxylat: to the solution of ethyl 2-(methylthio)-4-((2-oxoethyl)carbamoyl)pyrimidine-5-carboxylate (400 mg, 1.4 mmol) in methanol (10 mL) was added 2-bromo-6-chlorophenylhydrazine (309 mg, 1.4 mmol). The reaction mixture was stirred at room temperature for 30 min, and then to it was added sodium cyanoborohydride (86.8 mg, 1.4 mmol). The reaction mixture was stirred at 40° C. for 8 hours, and then to the reaction liquor was added DCM (20 mL) and water (20 mL), the organic phase was separated out, and the aqueous phase was extracted with DCM (20 mL) once. The organic layers were collected, washed with saturated saline, dried with anhydrous sodium sulfate, and the organic solvent was removed under reduced pressure to give the crude product, which was purified by column chromatography (DCM:methanol=10:1) to give the targeted compound (600 mg, 88% yield, yellow solid). LC-MS (ESI): m/z (M+H)⁺ 488.79.

d) Preparation of ethyl 2-(methylthio)-4-(1-((2-bromo-6-chlorophenyl)amino)-4,5-dihydro-1H-imidazol-2-yl)pyrimidine-5-carboxylate: to the solution of ethyl 4-((2-(2-(2-bromo-6-chlorophenyl)hydrazinyl)ethyl)carbamoyl)-2-(methylthio)pyrimidine-5-carboxylate (600 mg, 1.2 mmol) in DCM (10 mL) was added PCl₅ (374 mg, 1.8 mmol) at 0° C. The reaction mixture was stirred at room temperature for 30 min, and then cooled to 0° C. Methanol (10 mL) and sodium bicarbonate solid (600 mg) were added in sequence to quench the reaction, filtered, and removed the organic solvent under reduced pressure to give the crude product (650 mg), which was used for the next step directly. LC-MS (ESI): m/z (M+H)⁺ 470.77.

e) Preparation of ethyl 2-(methylthio)-4-(1-((2-bromo-6-chlorophenyl)amino)-1H-imidazol-2-yl)pyrimidine-5-carboxylate: at room temperature, ethyl 2-(methylthio)-4-(1-((2-bromo-6-chlorophenyl)amino)-4,5-dihydro-1H-imidazol-2-yl)pyrimidine-5-carboxylate (650 mg, crude product, equivalent) was dissolved in 1,4-dioxane (20 mL), and manganese dioxide (522 mg, 6.0 mmol) was added. The reaction mixture was stirred at 50° C. for 2 hours, cooled to room temperature, filtered, and concentrated by removing the organic solvent under reduced pressure to give the yellow crude product (600 mg), which was used for the next step directly. LC-MS (ESI): m/z (M+H)⁺ 468.75.

f) Preparation of 2-(methylthio)-6-(2-bromo-6-chlorophenyl)imidazo[1,2-b]pyrimido[4,5-d]pyridazin-5(6H)-one: at 0° C., to the solution of ethyl 2-(methylthio)-4-(1-((2-bromo-6-chlorophenyl)amino)-1H-imidazol-2-yl)pyrimidine-5-carboxylate (600 mg, crude product, equivalent) in DCM (20 mL) was added DBU (146 mg, 0.96 mmol). The reaction mixture was stirred at 0° C. for 5 min. Water (10 mL) was added, the organic phase was separated out, and the aqueous phase was extracted with DCM (10 mL). The organic layers were collected, washed with saturated saline, dried with anhydrous sodium sulfate, and concentrated by removing the organic solvent under reduced pressure to give the crude product, which was purified by column chromatography (silica gel, DCM:methanol=10:1) to give the targeted compound (380 mg, 75% yield for three steps, yellow solid). LC-MS (ESI): m/z (M+H)+422.69. ¹H NMR (400 MHz, CDCl₃): δ 9.38 (s, 1H), 7.79 (dd, J=8.1, 1.3 Hz, 1H), 7.67 (dd, J=8.2, 1.3 Hz, 1H), 7.52-7.48 (m, 2H), 6.81 (d, J=1.2 Hz, 1H), 2.78 (s, 3H).

g) Preparation of 6-(2-bromo-6-chlorophenyl)-2-((3-methyl-4-(4-methylpiperazin-1-yl)phenyl)amino)imidazo

[1,2-b]pyrimido[4,5-d]pyridazin-5(6H)-one: 2-(methyl-thio)-6-(2-bromo-6-chlorophenyl)imidazo[1,2-b]pyrimido[4,5-d]pyridazin-5(6H)-one (50 mg, 0.12 mmol) was dissolved in anhydrous DCM (20 mL). At 0° C., m-CPBA (31 mg, 0.18 mmol) to the reaction system, after addition, the temperature of the reaction liquor was increased to room temperature and stirred at room temperature for 5 min. Then the organic solvent was removed under reduced pressure to give the crude product. The crude product was dissolved in acetonitrile (20 mL), and 3-methyl-4-(4-methylpiperazin-1-yl)aniline (24.6 mg, 0.12 mmol) and TFA (0.05 mL) were added to the reaction system. The reaction liquor was heated to room temperature and stirred overnight, of which the value of pH was adjusted to 7-8 with saturated aqueous solution of sodium bicarbonate. DCM (20 mL) and water (10 mL) was added for liquid separation and extraction, and the aqueous phase was extracted with DCM (15 mL×2). The organic layers were collected, washed with saturated saline, dried with anhydrous sodium sulfate, filtered, and concentrated by removing the organic solvent under reduced pressure to give the crude product, which was purified by preparative liquid chromatography (column C18, 0-100% acetonitrile/water as mobile phase) to give the targeted compound (10 mg, 27% yield, yellow solid).

The compounds of Examples 47-50 were prepared from 2-(methylthio)-6-(2-bromo-6-chlorophenyl)imidazo[1,2-b]pyrimido[4,5-d]pyridazin-5(6H)-one and the corresponding substituted aniline using procedure similar to that described for the synthesis of compound of Example 46g.

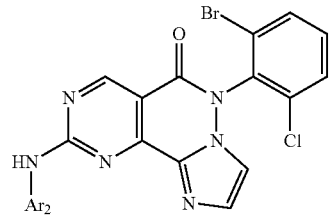

| Example | Ar₂ | LC-MS (ESI) | ¹H NMR |
|---|---|---|---|
| 46 | (4-methylpiperazin-1-yl)-2-methylphenyl | (M + H)⁺ 579.11 | MeOD: δ 9.23 (s, 1H), 8.05-7.84 (m, 2H), 7.80 (dd, J = 8.2, 1.2 Hz, 1H), 7.63 (t, J = 8.2 Hz, 1H), 7.55 (s, 1H), 7.46 (d, J = 1.3 Hz, 1H), 7.18 (d, J = 1.2 Hz, 1H), 7.15-7.09 (m, 1H), 3.02-2.94 (m, 4H), 2.74-2.58 (m, 4H), 2.38 (s, 3H), 2.35 (s, 3H). |
| 47 | (4-methylpiperazin-1-yl)-2-chlorophenyl | (M + H)⁺ 599.05 | MeOD: δ 9.28 (s, 1H), 8.48 (s, 1H), 8.20-8.15 (m, 1H), 7.92 (dd, J = 8.2, 1.2 Hz, 1H), 7.81 (dd, J = 8.2, 1.2 Hz, 1H), 7.63 (t, J = 8.2 Hz, 1H), 7.48 (d, J = 1.3 Hz, 1H), 7.23-7.20 (m, 2H), 3.28-3.12 (m, 4H), 3.07-2.81 (m, 4H), 2.63 (s, 3H). |
| 48 | (dimethylamino-piperidin-1-yl)-2-chlorophenyl | (M + H)⁺ 627.09 | MeOD: δ 9.27 (s, 1H), 8.54 (s, 1H), 8.27-8.07 (m, 1H), 7.92 (dd, J = 8.2, 1.2 Hz, 1H), 7.80 (dd, J = 8.2, 1.2 Hz, 1H), 7.63 (t, J = 8.2 Hz, 1H), 7.48 (d, J = 1.3 Hz, 1H), 7.24-7.14 (m, 2H), 3.48-3.43 (m, 2H), 2.78-2.67 (m, 3H), 2.55 (s, 6H), 2.09-2.02 (m, 2H), 1.85-1.75 (m, 2H). |
| 49 | (dimethylamino-piperidin-1-yl)-2-methylphenyl | (M + H)⁺ 607.16 | MeOD: δ 9.20 (s, 1H), 8.03-7.81 (m, 2H), 7.78 (dd, J = 8.2, 1.0 Hz, 1H), 7.61 (t, J = 8.2 Hz, 1H), 7.50 (s, 1H), 7.46 (d, J = 1.2 Hz, 1H), 7.17 (d, J = 0.7 Hz, 1H), 7.06 (m, 1H), 3.17-3.12 (m, 2H), 2.68-2.62 (m, 2H), 2.35-2.32 (m, 10H), 1.99-1.94 (m, 2H), 1.71-1.63 (m, 2H). |
| 50 | (dimethylamino-piperidin-1-yl)-2-fluoro-6-methylphenyl | (M + H)⁺ 625.14 | DMSO-d₆: δ 10.81 (s, 1H), 9.24 (s, 1H), 8.32 (s, 1H), 8.13-7.93 (m, 2H), 7.92-7.87 (m, 1H), 7.69 (t, J = 8.2 Hz, 1H), 7.50 (s, 1H), 7.41 (s, 1H), 3.04-2.93 (m, 5H), 2.30 (s, 3H), 2.23 (s, 6H), 1.87-1.77 (m, 2H), 1.58-1.47 (m, 2H). |

The compounds of Examples 51-55 were prepared from 5-bromo-2-(methylthio)pyrimidine-4-carboxylic acid, 2,2-dimethoxyethan-1-amine, (2,6-disubstitutedphenyl)hydrazine, cuprous cyanide and the corresponding substituted aniline using procedure similar to those described for the synthesis of compound of Example 2.

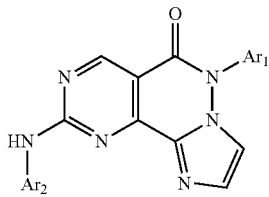

Example 56

6-(2,6-dichlorophenyl)-2-((3-chloro-4-(4-methylpiperazin-1-yl)phenyl)amino)-8-methylimidazo[1,2-b]pyrimido[4,5-d]pyridazin-5(6H)-one a) 5-bromo-2-(methylthio)-N-(2-oxopropyl)pyrimidine-4-carboxamide: at room temperature, to the solution of 5-bromo-2-(methylthio)pyrimidine-4-carboxylic acid (24.4 g, 98.5 mmol) in DMF (80.0 mL) was added DIPEA (31.9 g, 246.3 mmol), stirred for 1 min, and then HATU (46.9 g, 123.2 mmol) was added and the reaction mixture was stirred for 1 min, and finally 1-aminopropan-2-one hydrochloride (6.0 g, 82.1 mmol) was added. After replacement with nitrogen, the reaction liquor was stirred at room temperature for 4 h, the reaction liquor was poured into 500 mL of water, and extracted with DCM three times, and the aqueous phase

| Example | Ar$_1$ | Ar$_2$ | LC-MS (ESI) | $^1$H NMR |
|---|---|---|---|---|
| 51 | (2-methyl-6-fluorophenyl) | (2-chloro-4-(4-methylpiperazin-1-yl)phenyl) | (M + H)$^+$ 519.12 | CDCl$_3$: δ 9.37 (s, 1H), 7.84 (d, J = 2.5 Hz, 1H), 7.83-7.76 (m, 1H), 7.55-7.51 (m, 1H), 7.47-7.43 (m, 1H), 7.30-7.27 (m, 1H), 7.23-7.18 (m, 1H), 7.14 (d, J = 8.6 Hz, 1H), 6.85-6.82 (m, 1H), 3.39-3.30 (m, 4H), 3.24-3.03 (m, 4H), 2.72 (s, 3H), 2.25 (s, 3H). |
| 52 | (2-methyl-6-fluorophenyl) | (2-chloro-6-methyl-4-(4-methylpiperazin-1-yl)phenyl) | (M + H)$^+$ 533.05 | CDCl$_3$: δ 9.38 (s, 1H), 7.83-7.76 (m, 1H), 7.75-7.70 (m, 1H), 7.56-7.50 (m, 1H), 7.45 (d, J = 0.9 Hz, 1H), 7.35 (brs, 1H), 7.28 (d, J = 8.0 Hz, 1H), 7.23-7.18 (m, 1H), 6.84-6.82 (m, 1H), 3.71-3.57 (m, 2H), 3.31-3.11 (m, 4H), 3.04-2.89 (m, 2H), 2.73 (s, 3H), 2.39 (s, 3H), 2.25 (s, 3H). |
| 53 | (2-methyl-6-chlorophenyl) | (2-chloro-4-(4-methylpiperazin-1-yl)phenyl) | (M + H)$^+$ 535.28 | CDCl$_3$: δ 9.37 (s, 1H, 7.78 (d, J = 2.2 Hz, 2H), 7.53-7.44 (m, 3H), 7.40 (dd, J = 7.2, 1.4 Hz, 1H), 7.13 (d, J = 8.6 Hz, 1H), 6.74 (d, J = 1.1 Hz, 1H), 3.25-3.14 (m, 4H), 2.92-2.75 (m, 4H), 2.52 (s, 3H), 2.26 (s, 3H). |
| 54 | (2-methyl-6-chlorophenyl) | (2-fluoro-6-methyl-4-(4-methylpiperazin-1-yl)phenyl) | (M + H)$^+$ 533.24 | CDCl$_3$: δ 9.38 (s, 1H), 7.78-7.72 (m, 1H), 7.60 (brs, 1H), 7.51-7.44 (m, 3H), 7.41-7.38 (m, 1H), 7.11-7.05 (m, 1H), 6.74 (d, J = 1.1 Hz, 1H), 3.32-3.11 (m, 4H), 2.85-2.66 (m, 4H), 2.51 (s, 3H), 2.36 (s, 3H), 2.26 (s, 3H). |
| 55 | (2-methyl-6-chlorophenyl) | (2-chloro-6-methyl-4-(4-methylpiperazin-1-yl)phenyl) | (M + H)$^+$ 549.30 | CDCl$_3$: δ 9.38 (s, 1H), 7.75 (s, 1H), 7.69 (s, 1H), 7.54-7.43 (m, 3H), 7.41-7.38 (m, 1H), 7.37-7.27 (m, 1H), 6.74 (d, J = 0.9 Hz, 1H), 3.56 (t, J = 9.6 Hz, 2H), 3.07-2.97 (m, 2H), 2.89-2.81 (m, 2H), 2.62-2.53 (m, 2H), 2.47 (s, 3H), 2.39 (s, 3H), 2.26 (s, 3H). | was extracted with DCM twice. The organic layers were washed with saline, and concentrated by removing the organic solvent under reduced pressure to give the crude product, which was purified by column chromatography (silica gel, ethyl acetate: petroleum ether=0%-50%) to give the targeted compound (9.0 g, 36% yield, yellow solid). LC-MS (ESI): m/z (M+H)$^+$ 303.89.

b) 5-bromo-N-(2-(2-(2,6-dichlorophenyl)hydrazono)propyl)-2-(methylthio)pyrimidine-4-carboxamide: at room temperature, 5-bromo-2-(methylthio)-N-(2-oxopropyl)pyrimidine-4-carboxamide (2.2 g, 7.2 mmol), (2,6-dichlorophenyl)hydrazine hydrochloride (1.5 g, 7.2 mmol) and acetic acid (4 mL), sodium borohydride acetate (2.2 mg, 10.0 mmol) were added to 1,2-dichloroethane (50 mL). The reaction mixture was stirred at room temperature for 3 hours, and then the organic solvent was removed under reduced pressure to give the crude product. The crude product was dissolved in DCM (50 mL), saturated aqueous solution of sodium bicarbonate (100 mL) was added for liquid separation and extraction, and the aqueous phase was extracted with DCM (30 mL×2). The organic layers were collected, washed with saturated saline, dried with anhydrous sodium sulfate, and concentrated by removing the organic solvent under reduced pressure to give the crude product, which was used for the next step directly. LC-MS (ESI): m/z (M+H)$^+$ 461.97.

c) 5-bromo-N-(2-(2-(2,6-dichlorophenyl)hydrazinyl)propyl)-2-(methylthio)pyrimidine-4-carboxamide: at room temperature, to the solution of 5-bromo-N-(2-(2-(2,6-dichlorophenyl)hydrazono)propyl)-2-(methylthio)pyrimidine-4-carboxamide (4.0 g, 8.7 mmol) dissolved in the mixture solvent of DCM (20 mL) and methanol (150 mL) was added sodium borohydride (1.5 g, 39.1 mmol). The reaction mixture was stirred at room temperature for 3 hours, concentrated to dry and dissolved in DCM (50 mL), to which was added saturated aqueous solution of sodium bicarbonate (100 mL) for liquid separation, and the aqueous phase was extracted with DCM (30 mL×2). The organic layers were collected, washed with saturated saline, dried with anhydrous sodium sulfate, filtered, and concentrated by removing the organic solvent under reduced pressure to give the crude product, which was purified by column chromatography (silica gel, ethyl acetate: petroleum ether=0%-50%) to give the targeted product (1.8 g, 45% yield, yellow solid). LC-MS (ESI): m/z (M+H)$^+$ 463.97.

d) 2-(5-bromo-2-(methylthio)pyrimidin-4-yl)-N-(2,6-dichlorophenyl)-5-methyl-4,5-dihydro-1H-imidazol-1-amine: at room temperature, trifluoromethanesulfonic anhydride (610 mg, 2.16 mmol) was dissolved in DCM (10 mL), and triphenylphosphine (566 mg, 2.16 mmol) was added to the mixture at 0° C. After the reaction mixture was stirred at the temperature for 30 min, 5-bromo-N-(2-(2-(2,6-dichlorophenyl)hydrazinyl)propyl)-2-(methylthio)pyrimidine-4-carboxamide (5 mL) was dissolved and added to the reaction liquor, and the reaction liquor continued to stir at 0° C. for 2 hours. To the reaction liquor was added sodium bicarbonate solid, and stirred for 2 min, filtered, and the filtrate was used for the next step directly. LC-MS (ESI): m/z (M+H)$^+$ 465.92.

e) 2-(5-bromo-2-(methylthio)pyrimidin-4-yl)-N-(2,6-dichlorophenyl)-5-methyl-1H-imidazol-1-amine: at room temperature, 2-(5-bromo-2-(methylthio)pyrimidin-4-yl)-N-(2,6-dichlorophenyl)-5-methyl-4,5-dihydro-1H-imidazol-1-amine (the crude product liquor) and manganese dioxide (2.0 g, 10.0 mmol) were added to DCM (20 mL). The reaction mixture was stirred at room temperature for 10 hours, and then manganese dioxide was removed by filtration, and the organic solvent was removed under reduced pressure to give the crude product, which was purified by column chromatography (silica gel, EA:PE=0%-50%) to give the targeted compound (including 50% triphenylphosphine oxide) (500 mg, 40% yield, yellow solid). LC-MS (ESI): m/z (M+H)$^+$ 463.97.

f) 4-(1-((2,6-dichlorophenyl)amino)-5-methyl-1H-imidazol-2-yl)-2-methylthio) pyrimidine-5-carbonitrile: at room temperature, 2-(5-bromo-2-(methylthio)pyrimidin-4-yl)-N-(2,6-dichlorophenyl)-5-methyl-1H-imidazol-1-amine (1.0 g, 2.3 mmol) and cuprous cyanide (414 mg, 4.6 mmol) were added to 1,4-dioxane (15 mL). The reaction mixture was stirred at 80° C. for 20 hours, and then cooled to room temperature. The reaction liquor was poured into the mixture solution of ammonium hydroxide (15 mL) and saturated aqueous solution of ammonium chloride (85 mL), and extracted with EA (50 mL×3). The organic layers were collected, washed with saturated saline, dried with anhydrous sodium sulfate, and the organic solvent was removed under reduced pressure to give the crude product, which was purified by column chromatography (silica gel, EA:PE=0%-50%) to give the targeted product (140 mg, 15% yield, yellow solid). LC-MS (ESI): m/z (M+H)$^+$ 391.01.

g) 6-(2,6-dichlorophenyl)-8-methyl-2-(methylthio)imidazo[1,2-b]pyrimido[4,5-d]pyridazin-5(6H)-one: at room temperature, 4-(1-((2,6-dichlorophenyl)amino)-5-methyl-1H-imidazol-2-yl)-2-(methylthio)pyrimidine-5-carbonitrile (130 mg, 0.33 mmol) was added to dioxane solution of hydrochloride (4M, 40 mL). The reaction mixture was stirred at 80° C. for 15 hours, cooled to 50° C., and water (10 mL) was added. The reaction mixture was stirred at 50° C. for 2 hours, and then cooled to room temperature. The organic solvent was removed under reduced pressure, EA (20 mL) and water (10 mL) was added for liquid separation and extraction, and the aqueous phase was extracted with EA (15 mL×2). The organic layers were collected, washed with saturated saline, dried with anhydrous sodium sulfate, and the organic solvent was removed under reduced pressure to give the targeted product (100 mg, 77% yield, yellow solid). LC-MS (ESI): m/z (M+H)$^+$ 392.01.

h) 6-(2,6-dichlorophenyl)-2-((3-chloro-4-(4-methylpiperazin-1-yl)phenyl)amino)-8-methylimidazo[1,2-b]pyrimido[4,5-d]pyridazin-5(6H)-one: to the solution of 6-(2,6-dichlorophenyl)-8-methyl-2-(methylthio)imidazo[1,2-b]pyrimido[4,5-d]pyridazin-5(6H)-one (100 mg, 0.256 mmol) in anhydrous DCM (3 mL) was added m-CPBA (53 mg, 0.307 mmol) at 0° C. After addition, the reaction temperature was increased to room temperature, stirred at room temperature for 1 hour, and the organic solvent was removed under reduced pressure to give the crude product. The crude product was dissolved in acetonitrile (5 mL), and 3-chloro-4-(4-methylpiperazin-1-yl)aniline (70 mg, 0.307 mmol) and TFA (2 drops) were added to the reaction system. The temperature was increased to 50° C., the reaction liquor was stirred at 50° C. for 5 hours, and the value of pH was adjusted to 7-8 with saturated aqueous solution of sodium bicarbonate. DCM (50 mL) and water (30 mL) were added for liquid separation, the aqueous phase was extracted with DCM (30 mL×2). The organic layers were collected, washed with saturated saline, dried with anhydrous sodium sulfate, filtered, and concentrated by removing the organic solvent under reduced pressure to give the crude product, which was purified by preparative liquid chromatography (column C18, 0-100% acetonitrile/water as mobile phase) to give the targeted compound (89 mg, 64% yield, yellow solid).

Example 57

6-(2,6-dichlorophenyl)-2-((3-chloro-4-(4-methylpiperazin-1-yl)phenyl)amino)-9-methylimidazo[1,2-b]pyrimido[4,5-d]pyridazin-5(6H)-one a) 2-(5-bromo-2-(methylthio)pyrimidin-4-yl)-N-(2,6-dichlorophenyl)-4-methyl-1H-imidazol-1-amine: the compound was prepared from 5-bromo-2-(methylthio)pyrimidine-4-carboxylic acid, 1,1-dimethoxy-2-propylamine, and 2,6-dichlorophenylhydrazine using procedure similar to those described for the synthesis of compounds of Example 2 a-e.

b) 6-(2,6-dichlorophenyl)-9-methyl-2-(methylthio)imidazo[1,2-b]pyrimido[4,5-d]pyridazin-5(6H)-one: at room temperature, 2-(5-bromo-2-(methylthio)pyrimidin-4-yl)-N-(2,6-dichlorophenyl)-4-methyl-1H-imidazol-1-amine (0.7 g, 1.57 mmol) and palladium acetate (0.071 g, 0.314 mmol) were added to DMF (10 mL). The reaction mixture was stirred at 60° C. for 20 hours, and cooled to room temperature. The solvent was removed under reduced pressure to give the crude product, which was purified by column chromatography (silica gel, EA:PE=0%-50%) to give the targeted product (0.3 g, 48.7% yield, yellow solid). LC-MS (ESI): m/z (M+H)$^+$ 392.01.

c) 6-(2,6-dichlorophenyl)-2-((3-chloro-4-(4-methylpiperazin-1-yl)phenyl)amino)-9-methylimidazo[1,2-b]pyrimido[4,5-d]pyridazin-5(6H)-one: the compound was prepared from 6-(2,6-dichlorophenyl)-9-methyl-2-(methylthio)imidazo[1,2-b]pyrimido[4,5-d]pyridazin-5 (6H)-one and 3-chloro-4-(4-methylpiperazin-1-yl)aniline using procedure similar to that described for the synthesis of compound of Example 2 h.

The compounds of Examples 58 and 59 were prepared from 6-(2,6-dichlorophenyl)-9-methyl-2-(methylthio)imidazo[1,2-b]pyrimido[4,5-d]pyridazin-5(6H)-one and 3-chloro-4-(4-methylpiperazin-1-yl)aniline using procedure similar to that described for the synthesis of compound of Example 2 h.

Example 60

6-(2,6-dichlorophenyl)-2-((3-methyl-4-(4-methylpiperazin-1-yl)phenyl)amino)-9-ethylimidazo[1,2-b]pyrimido[4,5-d]pyridazin-5(6H)-one a) 2-(5-bromo-2-(methylthio)pyrimidin-4-yl)-N-(2,6-dichlorophenyl)-4-ethyl-4,5-dihydro-1H-imidazol-1-amine: the compound was prepared from tert-butyl (1-oxobutan-2-yl) carbamate, 2,6-dichlorophenylhydrazine and 5-bromo-2-(methylthio)pyrimidine-4-carboxylic acid using procedure similar to those described for the synthesis of compounds of Example 1 a and 1 c-f.

b) 2-(5-bromo-2-(methylthio)pyrimidin-4-yl)-N-(2,6-dichlorophenyl)-4-ethyl-1H-imidazol-1-amine: the compound was prepared from 2-(5-bromo-2-(methylthio)pyrimidin-4-yl)-N-(2,6-dichlorophenyl)-4-ethyl-4,5-dihydro-1H-imidazol-1-amine using procedure similar to that described for the synthesis of compound of Example 2 e.

c) 6-(2,6-dichlorophenyl)-9-ethyl-2-(methylthio)imidazo[1,2-b]pyrimido[4,5-d]pyridazin-5(6H)-one: at room temperature, 2-(5-bromo-2-(methylthio)pyrimidin-4-yl)-N-(2,6-dichlorophenyl)-4-ethyl-1H-imidazol-1-amine (0.9 g, 1.96 mmol), cesium carbonate (1.9 g, 5.88 mmol), 1,3-bis(diphenylphosphatealkyl)propane (323 mg, 0.78 mmol) and palladium acetate (88 mg, 0.39 mmol) were added to dioxane (10 mL). The reaction mixture was stirred at 60° C. with a carbon monoxide balloon for 20 hours, and cooled to room temperature. The solvent was removed under reduced pressure to give the crude product, which was purified by column chromatography (silica gel, EA:PE=0%-50%) to give the targeted product (0.3 g, 48.7% yield, yellow solid). LC-MS (ESI): m/z (M+H)$^+$ 392.01.

d) 6-(2,6-dichlorophenyl)-2-((3-methyl-4-(4-methylpiperazin-1-yl)phenyl)amino)-9-ethylimidazo[1,2-b]pyrimido[4,5-d]pyridazin-5(6H)-one: the compound was prepared from 6-(2,6-dichlorophenyl)-9-ethyl-2-(methylthio)imidazo[1,2-b]pyrimido[4,5-d]pyridazin-5(6H)-one and 3-methyl4-(4-methylpiperazin-1-yl)aniline using procedure similar to that described for the synthesis of compound of Example 2 h.

The following compound of Example 61 was prepared from 6-(2,6-dichlorophenyl)-9-ethyl-2-(methylthio)imidazo[1,2-b]pyrimido[4,5-d]pyridazin-5(6H)-one and 3-methyl-4-(4-methylpiperazin-1-yl)aniline using procedure similar to that described for the synthesis of compound of Example 60 d.

The following compounds of Example 62 and 63 were prepared from tert-butyl (3-methyl-1-oxobutan-2-yl)carbamate, 2,6-dichlorophenylhydrazine, 5-bromo-2-(methylthio)pyrimidine-4-carboxylic acid and 3-methyl-4-(4-(dimethylamino)piperidin-1-yl)aniline using procedure similar to those described for the synthesis of compounds of Example 1a-f and 60 b-d.

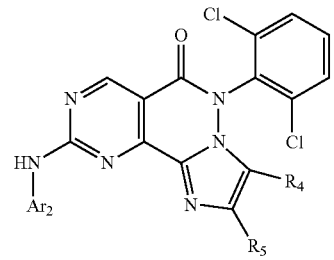

| Example | R$_4$ | R$_5$ | Ar$_2$ | LC-MS (ESI) | $^1$H NMR |
|---|---|---|---|---|---|
| 56 | CH$_3$ | H | ![2-chloro-4-(4-methylpiperazin-1-yl)phenyl] | (M + H)$^+$ 569.10 | DMSO-d$_6$: δ 10.79 (s, 1H), 9.19 (s, 1H), 8.28-8.13 (m, 1H), 8.00-7.88 (m, 1H), 7.85-7.81 (m, 2H), 7.77-7.72 (m, 1H), 7.32- (s, 1H), 7.25 (d, J = 8.6 Hz, 1H), 3.13-3.06 (m, 4H), 3.00-2.88 (m, 4H), 2.58 (s, 3H), 1.65 (s, 3H). |

-continued

| Example | R₄ | R₅ | Ar₂ | LC-MS (ESI) | ¹H NMR |
|---|---|---|---|---|---|
| 57 | H | CH₃ | 4-(4-methylpiperazin-1-yl)-3-chlorophenyl | (M + H)⁺ 569.28 | DMSO-d₆: δ 10.74 (brs, 1H), 9.20 (s, 1H), 8.19 (s, 1H), 8.01-7.93 (m, 1H), 7.90-7.84 (m, 2H), 7.80-7.75 (m, 1H), 7.26-7.16 (m, 2H), 3.60-3.44 (m, 4H), 3.01-2.92 (m, 4H), 2.30-2.18 (m, 6H). |
| 58 | H | CH₃ | 4-(4-dimethylaminopiperidin-1-yl)-3-methylphenyl | (M + H)⁺ 577.35 | DMSO-d₆: δ 10.67-10.50 (m, 1H), 9.16 (s, 1H), 8.00-7.82 (m, 3H), 7.79-7.75 (m, 1H), 7.59-7.52 (m, 1H), 7.17 (s, 1H), 7.11-7.04 (m, 1H), 3.18-3.13 (m, 2H), 3.06-2.99 (m, 1H), 2.69-2.62 (m, 8H), 2.28 (s, 3H), 2.23 (s, 3H), 2.06-2.00 (m, 2H), 1.78-1.68 (m, 2H). |
| 59 | H | CH₃ | 4-(4-dimethylaminopiperidin-1-yl)-3-fluoro-5-methylphenyl | (M + H)⁺ 595.33 | DMSO-d₆: δ 10.82-10.69 (m, 1H), 9.21 (s, 1H), 8.07-7.86 (m, 3H), 7.80-7.75 (m, 1H), 7.38-7.34 (m, 1H), 7.20 (s, 1H), 3.06-2.99 (m, 4H), 2.62-2.56 (m, 1H), 2.42 (s, 6H), 2.30 (s, 3H), 2.24 (s, 3H), 1.91-1.85 (m, 2H), 1.63-1.54 (m, 2H). |
| 60 | H | CH₂CH₃ | 4-(4-methylpiperazin-1-yl)-3-methylphenyl | (M + H)⁺ 563.28 | CDCl₃: δ 9.32 (s, 1H), 7.82-7.72 (m, 1H), 7.63-7.59 (m, 2H), 7.56-7.52 (m, 1H), 7.51-7.35 (m, 2H), 7.09 (d, J = 8.6 Hz, 1H), 6.50 (s, 1H), 3.03-2.97 (m, 4H), 2.77-2.60 (m, 6H), 2.43 (s, 3H), 2.34 (s, 3H), 1.26 (t, J = 7.6 Hz, 3H). |
| 61 | H | CH₂H₃ | 4-(4-dimethylaminopiperidin-1-yl)-3-methylphenyl | (M + H)⁺ 591.21 | DMSO-d₆: δ 10.76-10.56 (m, 1H), 9.15 (s, 1H), 7.90-7.83 (m, 2H), 7.79-7.74 (m, 1H), 7.70-7.46 (m, 2H), 7.17 (s, 1H), 7.04 (d, J = 8.1 Hz, 1H), 3.11-3.05 (m, 2H), 2.67-2.55 (m, 4H), 2.34-2.19 (m, 10H), 1.89-1.82 (m, 2H), 1.60-1.51 (m, 2H), 1.18 (t, J = 7.6 Hz, 3H). |
| 62 | H | CH(CH₃)₂ | 4-(4-dimethylaminopiperidin-1-yl)-3-methylphenyl | (M + H)⁺ 605.34 | DMSO-d₆: δ 10.78-10.60 (m, 1H), 9.15 (s, 1H), 7.88-7.84 (m, 2H), 7.79-7.74 (m, 1H), 7.68-7.43 (m, 2H), 7.15 (s, 1H), 7.04 (d, J = 8.2 Hz, 1H), 3.12-3.06 (m, 2H), 2.94-2.88 (m, 1H), 2.64-2.57 (m, 2H), 2.42-2.30 (m, 7H), 2.26 (s, 3H), 1.93-1.86 (m, 2H), 1.63-1.54 (m, 2H), 1.20 (d, J = 6.9 Hz, 6H). |
| 63 | H | CH₂OH | 4-(4-methylpiperazin-1-yl)-3-methylphenyl | — | — |

Example 64

6-allyl-2-((3-methyl-4-(4-(dimethylamino)piperidin-1-yl)phenyl)amino)imidazo[1,2-b]pyrimido[4,5-d]pyridazin-5(6H)-one The compound was prepared by using the procedure similar to that described for the syntheses of compound of Example 2. M.W. 458.57.

Example 65

Determination of the Inhibitory Effect of 6-(2,6-dichlorophenyl)-2-((4-(4-methylpiperazin-1-yl)phenyl)amino)imidazo[1,2-b]pyrimido[4,5-d]pyridazin-5(6H)-one and Analogs on the Enzyme Activity of Wee1 Kinase by Using the Wee1 Kinase (h) Detection Method Wee1 kinase (h) was incubated with 20 mM Tris/HCl pH 8.5, 0.2 mM EDTA, 500 μM LSNLYHQGKFLQTFC-GSPLYRRR, 10 mM MgAcetate and 10 μM [γ-$^{33}$P]-ATP. Then the stock solution of all compounds under test with 50× concentration in 100% DMSO was added to make the final concentration of 1/0.1/0.01 μM, and then mixed the mixture well. The reaction was initiated by the addition of the Mg/ATP mix. After incubation for 40 minutes at room temperature, the reaction was stopped by the addition of phosphoric acid to a concentration of 0.5%. 10 μL of the reaction liquor was then spotted onto a P30 filtermat and washed four times in 0.425% phosphoric acid and once in methanol prior to drying and scintillation counting. Each compound sample was duplicated in duplicate. The negative control was lack of all the components of Wee1 enzyme, and the positive was addition of 30% phosphoric acid to terminate the reaction. The Wee1 inhibitor AZD1775 was detected at 10/0.01 μM at the same experiment condition.

Table 1 summarizes the inhibition data of compounds on Wee1 kinase (Inh %).

TABLE 1

The inhibitory effect of 6-(2,6-dichlorophenyl)-2-((4-(4-methylpiperazin-1-yl)phenyl)amino)imidazo[1,2-b]pyrimido[1,2-b]pyrimido[4,5-d]pyridazin-5(6H)-one and analogs thereof on the enzyme activity of Wee1 kinase

| Example | 1 | | | 2 | 3 | | |
|---|---|---|---|---|---|---|---|
| C (μm) | 1 | 0.1 | 0.01 | 1 | 1 | 0.1 | 0.01 |
| Inh. (%) | 94 | 75 | 11 | 93 | 96 | 76 | 26 |
| Example | 4 | | | 7 | 9 | | |
| C (μm) | 1 | 0.1 | 0.01 | 1 | 1 | | 0.01 |
| Inh. (%) | 96 | 73 | 16 | 92 | 97 | | 14 |
| Example | 11 | | | 12 | 13 | | |
| C (μm) | | 1 | | 1 | 1 | | |
| Inh. (%) | | 93 | | 96 | 85 | | |
| Example | 14 | | | 15 | 16 | | |
| C (μm) | 1 | | 1 | 1 | 0.1 | | 0.01 |
| Inh. (%) | 93 | | 87 | 93 | 73 | | 22 |
| Example | 17 | | | 18 | 19 | | |
| C (μm) | 1 | 0.1 | 0.01 | 1 | 1 | | |
| Inh. (%) | 96 | 56 | 5 | 87 | 92 | | |
| Example | 20 | | | 21 | 22 | | |
| C (μm) | 1 | | | 1 | 1 | | 0.01 |
| Inh. (%) | 77 | | | 95 | 95 | | 21 |
| Example | 23 | | | 25 | 26 | | |
| C (μm) | 1 | | | 1 | 0.01 | | 0.01 |
| Inh. (%) | 91 | | | 96 | 10 | | 27 |
| Example | 27 | | | 28 | 29 | | |
| C (μm) | 1 | 0.1 | 0.01 | 1 | 0.01 | 1 | 0.1 | 0.01 |
| Inh. (%) | 97 | 76 | 17 | 95 | 15 | 93 | 65 | 21 |
| Example | 34 | | | 35 | 36 | | |
| C (μm) | 0.01 | | 1 | 0.01 | 1 | | 0.01 |
| Inh. (%) | 21 | | 96 | 4 | 98 | | 22 |
| Example | 37 | | | 38 | 43 | | |
| C (μm) | 1 | | | 0.01 | 0.01 | | 0.01 |
| Inh. (%) | 96 | | | 13 | 11 | | 9 |
| Example | 44 | | | 45 | 46 | | |
| C (μm) | 0.01 | | | 0.01 | 1 | | 0.01 |
| Inh. (%) | 4 | | | 12 | 92 | | 17 |
| Example | 47 | | | 48 | 49 | | |
| C (μm) | 1 | | | 1 | 0.01 | | 1 |
| Inh. (%) | 96 | | | 93 | 23 | | 91 |
| Example | 50 | | | 51 | 52 | | |
| C (μm) | 1 | | | 1 | 1 | | |
| Inh. (%) | 94 | | | 88 | 78 | | |
| Example | 53 | | | 54 | 55 | | |
| C (μm) | 1 | 0.1 | 0.01 | 1 | 1 | 0.1 | 0.01 |
| Inh. (%) | 94 | 69 | 12 | 91 | 89 | 46 | 0 |
| Example | 56 | | | 57 | 58 | | |
| C (μm) | 1 | | | 1 | 0.01 | | 0.01 |
| Inh. (%) | 95 | | | 93 | 12 | | 9 |
| Example | 59 | | | 61 | 62 | | |
| C (μm) | 0.01 | | | 0.01 | 0.01 | | |
| Inh. (%) | 7 | | | 12 | 7 | | |
| Example | AZD1775 | | | | | | |
| C (μm) | 10 | | | 0.01 | | | |
| Inh. (%) | 97 | | | 28 | | | |

In summary, as measure by Wee1 kinase (h) detection, 6-(2,6-dichlorophenyl)-2-((4-(4-methylpiperazin-1-yl)phenyl)amino)imidazo[1,2-b]pyrimido[4,5-d]pyridazin-5 (6H)-one (Example 1) and analogs thereof had good inhibitory effect on the activity of Wee1 kinase.

Example 66

Determination of the Cell Growth Inhibiting Activity of 6-(2,6-dichlorophenyl)-2-((4-(4-methylpiperazin-1-yl)phenyl)amino)imidazo[1,2-b]pyrimido[4,5-d]pyridazin-5(6H)-one and Analogs Thereof on LoVo Cells Using a MTT Based Cell Viability Assay The thawed LoVo cells were cultured and passaged to the third generation, and the growth state was good and the confluence was about 90%, which began to be used in the experiment. The LoVo cells were digested with trypsin, centrifuged at 800 rpm for 5 min, the supernatant was discarded, resuspended with fresh culture medium, and counted. 6000 Cells are seeded to each well of a 96-well cell culture plate. The cells were incubated at 37° C. in a 5% $CO_2$ cell culture incubator overnight. The tested sample (including the tested compound and the reference compound AZD1775) was diluted continuously to 8 concentrations (the last concentration was negative control of DMSO) with a 1:3 and 1:10 dilution in DMSO respectively: 10 μM, 3.3 μM, 1 μM, 0.33 μM, 0.1 μM, 0.033 μM, 0.01 μM, 0 μM (the final concentration of DMSO was 1%). 5 μL of each concentration was added to 120 μL of culture medium (25 times diluted), and the mixture was shaken well. The overnight cells were taken and the culture medium was removed, 195 μL of fresh culture medium was added to each well, and 5 μL of diluted culture medium containing the corresponding concentration of the tested sample was added respectively, and the culture plate was then placed in the 5% $CO_2$ cell culture incubator at 37° C. for 3 d. After removing the original solution and adding 100 μL of fresh serum-free DMEM culture medium containing MTT (0.5 mg/mL) per well, the culture was continued. The original solution was removed after 4 hrs and 100 μl DMSO was added to each well. The 96-well cell culture plates were shaken away from light for 10 min and readed in a multifunctional reader at 552/630/690 nm to give absorption values (OD values). The data were analyzed using a graphic software (Graph Pad Prism 5.0) and the inhibitory activity of the compound on cell proliferation was plotted in terms of cell survival and compound concentration. The $IC_{50}$ values were fitted by the S-shaped dose-response curve equation as follows: $Y=100/(1+10^{\wedge}(\text{Log C}-\text{Log IC}_{50}))$, where C was the concentration of testing compounds.

The inhibitory effect of compounds on the LoVo cell growth is expressed as $IC_{50}$ values and listed in Table 2.

TABLE 2

Growth inhibition of 6-(2,6-dichlorophenyl)-2-((4-(4-methylpiperazin-1-yl)phenyl)amino)imidazo[1,2-b]pyrimido[4,5-d]pyridazin-5(6H)-one and analogs thereof on LoVo cells

| Example | 1 | 2 | 3 | 4 | 7 | 9 |
|---|---|---|---|---|---|---|
| $IC_{50}$ (μm) | 0.5241 | 0.4055 | 0.2362 | 0.3394 | 0.8311 | 0.2130 |
| Example | 11 | 12 | 13 | 14 | 15 | 16 |
| $IC_{50}$ (μm) | 0.2660 | 0.8177 | 0.4878 | 0.8708 | 0.8316 | 0.4245 |
| Example | 17 | 18 | 19 | 20 | 21 | 22 |
| $IC_{50}$ (μm) | 0.9020 | 0.5788 | 0.4079 | 0.3636 | 0.2590 | 0.1378 |
| Example | 23 | 24 | 25 | 26 | 27 | 28 |
| $IC_{50}$ (μm) | 0.1946 | 0.3588 | 0.1438 | 0.2013 | 0.3695 | 0.2665 |
| Example | 29 | 30 | 31 | 32 | 33 | 34 |
| $IC_{50}$ (μm) | 0.2722 | 0.7787 | 0.8093 | 0.6794 | 0.3943 | 0.2364 |
| Example | 35 | 36 | 37 | 38 | 41 | 43 |
| $IC_{50}$ (μm) | 0.3020 | 0.2057 | 0.2906 | 0.4155 | 0.2122 | 0.4756 |
| Example | 44 | 45 | 46 | 47 | 48 | 49 |
| $IC_{50}$ (μm) | 0.3709 | 0.3331 | 0.2423 | 0.3703 | 0.2268 | 0.2722 |
| Example | 50 | 51 | 52 | 53 | 54 | 55 |
| $IC_{50}$ (μm) | 0.3235 | 0.9979 | 0.7562 | 0.6420 | 0.6368 | 0.5605 |
| Example | 56 | 57 | 58 | 59 | 60 | 61 |
| $IC_{50}$ (μm) | 0.4338 | 0.2693 | 0.2421 | 0.2848 | 0.3254 | 0.3516 |
| Example | 62 | | | AZD1775 | | |
| $IC_{50}$ (μm) | 0.6202 | | | 0.1545 | | |

In summary, as measured by the determination of MTT method, 6-(2,6-dichlorophenyl)-2-((4-(4-methylpiperazin-1-yl)phenyl)amino)imidazo[1,2-b]pyrimido[4,5-d]pyridazin-5 (6H)-one (Example 1) and its analogs have shown inhibitory effect on the growth of LoVo cells.

Example 67

Determination of the Cell Growth Inhibiting Activity of 6-(2,6-dichlorophenyl)-2-((4-(4-methylpiperazin-1-yl)phenyl)amino)imidazo[1,2-b]pyrimido[4,5-d]pyridazin-5(6H)-one and Analogs on NCI-H1299 Cells Using a MTT Based Cell Viability Assay The thawed NCI-H1299 cells were cultured and passaged to the third generation, and the growth state was good and the confluence was about 90%, which began to be used in the experiment. The NCI-H1299 cells were digested with trypsin, centrifuged at 800 rpm for 5 min, the supernatant was discarded, resuspended with fresh culture medium, and counted. 1000 Cells are seeded to each well of a 96-well plate. The cells are incubated at 37° C. in a 5% $CO_2$ cell culture incubator overnight. The tested sample (including the tested compound and the reference compound AZD1775) was diluted continuously to 8 concentrations (the last concentration was negative control of DMSO) with a 1:3 and 1:10 dilution in DMSO respectively: 10 μM, 3.3 μM, 1 μM, 0.33 μM, 0.1 μM, 0.033 μM, 0.01 μM, 0 μM (the final concentration of DMSO was 1%). 5 μL of each concentration was added to 120 μL of culture medium (25 times diluted), and the mixture was shaken well. The overnight cells were taken and the culture medium was removed, 195 μL of fresh culture medium was added to each well, and 5 μL of diluted culture medium containing the corresponding concentration of the tested sample was added respectively, and the culture plate was then placed in the 5% $CO_2$ cell culture incubator at 37° C. for 3 d. After removing the original solution and adding 100 μL of fresh serum-free DMEM culture medium containing MTT (0.5 mg/mL) per well, the culture was continued. The original solution was removed after 4 hrs and 100 μl DMSO was added to each well. The 96-well cell culture plates were shaken away from light for 10 min and read in a multifunctional reader at 552/630/690 nm to give absorption values (OD values). The data were analyzed using a graphic software (Graph Pad Prism 5.0) and the inhibitory activity of the compound on cell proliferation was plotted in terms of cell survival and compound concentration. The $IC_{50}$ values were fitted by the S-shaped dose-response curve equation as follows: $Y=100/(1+10^{(Log\,C-Log\,IC_{50})})$, where C was the concentration of testing compounds.

The inhibitory effect of compounds on the NCI-H1299 cell growth is expressed as $IC_{50}$ values and listed in Table 3.

TABLE 3

Growth inhibition of 6-(2,6-dichlorophenyl)-2-((4-(4-methylpiperazin-1-yl)phenyl)amino)imidazo[1,2-b]pyrimido[4,5-d]pyridazin-5(6H)-one ($IC_{50}$) and analogs thereof on NCI-H1299 cells

| Example | 1 | 2 | 3 | 4 | 7 | 9 |
|---|---|---|---|---|---|---|
| $IC_{50}$ (μm) | 0.9163 | 0.6516 | 0.1785 | 0.3831 | 0.7810 | 0.2836 |
| Example | 11 | 12 | 13 | 14 | 15 | 16 |
| $IC_{50}$ (μm) | 0.5554 | 0.4449 | 0.7379 | 0.5868 | 0.9044 | 0.3646 |
| Example | 17 | 18 | 19 | 20 | 21 | 22 |
| $IC_{50}$ (μm) | 0.8020 | 1.080 | 0.7434 | 0.5973 | 0.5113 | 0.3755 |
| Example | 23 | 24 | 25 | 26 | 27 | 28 |
| $IC_{50}$ (μm) | 0.5282 | 0.3276 | 0.2493 | 0.2685 | 0.4696 | 0.2953 |
| Example | 29 | 30 | 31 | 32 | 33 | 34 |
| $IC_{50}$ (μm) | 0.4002 | 0.5082 | 0.6724 | 0.5146 | 0.2368 | 0.2194 |
| Example | 35 | 36 | 37 | 38 | 41 | 43 |
| $IC_{50}$ (μm) | 0.1818 | 0.1350 | 0.1866 | 0.9781 | 0.1844 | 0.1754 |
| Example | 44 | 45 | 46 | 47 | 48 | 49 |
| $IC_{50}$ (μm) | 0.1642 | 0.2703 | 0.2713 | 0.5622 | 0.2806 | 0.3372 |
| Example | 50 | 51 | 52 | 53 | 54 | 55 |
| $IC_{50}$ (μm) | 0.5006 | 1.217 | 0.8090 | 0.8088 | 0.4186 | 0.6626 |
| Example | 56 | 57 | 58 | 59 | 60 | 61 |
| $IC_{50}$ (μm) | 0.5402 | 0.1732 | 0.1510 | 0.2201 | 0.1606 | 0.1260 |
| Example | | 62 | | | AZD1775 | |
| $IC_{50}$ (μm) | | 0.1973 | | | 0.1165 | |

In summary, as measured by the determination of MTT method, 6-(2,6-dichlorophenyl)-2-((4-(4-methylpiperazin-1-yl)phenyl)amino)imidazo[1,2-b]pyrimido[4,5-d]pyridazin-5 (6H)-one (Example 1) and its analogs have shown inhibitory effect on the growth of NCI-H1299 cell.

Having now fully described this disclosure, it will be understood by those of ordinary skill in the art that the same can be performed within a wide and equivalent range of conditions, formulations and other parameters without affecting the scope of the disclosure or any embodiment thereof. All patents, patent applications and publications cited herein are fully incorporated by reference herein in their entirety.

What is claimed is:
1. A compound having the Formula I:

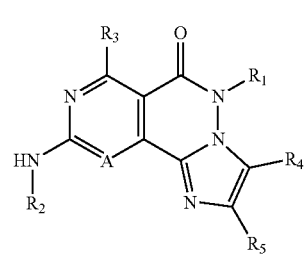

or a pharmaceutically acceptable salt thereof, wherein:
A is N;
$R_1$ is optionally substituted $C_{1-8}$ alkyl, optionally substituted $C_{2-8}$ alkenyl, optionally substituted $C_{3-8}$ cycloalkyl, optionally substituted $C_{6-14}$ aryl, or optionally substituted 5-14 membered heteroaryl, wherein the optional substituents on the $C_{1-8}$ alkyl, $C_{2-8}$ alkenyl, $C_{3-8}$ cycloalkyl, $C_{6-14}$ aryl, and 5-14 membered heteroaryl groups are one or more substituents selected from the group consisting of halo, hydroxy, carboxyl, amino, nitro, cyano, $C_1$-$C_6$ acylamino, $C_1$-$C_6$ acyloxy, $C_1$-$C_6$ alkoxy, aryloxy, alkylthio, $C_1$-$C_6$ alkyl, $C_1$-$C_6$ acyl, $C_6$-$C_{10}$ aryl, $C_3$-$C_8$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl($C_2$-$C_6$)alkynyl, saturated and unsaturated heterocyclic and heteroaryl, methylenedioxy, $C_1$-$C_6$ haloalkyl, $C_6$-$C_{10}$ aryl($C_1$-$C_6$)alkyl, $C_1$-$C_6$ hydroxyalkyl, ureido, thiol, azido, carbonyl, di($C_{1-10}$ alkyl)amino, alkylsulfonyl, aminosulfonyl, dialkylaminosulfonyl, and alkylsulfinyl;
$R_2$ is an optionally substituted heterocyclic group which is a saturated or partially saturated 3-7 membered monocyclic or 7-10 membered bicyclic ring system, optionally substituted $C_{6-14}$ aryl, or optionally substituted 5-14 membered heteroaryl, wherein the optional substituents on the monocyclic or bicyclic ring system, aryl, or heteroaryl groups are one or more substituents selected from the group consisting of halo, hydroxy, carboxyl, amino, nitro, cyano, $C_1$-$C_6$ acylamino, $C_1$-$C_6$ acyloxy, $C_1$-$C_6$ alkoxy, aryloxy, alkylthio, $C_1$-$C_6$ alkyl, $C_1$-$C_6$ acyl, $C_6$-$C_{10}$ aryl, $C_3$-$C_8$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl($C_2$-$C_6$)alkynyl, saturated and unsaturated heterocyclic and heteroaryl, methylenedioxy, $C_1$-$C_6$ haloalkyl, $C_6$-$C_{10}$ aryl($C_1$-$C_6$)alkyl, $C_1$-$C_6$ hydroxyalkyl, ureido, thiol, azido, carbonyl, di($C_{1-10}$ alkyl)amino, alkylsulfonyl, aminosulfonyl, dialkylaminosulfonyl, and alkylsulfinyl;
$R_3$-$R_5$ are independently H, halo, optionally substituted amino, optionally substituted alkoxy, optionally substituted $C_{1-10}$ alkyl, alkenyl, alkynyl, nitro, cyano, acylamido, hydroxy, thiol, acyloxy, azido, carboxy, ethylenedioxo, hydroxyacylamino or optionally substituted alkylthiol, wherein the optional substituents on the alkoxy, $C_{1-10}$ alkyl and alkylthiol groups are one or more substituents selected from the group consisting of halo, hydroxy, carboxyl, amino, nitro, cyano, $C_1$-$C_6$ acylamino, $C_1$-$C_6$ acyloxy, $C_1$-$C_6$ alkoxy, aryloxy, alkylthio, $C_1$-$C_6$ alkyl, $C_1$-$C_6$ acyl, $C_6$-$C_{10}$ aryl, $C_3$-$C_8$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl($C_2$-$C_6$)alkynyl, saturated and unsaturated heterocyclic and heteroaryl, methylenedioxy, $C_1$-$C_6$ haloalkyl, $C_6$-$C_{10}$ aryl($C_1$-$C_6$)alkyl, $C_1$-$C_6$ hydroxyalkyl, ureido, thiol, azido, carbonyl, di($C_{1-10}$ alkyl)amino, alkylsulfonyl, aminosulfonyl, dialkylaminosulfonyl, and alkylsulfinyl, and wherein the optional substituents on the amino groups are $C_{1-10}$ alkyl, cycloalkyl, aryl, heteroaryl, or amino.

2. The compound of claim 1, wherein A is N, $R_1$ and $R_2$ are each optionally substituted $C_{6-14}$ aryl, and $R_3$-$R_5$ is H.

3. The compound of claim 1, wherein said compound has Formula II:

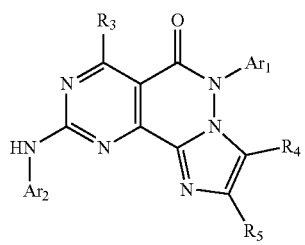

(II)

or pharmaceutically acceptable salts thereof, wherein:
$R_3$-$R_5$ are independently H, halo, optionally substituted amino, optionally substituted alkoxy, optionally substituted $C_{1-10}$ alkyl, alkenyl, alkynyl, nitro, cyano, acylamido, hydroxy, thiol, acyloxy, azido, carboxy, ethylenedioxo, hydroxyacylamino or optionally substituted alkylthio;
$Ar_1$ and $Ar_2$ are optionally substituted $C_{6-14}$ aryl or optionally substituted 5-14 membered heteroaryl.

4. The compound of claim 3, wherein $R_3$-$R_5$ are H or optionally substituted $C_{1-6}$ alkyl and $Ar_1$ and $Ar_2$ are each optionally substituted phenyl.

5. The compound of claim 1, wherein said compound is selected from the group consisting of:
- 6-(2-chloro-6-fluorophenyl)-2-((2,4,4-trimethyl-1,2,3,4-tetrahydroisoquinolin-7-yl)amino)imidazo[1,2-b]pyrimido[4,5-d]pyridazin-5(6H)-one;
- 6-(2,6-difluorophenyl)-2-((3-methyl-4-(4-methylpiperazin-1-yl)phenyl)amino)imidazo[1,2-b]pyrimido[4,5-d]pyridazin-5(6H)-one;
- 6-(2,6-dichlorophenyl)-2-((3-methyl-4-(4-methylpiperazin-1-yl)phenyl)amino)imidazo[1,2-b]pyrimido[4,5-d]pyridazin-5(6H)-one;
- 6-(2,6-dichlorophenyl)-2-((3,5-dimethyl-4-(4-methylpiperazin-1-yl)phenyl)amino)imidazo[1,2-b]pyrimido[4,5-d]pyridazin-5(6H)-one;
- 6-(2,6-dichlorophenyl)-2-((3-chloro-4-(4-methylpiperazin-1-yl)phenyl)amino)imidazo[1,2-b]pyrimido[4,5-d]pyridazin-5(6H)-one;
- 6-(2,6-dichlorophenyl)-2-((3-chloro-5-methyl-4-(4-methylpiperazin-1-yl)phenyl)amino)imidazo[1,2-b]pyrimido[4,5-d]pyridazin-5(6H)-one;
- 6-(2,6-dichlorophenyl)-2-((3,5-dimethyl-4-(4-methylpiperazin-1-yl)phenyl)amino)imidazo[1,2-b]pyrimido[4,5-d]pyridazin-5(6H)-one;
- 6-(2,6-dichlorophenyl)-2-dimethyl-4-(4-methylpiperazin-1-yl)phenyl)amino) imidazo[1,2-b]pyrimido[4,5-d]pyridazin-5(6H)-one;
- 6-(2-chloro-6-fluorophenyl)-2-((3-methyl-4-(4-methylpiperazin-1-yl)phenyl)amino)imidazo[1,2-b]pyrimido[4,5-d]pyridazin-5(6H)-one;
- 6-(2-chloro-6-fluorophenyl)-2-((3-chloro-5-methyl-4-(4-methylpiperazin-1-yl)phenyl)amino)imidazo[1,2-b]pyrimido[4,5-d]pyridazin-5(6H)-one;
- 6-(2-chloro-6-fluorophenyl)-2-((3,5-dimethyl-4-(4-methylpiperazin-1-yl)phenyl)amino)imidazo[1,2-b]pyrimido[4,5-d]pyridazin-5(6H)-one;
- 6-(2-chloro-6-fluorophenyl)-2-((2,4,4-trimethyl-1,2,3,4-tetrahydroisoquinolin-7-yl)amino)imidazo[1,2-b]pyrimido[4,5-d]pyridazin-5(6H)-one;
- 6-(2,6-difluorophenyl)-2(3,5 -dimethyl-4-(4-methylpiperazin -1-yl) phenyl)amino)imidazo[1,2-b]pyrimido[4,5-d]pyridazin-5(6H)-one;
- 6-(2-fluoro-6-methylphenyl)-2-((3-methyl-4-(4-methylpiperazin-1-yl)phenyl)amino)imidazo[1,2-b]pyrimido[4,5-d]pyridazin-5(6H)-one;
- 6-(2-fluoro-6-methylphenyl)-2-((3,5-dimethyl-4-(4-methylpiperazin-1-yl)phenyl)amino) imidazo[1,2-b]pyrimido[4,5-d]pyridazin-5(6H)-one;
- 6-(2-chloro-6-methylphenyl)-2-((3-methyl-4-(4-methylpiperazin-1-yl)phenyl)amino)imidazo[1,2-b]pyrimido[4,5-d]pyridazin-5(6H)-one;
- 6-(2-chloro-6-methylphenyl)-2-((3,5-dimethyl-4-(4-methylpiperazin-1-yl)phenyl)amino)imidazo[1,2-b]pyrimido[4,5-d]pyridazin-5(6H)-one;
- 6-(2,6-difluorophenyl)-2-((3-chloro-4-(4-methylpiperazin- 1-yl)phenyl)amino)imidazo[1,2-]pyrimido[4,5-d]pyridazin-5(6H)-one;
- 6-(2,6-difluorophenyl)-2-((3-fluoro-5-methyl-4-(4-methylpiperazin-1-yl)phenyl)amino)imidazo[1,2-b]pyrimido[4,5-d]pyridazin-5(6H)-one;
- 6-(2,6-difluorophenyl)-2-((3-chloro-5-methyl-4-(4-methylpiperazin-1-yl)phenyl)amino) imidazo[1,2-b]pyrimido[4,5-d]pyridazin-5(6H)-one;
- 6-(2-chloro-6-fluorophenyl)-2-((3-chloro-4-(4-methylpiperazin-1-yl)phenyl)amino)imidazo[1,2-b]pyrimido[4,5-d]pyridazin-5(6H)-one;
- 6-(2-chloro-6-fluorophenyl)-2-((3-fluoro-5-methyl-4-(4-methylpiperazin-1-yl)phenyl)amino)imidazo[1,2-b]pyrimido[4,5-d]pyridazin-5(6H)-one;
- 6-(2-chloro-6-fluorophenyl)-2-((3-chloro-5-methyl-4-(4-methylpiperazin-1-yl)phenyl)amino)imidazo[1,2-b]pyrimido[4,5-d]pyridazin-5(6H)-one;
- 6-(2-chloro-6-fluorophenyl)-2-((3-methyl-4-((3S,5R)-3,4,5-trimethylpiperazin-1-yl)phenyl)amino)imidazo[1,2-b]pyrimido[4,5-d]pyridazin-5(6H)-one;
- 6-(2-chloro-6-fluorophenyl)-2-((3-fluoro-5-methyl-(4-(4-(dimethylamino)piperidin-1-yl)phenyl)amino)imidazo[1,2-b]pyrimido[4,5-d]pyridazin-5(6H)-one;
- 6-(2,6-dichlorophenyl)-2-((3-methyl-4-(piperazin-1-yl)phenyl)amino)imidazo[1,2-b]pyrimido[4,5-d]pyridazin-5(6H)-one;
- 6-(2,6-dichlorophenyl)-2-((3-chloro-4-(4-methylpiperazin-1-yl)phenyl)amino)imidazo[1,2-b]pyrimido[4,5-d]pyridazin-5(6H)-one;
- 6-(2,6-dichlorophenyl)-2-((3-fluoro-5-methyl-4-(4-methylpiperazin- 1-yl)phenyl)amino)imidazo[1,2-b]pyrimido[4,5-d]pyridazin-5(6H)-one;
- 6-(2,6-dichlorophenyl)-2-((3-chloro-5-methyl-4-(4-methylpiperazin-1-yl)phenyl)amino)imidazo[1,2-b]pyrimido[4,5-d]pyridazin-5(6H)-one;
- 6-(2,6-dichlorophenyl)-2-((4-((3S,5R)-3,4,5-trimethylpiperazin-1-yl)phenyl)amino)imidazo[1,2-b]pyrimido[4,5-d]pyridazin-5(6H)-one;
- 6-(2,6-dichlorophenyl)-2-((3-fluoro-4(3S,5R)-3,4,5-trimethylpiperazin- 1-yl)phenyl)amino)imidazo[1,2-b]pyrimido[4,5-d]pyridazin-5(6H)-one;
- 6-(2,6-dichlorophenyl)-2-((3-chloro-4-((3S,5R)-3,4,5-trimethylpiperazin-1-yl)phenyl)amino)imidazo[1,2-b]pyrimido[4,5-d]pyridazin-5(6H)-one;

6-(2,6-dichlorophenyl)-2-((3-methyl-4-((3S,5R)-3,4,5-trimethylpiperazin-1-yl)phenyl)amino)imidazo[1,2-b]pyrimido[4,5-d]pyridazin-5(6H)-one;

6-(2,6-dichlorophenyl)-2-((3-methyl-4-((3S,5R)-4-isopropyl-3,5-dimethylpiperazin-1-yl)phenyl)amino)imidazo[1,2-b]pyrimido[4,5-d]pyridazin-5(6H)-one;

6-(2,6-dichlorophenyl)-2-((3-chloro-4-(4-(dimethylamino)piperidin-1-yl)phenyl)amino)imidazo[1,2-b]pyrimido[4,5-d]pyridazin-5(6H)-one;

6-(2,6-dichlorophenyl)-2-((3-methyl-4-(4-(dimethylamino)piperidin-1-yl)phenyl)amino)imidazo[1,2-b]pyrimido[4,5-d]pyridazin-5(6H)-one;

6-(2,6-dichlorophenyl)-2-((3-fluoro-5-methyl-4-(4-(dimethylamino)piperidin-1-yl)phenyl)amino)imidazo[1,2-b]pyrimido[4,5-d]pyridazin-5(6H)-one;

6-(2,6-dichlorophenyl)-2-((3-chloro-5-methoxy-4-(4-(dimethylamino)piperidin-1-yl)phenyl)amino)imidazo[1,2-b]pyrimido[4,5-d]pyridazin-5(6H)-one;

6-(2,6-dichlorophenyl)-2-((3-fluoro-4-(1-methylpiperidin-4-yl)phenyl)amino)imidazo[1,2-b]pyrimido[4,5-d]pyridazin-5(6H)-one;

6-(2,6-dichlorophenyl)-2-((3-chloro-4-(1-methylpiperidin-4-yl)phenyl)amino)imidazo[1,2-b]pyrimido[4,5-d]pyridazin-5(6H)-one;

6-(2,6-dichlorophenyl)-2-(3-methyl-4-(1-methylpiperidin-4-yl)phenyl)amino)imidazo[1,2-b]pyrimido[4,5-d]pyridazin-5(6H)-one;

6-(2,6-dichlorophenyl)-2-((3-fluoro-5-methyl-4-(1-methylpiperidin-4-yl)phenyl)amino)imidazo[1,2-b]pyrimido[4,5-d]pyridazin-5(6H)-one;

6-(2,6-dichlorophenyl)-2-((2,4,4,5-tetramethyl-1,2,3,4-tetrahydroisoquinolin-7-yl)amino)imidazo[1,2-b]pyrimido[4,5-d]pyridazin-5(6H)-one;

6-(2,6-dichlorophenyl)-2-((2,5-dimethyl-1,2,3,4-tetrahydroisoquinolin-7-yl)amino)imidazo[1,2-b]pyrimido[4,5-d]pyridazin-5(6H)-one;

6-(2-bromo-6-fluorophenyl)-2-((3-methyl-4-(4-(dimethylamino)piperidin-1-yl)phenyl)amino)imidazo[1,2-b]pyrimido[4,5-d]pyridazin-5(6H)-one;

6-(2-bromo-6-chlorophenyl)-2-((3-methyl-4-(4-methylpiperazin-1-yl)phenyl)amino)imidazo[1,2-b]pyrimido[4,5-d]pyridazin-5(6H)-one;

6-(2-bromo-6-chlorophenyl)-2-((3-chloro-4-(4-methylpiperazin-1-yl)phenyl)amino)imidazo[1,2-b]pyrimido[4,5-d]pyridazin-5(6H)-one;

6-(2-bromo-6-chlorophenyl)-2-((3-chloro-4-(4-(dimethylamino)piperidin-1-yl)phenyl)amino)imidazo[1,2-b]pyrimido[4,5-d]pyridazin-5(6H)-one;

6-(2-bromo-6-chlorophenyl)-2-((3-methyl-4-(4-(dimethylamino)piperidin-1-yl)phenyl)amino)imidazo[1,2-b]pyrimido[4,5-d]pyridazin-5(6H)-one;

6-(2-bromo-6-chlorophenyl)-2-((3-fluoro-5-methyl-4-(4-(dimethylamino)piperidin-1-yl)phenyl)amino)imidazo[1,2-b]pyrimido[4,5-d]pyridazin-5(6H)-one;

6-(2-fluoro-6-methylphenyl)-2-((3-chloro-4-(4-methylpiperazin-1-yl)phenyl)amino)imidazo[1,2-b]pyrimido[4,5-d]pyridazin-5(6H)-one;

6-(2-fluoro-6-methylphenyl)-2-((3-chloro-5-methyl-4-(4-methylpiperazin-1-yl)phenyl)amino)imidazo[1,2-b]pyrimido[4,5-d]pyridazin-5(6H)-one;

6-(2-chloro-6-methylphenyl)-2-((3-chloro-4-(4-methylpiperazin-1-yl)phenyl)amino)imidazo[1,2-b]pyrimido[4,5-d]pyridazin-5(6H)-one;

6-(2-chloro-6-methylphenyl)-2-((3-fluoro-5-methyl-4-(4-methylpiperazin-1-yl)phenyl)amino)imidazo[1,2-b]pyrimido[4,5-d]pyridazin-5(6H)-one;

6-(2-chloro-6-methylphenyl)-2-((3-chloro-5-methyl-4-(4-methylpiperazin-1-yl)phenyl)amino)imidazo[1,2-b]pyrimido[4,5-d]pyridazin-5(6H)-one;

6-(2,6-dichlorophenyl)-2-((3-chloro-4-(4-methylpiperazin-1-yl)phenyl)amino)-8-methylimidazo[1,2-b]pyrimido[4,5-d]pyridazin-5(6H)-one;

6-(2,6-dichlorophenyl)-2-((3-chloro-4-(4-methylpiperazin-1-yl)phenyl)amino)-9-methylimidazo[1,2-b]pyrimido[4,5-d]pyridazin-5(6H)-one;

6-(2,6-dichlorophenyl)-2-((3-methyl-4-(4-(dimethylamino)piperidin-1-yl)phenyl)amino)-9-methylimidazo[1,2-b]pyrimido[4,5-d]pyridazin-5(6H)-one;

6-(2,6-dichlorophenyl)-2-((3-fluoro-5-methyl-4-(4-(dimethylamino)piperidin-1-yl)phenyl)amino)-9-methylimidazo[1,2-b]pyrimido[4,5-d]pyridazin-5(6H)-one;

6-(2,6-dichlorophenyl)-2-((3-methyl-4-(4-methylpiperazin-1-yl)phenyl)amino)-9-ethylimidazo[1,2-b]pyrimido[4,5-d]pyridazin-5(6H)-one;

6-(2,6-dichlorophenyl)-2-((3-methyl-4-(4-(dimethylamino)piperidin-1-yl)phenyl)amino)-9-ethylimidazo[1,2-b]pyrimido[4,5-d]pyridazin-5(6H)-one;

6-(2,6-dichlorophenyl)-2-((3-methyl-4-(4-(dimethylamino)piperidin-1-yl)phenyl)amino)-9-isopropylimidazo[1,2-b]pyrimido[4,5-d]pyridazin-5(6H)-one;

6-(2,6-dichlorophenyl)-2-((3-methyl-4-(4-methylpiperazin-1-yl)phenyl)amino)9-(hydroxymethyl)imidazo[1,2-b]pyrimido[4,5-d]pyridazin-5(6H)-one;

6-allyl-2-((3-methyl-4-(4-(dimethylamino)piperidin-1-yl)phenyl)amino)imidazo[1,2-b]pyrimido[4,5-d]pyridazin-5(6H)-one;

or a pharmaceutically acceptable salt thereof.

6. A pharmaceutical composition comprising the compound of claim 1 and a pharmaceutically acceptable carrier.

7. The pharmaceutical composition of claim 6, further comprising at least one known anticancer agent, or a pharmaceutically acceptable salt of said anticancer agent.

8. The pharmaceutical composition of claim 7, wherein the at least one known anticancer agent is busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, elliptinium, etoposide, 5-azacytidine, gemcitabine, 5-fluorouracil, methotrexate, 5-fluoro-2'-deoxy-uridine, fludarabine, nelarabine, ara-C, pralatrexate, pemetrexed, hydroxyurea, thioguanine, colchicine, vinblastine, vincristine, vinorelbine, paclitaxel, ixabepilone, cabazitaxel, docetaxel, campath, panitumumab, metazotuzumab, navuzumab, pymzumab, remoluzumab, bevacizumab, partuzumab, trastuzumab, cetuximab, obinutuzumab, olfamzumab, rituximab, alemtuzumab, tiemuzumab, toximab, bentuximab, daremuzumab, errotuzumab, T-DM1, ofatumumab, dinutuximab, blinatumomab, ipilimma, avastin, trastuzumab, rituximab, imatinib, gefitinib, erlotinib, osimertinib, afatinib, ceritinib, aletinib, crizotinib, erlotinib, lapatinib, sorafenib, sunitinib, nilotinib, dasatinib, pazopanib, temsirolimus, everolimus, vorinostat, romidepsin, panobinostat, belinostat, tamoxifen, letrozole, fulvestrant, mitoguazone, octreotide, retinoic acid, arsenic trioxide, zoledronic acid, bortezomib, carfilzomib, ixazomib, vismodegib, sonidegib, denosumab, thalidomide, lenalidomide, venetoclax, aldesleukin (recombinant human interleukin-2), sipueucel-T (prostate cancer therapeutic vaccine), palbociclib, olaparib, niraparib, rucaparib or talazoparib.

9. The compound of claim 2, wherein $R_1$ is selected from phenyl which is optionally substituted by 1-4 groups selected from halo and $C_1$-$C_6$ alkyl.

10. The compound of claim 2, wherein $R_2$ is selected from phenyl and tetrahydroisoquinolinyl optionally substituted by one, two, three, or four substituents selected from the group consisting of: halo, $C_1$-$C_6$ alkyl, oxy group, and heterocyclic group optionally substituted by 1-4 substituents selected from the group consisting of $C_1$-$C_6$ alkyl and —$NR_aR_b$, wherein $R_a$ and $R_b$ are each independently H and $C_1$-$C_6$ alkyl, and the heterocyclic group is a saturated or partially saturated 3-7 membered monocyclic or 7-10 membered bicyclic ring system.

11. The compound of claim 10, wherein the heterocyclic group is piperazinyl or piperidinyl.

12. The compound of claim 4, wherein Ar is phenyl optionally substituted by 1-4 groups selected from halo and $C_1$-$C_6$ alkyl.

13. The compound of claim 4, wherein $Ar_2$ is phenyl substituted by piperazinyl which is optionally substituted or phenyl substituted by piperidyl which is optionally substituted.

14. The compound of claim 13, wherein piperazinyl is optionally substituted by one to three $C_1$-$C_6$ alkyl and piperidyl is optionally substituted by one group selected from $C_1$-$C_6$ alkyl and —$NR_aR_b$, wherein $R_a$ and $R_b$ are each independently H or $C_1$-$C_6$ alkyl.

15. The compound of claim 3, wherein the compound of Formula II has a structure represented by Formula III:

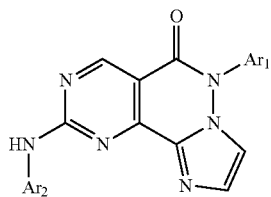

wherein:
  $Ar_1$ is selected from phenyl substituted by 1 or 2 substituents selected from halo and $C_1$-$C_6$ alkyl; and
  $Ar_2$ is substituted phenyl, of which the substituents are selected from: halo, $C_1$-$C_6$ alkyl, $C_1$-$C_6$ alkoxy, piperazinyl optionally substituted by 1-3 $C_1$-$C_6$ alkyl and piperidinyl optionally substituted by one substituent selected from $C_1$-$C_6$ alkyl and —$NR_aR_b$; or $Ar_2$ is tetrahydroisoquinolinyl optionally substituted by 1-3 $C_1$-$C_6$ alkyl; wherein $R_a$ and $R_b$ are each independently H or $C_1$-$C_6$ alkyl.

16. The compound of claim 15, wherein:
  $Ar_1$ is selected from phenyl substituted by 2 substituents selected from halo and $C_1$-$C_6$ alkyl; and
  $Ar_2$ is substituted phenyl, of which the substituents are selected from: halo, $C_1$-$C_6$ alkyl, $C_1$-$C_6$ alkoxy, piperazinyl optionally substituted by 1-3 $C_1$-$C_6$ alkyl and piperidinyl optionally substituted by one substituent selected from $C_1$-$C_6$ alkyl and —$NR_aR_b$; or $Ar_2$ is tetrahydroisoquinolinyl optionally substituted by 1-3 $C_1$-$C_6$ alkyl; wherein $R_a$ and $R_b$ are each independently H or $C_1$-$C_6$ alkyl.

17. The compound of claim 15, wherein:
  $Ar_1$ is di-substituted phenyl substituted by substituents selected from halo and $C_1$-$C_3$ alkyl at two meta-positions;
  $Ar_2$ is phenyl substituted by 1, 2, or 3 substituents selected from halo, $C_1$-$C_6$ alkyl, $C_1$-$C_6$ alkoxy, piperazinyl optionally substituted by 1-3 $C_1$-$C_6$ alkyl and piperidinyl substituted by 1 substituent selected from $C_1$-$C_6$ alkyl and —$NR_aR_b$; or $Ar_2$ is tetrahydroisoquinolinyl substituted by 1-3 $C_1$-$C_6$ alkyl; wherein $R_a$ and $R_b$ are independently H and $C_1$-$C_4$ alkyl.

18. The compound of claim 15, wherein:

$Ar_1$ is selected from the following:

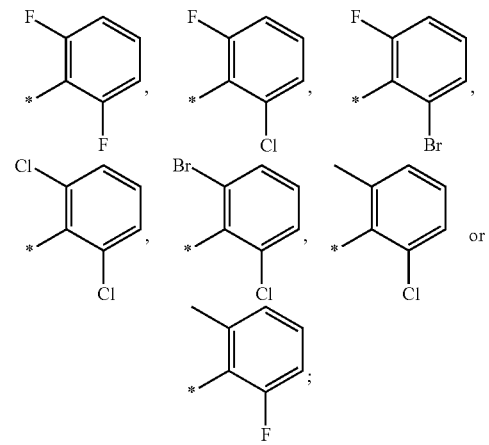

and $Ar_2$ is selected from the following:

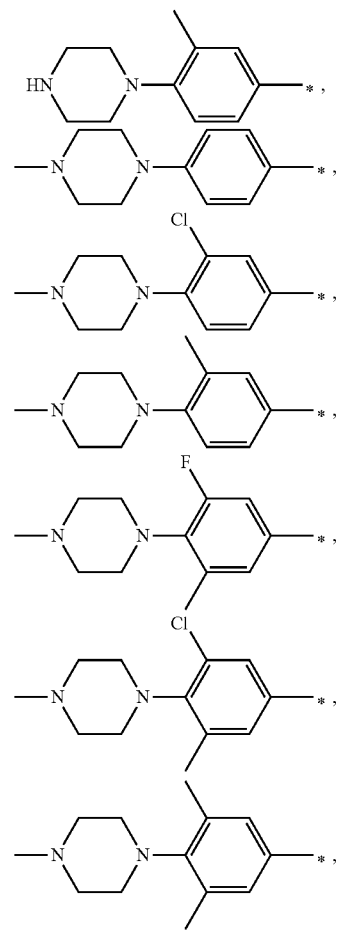

-continued

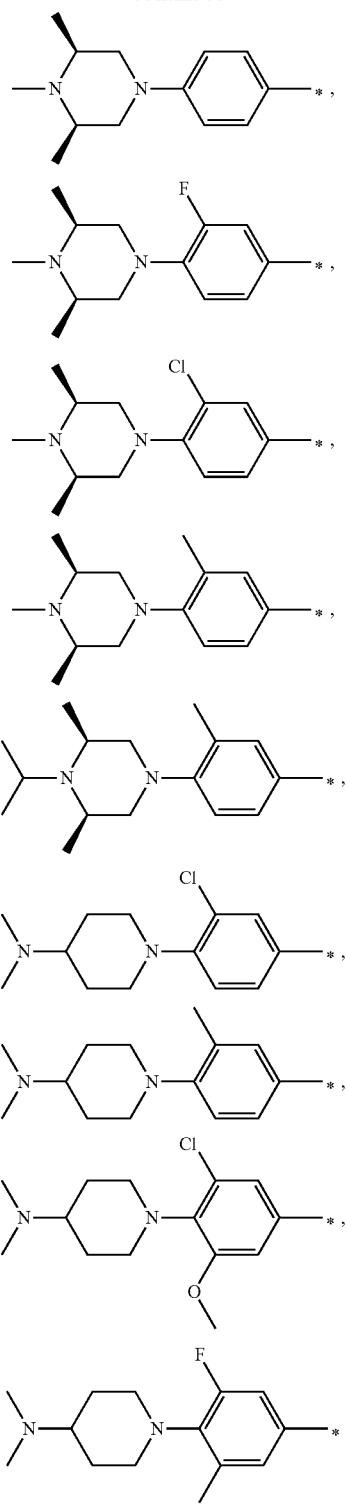

-continued

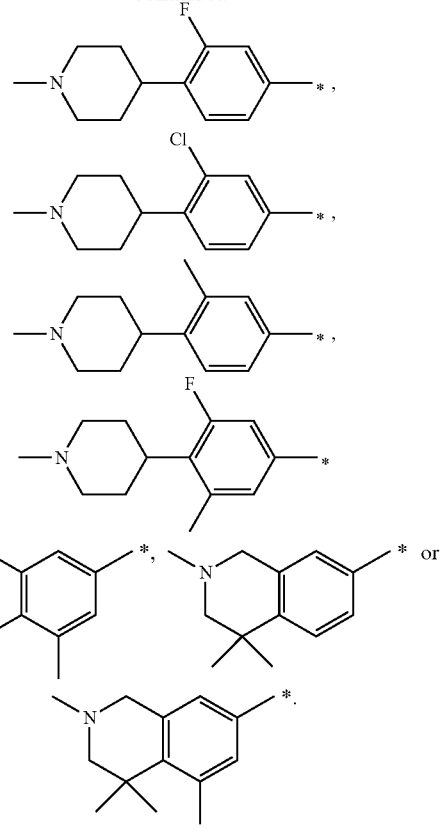

19. A method for treating a Wee1-mediated disease, comprising administering to a mammal an effective amount of a compound of claim 1 or a pharmaceutically acceptable salt thereof.

20. The method of claim 19, wherein said disease is cancer selected from the group consisting of liver cancer, melanoma, Hodgkin's disease, non-Hodgkin's lymphomas, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, malignant melanoma, choriocarcinoma, mycosis fungoide, head and neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

\* \* \* \* \*